(12) United States Patent
Brown et al.

(10) Patent No.: US 7,498,161 B2
(45) Date of Patent: Mar. 3, 2009

(54) MUTANT HERPES SIMPLEX VIRUSES COMPRISING NUCLEIC ACID ENCODING A NITROREDUCTASE

(75) Inventors: Susanne Moira Brown, Glasgow (GB); Paul Dunn, Glasgow (GB)

(73) Assignee: Crusade Laboratories Limited, Glasgow, Scotland (GB)

( * ) Notice: Subject to any disclaimer, the term of this patent is extended or adjusted under 35 U.S.C. 154(b) by 0 days.

(21) Appl. No.: 10/579,606

(22) PCT Filed: Nov. 17, 2004

(86) PCT No.: PCT/GB2004/004851

§ 371 (c)(1),
(2), (4) Date: May 16, 2006

(87) PCT Pub. No.: WO2005/049845

PCT Pub. Date: Jun. 2, 2005

(65) Prior Publication Data

US 2007/0098689 A1    May 3, 2007

(30) Foreign Application Priority Data

Nov. 17, 2003  (GB) ................................. 0326798.6

(51) Int. Cl.
*C12N 7/00*  (2006.01)
(52) U.S. Cl. .................................................. 435/235.1
(58) Field of Classification Search ...................... None
See application file for complete search history.

(56) References Cited

U.S. PATENT DOCUMENTS

| 5,922,576 A |   | 7/1999 | He et al. |
| 6,114,146 A | * | 9/2000 | Herlitschka et al. ........ 435/69.7 |
| 6,573,090 B1 |   | 6/2003 | Breakefield et al. |

FOREIGN PATENT DOCUMENTS

| EP | 0 353 851 | | 2/1990 |
| EP | 0 538 496 | | 4/1993 |
| EP | 0 753 581 | | 1/1997 |
| WO | WO 93/08288 | * | 4/1993 |
| WO | WO 95/04139 | | 2/1995 |
| WO | WO 96/05291 | | 2/1996 |
| WO | WO 97/04804 | | 2/1997 |
| WO | WO 97/14808 | | 4/1997 |
| WO | WO 98/51809 | | 11/1998 |
| WO | WO 99/38955 | * | 8/1999 |
| WO | WO 99/55345 | | 11/1999 |
| WO | WO 01/16331 | | 3/2001 |
| WO | WO 01/46449 | | 6/2001 |
| WO | WO 01/53506 | | 7/2001 |
| WO | WO03/018788 | | 3/2003 |

OTHER PUBLICATIONS

Perna et al., Genome sequence of enterohaemorrhagic *Escherichia coli* O157:H7, Nature, 2001, 409:529-53 (with sequence alignment).*
Coukos et al., Use of Carrier Cells to Deliver a Replication-selective Herpes Simplex Virus-1 Mutant for the Intraperitoneal Therapy of Epithelial Ovarian Cancer, Clinical Cancer Research, 1999, 5:1523-1537.*
Liu et al., "ICP34.5 deleted herpes simplex virus with enhanced oncolytic, immune stimulating, and anti-tumour properties," *Gene Therapy* 10:292-303 (2003).
Gomez-Lira et al., "CD45 and multiple sclerosis: the exon 4 C77G polymorphism (additional studies and meta-analysis) and new markers," *Journal of Neuroummunology* 140:216-221 (2003).
McNeish et al., "Virus directed enzyme prodrug therapy for ovarian and pancreatic cancer using retrovirally delivered *E. coli* nitroreductase and CB1954," *Gene Therapy* 5:1061-1069 (1998).
Varghese et al., "Oncolytic herpes simplex virus vectors for cancer virotherapy," *Cancer Gene Therapy* 9:967-978 (2002).
Weedon et al., "Sensitisation of human carcinoma cells to the prodrug cb1954 by adenovirus vector-mediated expression of *E. coli* ntiroreductase," *Int. J. Cancer* 86:848-854 (2000).
Watanabe et al. (1990) Nucleic Acids Research "Nucleotide sequence of *Salmonella typhimurium* nitroreductase gene" 18(4):1059.
Bryant et al. (1991) J. Biol. Chem "Cloning, Nucleotide Sequence, and Expression of the Nitroreductase Gene from *Enterobacter cloacae*" 266(7):4126-4130.

\* cited by examiner

*Primary Examiner*—Bruce Campell
*Assistant Examiner*—Nicole Kinsey White
(74) *Attorney, Agent, or Firm*—Swanson & Bratschun, L.L.C.

(57) ABSTRACT

An herpes simplex virus wherein the herpes simplex virus genome comprises nucleic acid encoding a nitroreductase (NTR) is disclosed. Disclosed herpes simplex viruses are indicated to be useful in the treatment of cancer which may involve gene directed enzyme prodrug therapy.

1 Claim, 33 Drawing Sheets

A.
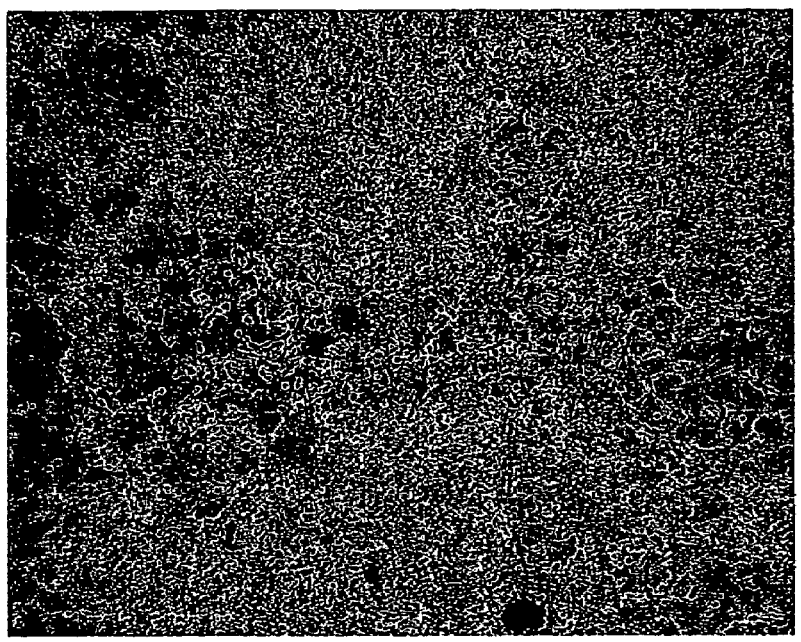
B.
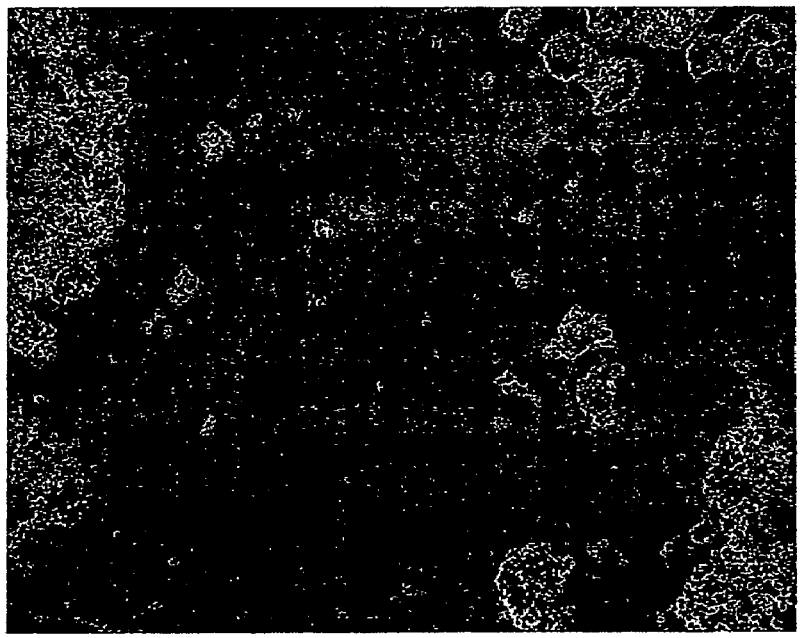
Figure 18

A.
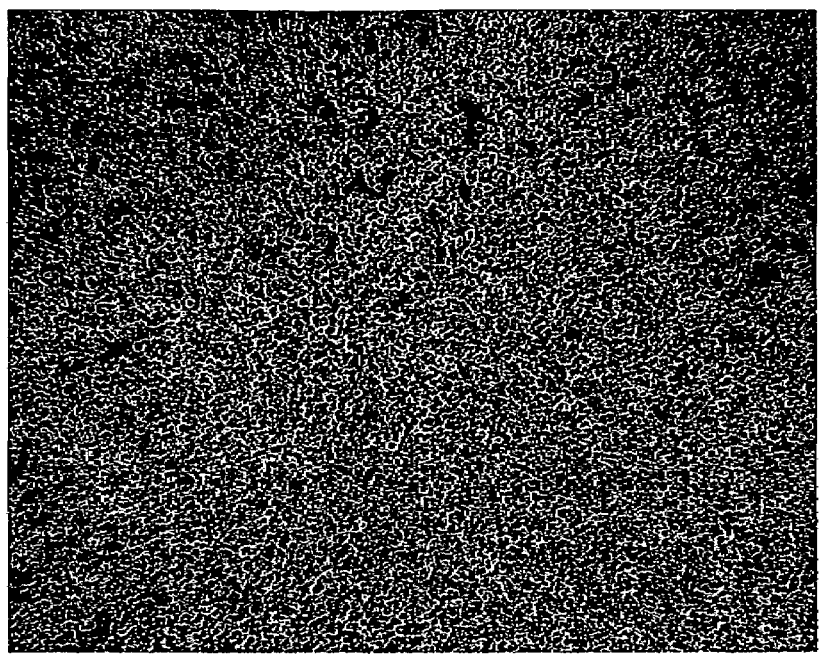
B.
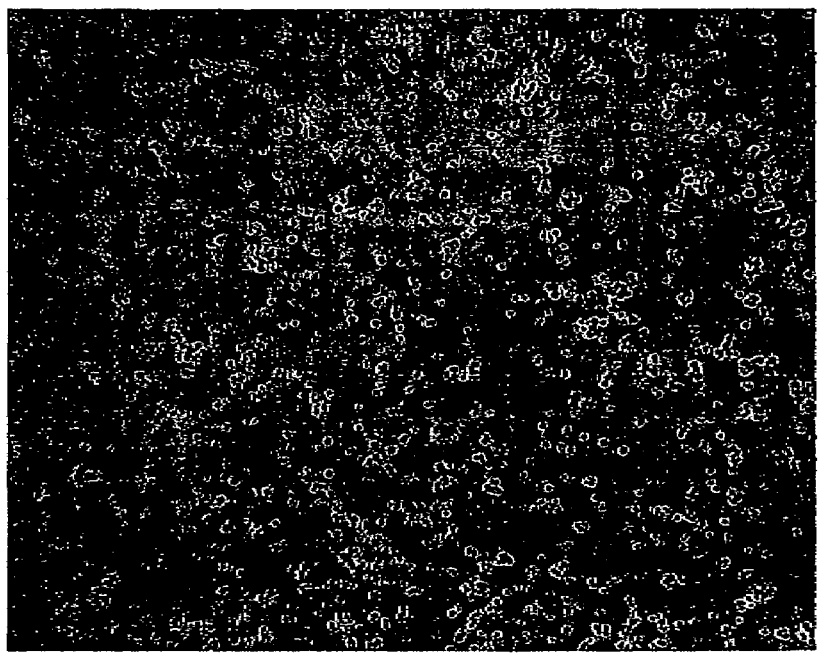
Figure 19

(A)     SEQ ID No. 1

MDIISVALKRHSTKAFDASKKLTPEQAEQIKTLLQYSPSSTNSQ
PWHFIVASTEEGKARVAKSAAGNYVFNERKILDASHVVVFCAKTAMDDAWLKLVVDQE
DADGRFATPEAKAANDKGRKFFADMHRKDLHDDAEWMAKQVYLNVGNFLLGVAALGLD
AVPIEGFDAAILDAEFGLKEKGYTSLVVVPVGHHSVEDFNATLPKSRLPQNITLTEV (B)     SEQ ID No.2

1 atggatatca tttctgtcgc cttaaagcgt cattccacta aggcatttga tgccagcaaa
61 aaacttaccc cggaacaggc cgagcagatc aaaactctcc tgcaatacag cccatccagc
121 accaactccc agccgtggca ttttattgtt gccagcacgg aagaaggtaa agcgcgtgtt
181 gccaaatccg ctgccggtaa ttatgtgttc aacgaacgta aatacttga tgcctcgcac
241 gtcgtggtgt tctgtgcaaa aaccgcgatg gacgatgcct ggctgaagct ggttgttgac
301 caggaagatg ctgatggccg ctttgccacg ccggaagcga aagccgcgaa cgataaaggt
361 cgcaagttct tcgccgatat gcaccgtaaa gatctgcatg atgatgcaga gtggatggca
421 aaacaggttt atctcaacgt cggtaatttc ctgctcggcg tggcggctct gggtctggac
481 gcggtaccca tcgaaggttt tgacgccgcc atcctcgatg cagaatttgg tctgaaagag
541 aaaggctaca ccagtctggt ggtagttccg gtgggtcatc acagcgttga agatttaac
601 gctacgctgc cgaaatctcg tctgccgcaa aacattacct taaccgaagt gtaa

Figure 32

SEQUENCE LISTING

<160> NUMBER OF SEQ ID NOS: 2

<210> SEQ ID NO 1

<211> LENGTH: 217
<212> TYPE: PRT
<213> ORGANISM: Escherichia coli

<400> SEQUENCE: 1

```
Met Asp Ile Ile Ser Val Ala Leu Lys Arg His Ser Thr Lys Ala Phe
1               5                   10                  15

Asp Ala Ser Lys Lys Leu Thr Pro Glu Gln Ala Glu Gln Ile Lys Thr
            20                  25                  30

Leu Leu Gln Tyr Ser Pro Ser Ser Thr Asn Ser Gln Pro Trp His Phe
        35                  40                  45

Ile Val Ala Ser Thr Glu Glu Gly Lys Ala Arg Val Ala Lys Ser Ala
    50                  55                  60

Ala Gly Asn Tyr Val Phe Asn Glu Arg Lys Ile Leu Asp Ala Ser His
65                  70                  75                  80

Val Val Val Phe Cys Ala Lys Thr Ala Met Asp Asp Ala Trp Leu Lys
                85                  90                  95

Leu Val Val Asp Gln Glu Asp Ala Asp Gly Arg Phe Ala Thr Pro Glu
            100                 105                 110

Ala Lys Ala Ala Asn Asp Lys Gly Arg Lys Phe Phe Ala Asp Met His
        115                 120                 125

Arg Lys Asp Leu His Asp Asp Ala Glu Trp Met Ala Lys Gln Val Tyr
130                 135                 140

Leu Asn Val Gly Asn Phe Leu Leu Gly Val Ala Ala Leu Gly Leu Asp
145                 150                 155                 160

Ala Val Pro Ile Glu Gly Phe Asp Ala Ala Ile Leu Asp Ala Glu Phe
                165                 170                 175

Gly Leu Lys Glu Lys Gly Tyr Thr Ser Leu Val Val Val Pro Val Gly
            180                 185                 190

His His Ser Val Glu Asp Phe Asn Ala Thr Leu Pro Lys Ser Arg Leu
        195                 200                 205

Pro Gln Asn Ile Thr Leu Thr Glu Val
    210                 215
```

<210> SEQ ID NO 2
<211> LENGTH: 654
<212> TYPE: DNA
<213> ORGANISM: Escherichia coli

<400> SEQUENCE: 2

```
atggatatca tttctgtcgc cttaaagcgt cattccacta aggcatttga tgccagcaaa      60
aaacttaccc cggaacaggc cgagcagatc aaaactctcc tgcaatacag cccatccagc     120
accaactccc agccgtggca ttttattgtt gccagcacgg aagaaggtaa agcgcgtgtt     180
gccaaatccg ctgccggtaa ttatgtgttc aacgaacgta aaatacttga tgcctcgcac     240
gtcgtggtgt tctgtgcaaa aaccgcgatg acgatgcct ggctgaagct ggttgttgac      300
caggaagatg ctgatggccg ctttgccacg ccggaagcga agccgcgaa cgataaaggt       360
cgcaagttct tcgccgatat gcaccgtaaa gatctgcatg atgatgcaga gtggatggca     420
aaacaggttt atctcaacgt cggtaatttc ctgctcggcg tggcggctct gggtctggac     480
gcggtaccca tcgaaggttt tgacgccgcc atcctcgatg cagaatttgg tctgaaagag     540
aaaggctaca ccagtctggt ggtagttccg gtgggtcatc acagcgttga agattttaac     600
gctacgctgc cgaaatctcg tctgccgcaa acattacct taaccgaagt gtaa             654
```

MUTANT HERPES SIMPLEX VIRUSES COMPRISING NUCLEIC ACID ENCODING A NITROREDUCTASE

CROSS REFERENCE TO RELATED APPLICATIONS

This is the U.S. National Stage of International Application No. PCT/GB2004/004851, filed Nov. 17, 2004, which in turn claims the benefit of Great Britain Application No. 0326798.6, filed Nov. 17, 2003. Both of these applications are incorporated herein by reference in their entirety.

FIELD OF THE INVENTION

The present invention relates to mutant herpes simplex viruses wherein the herpes simplex virus genome comprises nucleic acid encoding a nitroreductase.

BACKGROUND TO THE INVENTION

Herpes Simplex Virus

The herpes simplex virus (HSV) genome comprises two covalently linked segments, designated long (L) and short (S). Each segment contains a unique sequence flanked by a pair of inverted terminal repeat sequences. The long repeat (RL or $R_L$) and the short repeat (RS or $R_S$) are distinct.

The HSV ICP34.5 (also γ34.5) gene, which has been extensively studied[1, 6, 7, 8], has been sequenced in HSV-1 strains F[9] and syn17+[3] and in HSV-2 strain HG52[4]. One copy of the ICP34.5 gene is located within each of the RL repeat regions. Mutants inactivating both copies of the ICP34.5 gene (i.e. null mutants), e.g. HSV-1 strain 17 mutant 1716[2] (HSV 1716) or the mutants R3616 or R4009 in strain F[5], are known to lack neurovirulence, i.e. be a virulent, and have utility as both gene delivery vectors or in the treatment of tumours by oncolysis. HSV-1 strain 17 mutant 1716 has a 759 bp deletion in each copy of the ICP34.5 gene located within the BamHI s restriction fragment of each RL repeat.

ICP34.5 null mutants such as HSV1716 are, in effect, first-generation oncolytic viruses. Most tumours exhibit individual characteristics and the ability of a broad spectrum first generation oncolytic virus to replicate in or provide an effective treatment for all tumour types is not guaranteed.

HSV 1716 is described in EP 0571410 and WO 92/13943 and has been deposited on 28 Jan. 1992 at the European Collection of Animal Cell Cultures, Vaccine Research and Production Laboratories, Public Health Laboratory Services, Porton Down, Salisbury, Wiltshire, SP4 0JG, United Kingdom under accession number V92012803 in accordance with the provisions of the Budapest Treaty on the International Recognition of the Deposit of Microorganisms for the Purposes of Patent Procedure (herein referred to as the 'Budapest Treaty').

Nitroreductase Prodrug Activation

Enzyme prodrug therapy is based on the enzymatic activation of a non toxic or low toxicity prodrug to a form that is considerably more cytotoxic. The activation may involve enzymatic reduction of the prodrug to a cytotoxic reduced form.

The E. coli nitroreductase enzyme (NTR) has been proposed for use in gene-directed enzyme prodrug therapy (GDEPT) as an activating enzyme for nitroaromatic prodrugs of the dinitrobenzamide class[16]. E. coli NTR is a homodimeric enzyme with two active sites and is the oxygen insensitive enzyme from E. coli (the nfsB gene product). It has the ability to reduce a wide range of nitro-containing compounds such as nitrofurazone (to the hydroxylamines) and quinones such as menadione (to the quinols). It is specifically inhibited by the irreversible inhibitor dicoumarol.

The ability of NTR to reduce aromatic nitro groups to the corresponding hydroxylamine (and possibly amine) derivatives has been proposed for cancer chemotherapy mainly with the dinitrobenzamide class of prodrugs. The 5-aziridin-1-yl-2,4-dinitrobenzamide CB1954 (CAS Registry number 21919-05-1) is one such prodrug which has been studied as a prodrug for GDEPT with NTR[16].

Cyclic and acyclic nitroaryl phosphoroamide mustard analogues have also been shown to be activated by E. coli NTR[17]. The acyclic 4-nitrobenzyl phosphoramide mustard showed 167,500× selective cytotoxicity toward nitroreductase-expressing V79 cells with an $IC_{50}$ as low as 0.4 nM which is about 100× more active and 27× more selective than CB1954.

Recombinant adenovirus and recombinant retrovirus[10] expressing nitroreductase have been constructed for use with the prodrug CB1954 with the intention of providing a treatment for cancer. The recombinant virus is not oncolytic and relies on gene directed enzyme-prodrug therapy to achieve tumour cell kill.

SUMMARY OF THE INVENTION

The inventors have determined that herpes simplex virus having an inactivating mutation in the RL1 locus, more specifically a mutation which inactivates the function of the ICP34.5 gene product, such that the herpes simplex virus does not produce a functional ICP34.5 gene product and is non-neurovirulent, can be used in the delivery to a cell of a gene encoding a gene product useful in targeted tumour therapy.

The inventors have provided a novel second generation oncolytic mutant HSV. The genome of this mutant HSV comprises the heterologous (i.e. non-HSV originating) E. coli nitroreductase protein coding sequence inserted at one or each ICP34.5 locus, disrupting the ICP34.5 protein coding sequence such that the ICP34.5 gene is non-functional and cannot express a functional ICP34.5 gene product. The generated HSV is capable of expressing the E. coli nitroreductase gene product under control of the inserted promoter. This virus thus has the oncolytic activity of HSV strain 17 mutant 1716 and can be used in gene directed enzyme-prodrug therapy (GDEPT) and has shown significantly enhanced tumour cell killing in vitro and in vivo when used with the prodrug CB1954. The mutant virus is designated HSV1716/CMV-NTR/GFP (also called HSV1790).

HSV1716/CMV-NTR/GFP is an engineered herpes simplex virus ICP34.5 null mutant which expresses the nitroreductase (NTR) gene. This virus provides for enhanced virus induced tumour cytotoxicity. It combines NTR transgene delivery and CB1954 prodrug treatment with the proliferation-specific, lytic capacity of HSV1716.

The heterologous nitroreductase polypeptide expressed by an herpes simplex virus according to the present invention may be useful in gene directed enzyme-prodrug targeting techniques for tissue specific delivery of active pharmaceutical agents derived by nitroreductase dependent activation of the NTR prodrug.

In vivo, the inventors have demonstrated that the nitroreductase gene, when introduced by HSV1716/CMV-NTR/GFP into mouse gliomal xenograft models in combination with the prodrug CB1954, results in delay in tumour growth and in oncolysis. Administering both the HSV1716/CMV-NTR/GFP virus and CB1954 prodrug in combination was observed to produce a greater effect than either virus or prodrug alone, i.e. the combination exhibits a synergistic effect.

The results demonstrate that the combination of oncolytic HSV therapy with gene therapy directed nitroreductase/prodrug treatment provides an effective means of tumour cell kill and tumour growth reduction and thereby a treatment for tumour.

Combining herpes simplex virus HSV1716-mediated oncolysis with nitroreductase gene transfer has yielded results exhibiting a surprising synergy and provides a novel therapeutic strategy for treatment of tumours of all kinds.

HSV1716/CMV-NTR/GFP has been deposited in the name of Crusade Laboratories Limited having an address at Department of Neurology Southern General Hospital 1345 Govan Road Govan Glasgow G51 5TF Scotland on 5 Nov. 2003 at the European Collection of Cell Cultures (ECACC), Health Protection Agency, Porton Down, Salisbury, Wiltshire, SP4 0JG, United Kingdom under accession number 03110501 in accordance with the provisions of the Budapest Treaty on the International Recognition of the Deposit of Microorganisms for the Purposes of Patent Procedure (herein referred to as the 'Budapest Treaty').

Accordingly, the present invention relates to a herpes simplex virus, wherein the herpes simplex virus genome comprises a nucleic acid sequence encoding a nitroreductase. The herpes simplex virus may also be non-neurovirulent.

At its most general the present invention relates to an herpes simplex virus wherein the herpes simplex virus genome comprises nucleic acid encoding a nitroreductase.

According to one aspect of the present invention there is provided an herpes simplex virus wherein the herpes simplex virus genome comprises nucleic acid encoding an heterologous nitroreductase (NTR).

Said nucleic acid may encode an *E. coli* NTR and may comprise, consist of or include the nucleic acid sequence of SEQ ID No. 2. Alternatively the nucleic acid may have at least 60% sequence identity to SEQ ID No. 2. Said degree of sequence identity may alternatively be one of at least 70%, 80%, 90%, 95%, 96%, 97%, 98% or 99% provided the polypeptide or protein encoded by such nucleic acid has a nitroreductase function. Identity of sequences is determined across the entire length of a given nucleotide sequence. Where sequences are of different length, sequence identity of the shorter sequence is determined over the entire length of the longer sequence.

Said nucleic acid encoding NTR may be selected by its ability to hybridise to the nucleic acid of SEQ ID No. 2, or its complement, under high stringency conditions.

The genome of said herpes simplex virus may further comprise a regulatory sequence operably linked to said nucleic acid encoding NTR, wherein said regulatory sequence has a role in controlling transcription of said nucleic acid.

The nucleic acid encoding NTR may be located in at least one RL1 locus of the herpes simplex virus genome. Suitably it may be located in, or overlap, at least one of the ICP34.5 protein coding sequences of the herpes simplex virus genome. The nucleic acid may be located in both (this will usually be all) copies of the RL1 locus or ICP34.5 protein coding sequence.

The herpes simplex virus is preferably a mutant and may be a mutant of HSV-1 or HSV-2, more preferably of one of HSV-1 strains 17, F or HSV-2 strain HG52. The herpes simplex virus may be a further mutant of HSV-1 strain 17 mutant 1716.

In certain arrangements the herpes simplex virus may be a gene specific null mutant, such as an ICP34.5 null mutant.

In other arrangements the herpes simplex virus may lack at least one expressible ICP34.5 gene.

In yet another arrangement the herpes simplex virus may lack only one expressible ICP34.5 gene.

In yet another arrangement the herpes simplex virus may be non-neurovirulent.

In herpes simplex viruses of the present invention the nucleic acid encoding the NTR may form part of a nucleic acid cassette permanently integrated in the herpes simplex virus genome, said cassette comprising nucleic acid encoding:

(a) said nucleic acid encoding NTR; and nucleic acid encoding:
(a) a ribosome binding site; and
(b) a marker, wherein the nucleic acid encoding NTR is arranged upstream (5') of the ribosome binding site and the ribosome binding site is arranged upstream (5') of the marker, wherein said ribosome binding site has a role in controlling transcription of said marker.

A regulatory nucleotide sequence may be located upstream (5') of the nucleic acid encoding NTR, wherein the regulatory nucleotide sequence has a role in controlling and regulating transcription of the nucleic acid encoding the NTR and hence expression of the resulting transcript and polypeptide. The regulatory sequence may comprise selected promoter or enhancer elements known to the person skilled in the art, e.g. the CytoMegalovirus (CMV) promoter. Suitably the regulatory sequence may be constitutive or inducible.

The components of the cassette are preferably arranged in a predetermined order.

In one preferred arrangement, the nucleic acid encoding NTR is arranged upstream (i.e. 5') of the ribosome binding site and the ribosome binding site is arranged upstream (i.e. 5') of the marker. During transcription a single transcript may be produced from the cassette comprising a first cistron comprising nucleic acid encoding NTR (e.g. an mRNA transcript) and a second cistron comprising nucleic acid encoding the marker wherein the ribosome binding site is located between the cistrons.

A transcription product of this cassette may be a bi- or poly-cistronic transcript comprising a first cistron encoded by the nucleic acid encoding NTR and a second cistron encoding the marker nucleic acid wherein the ribosome binding site is located between said first and second cistrons.

In another arrangement, the nucleic acid encoding the NTR may be arranged upstream (i.e. 5') of a first regulatory nucleotide sequence and the first regulatory nucleotide sequence is arranged upstream (i.e. 5') of the marker.

The cassette may disrupt a protein coding sequence of the herpes simplex virus genome resulting in inactivation of the respective gene product.

One suitable ribosome binding site comprises a ribosome entry site permitting entry of a ribosome to the transcribed mRNA encoded by the nucleic acid of the cassette such that the ribosome binds to the translation start signal. Preferably, the ribosome entry site is an internal ribosome entry site (IRES), more preferably an encephalomyocarditis virus IRES, permitting cap-independent initiation of translation. The IRES thus enables translation of a coding sequence located internally of a bi- or poly-cistronic mRNA, i.e. of a cistron located downstream of an adjacent cistron on a single transcript.

Preferably the marker is a defined nucleotide sequence coding for a polypeptide which can be expressed in a cell line (e.g. BHK cells) infected with mutant herpes simplex virus into which the cassette has been recombined. The function of the marker is to enable identification of virus plaques containing mutant virus transformed with the cassette.

The marker is preferably a detectable marker, more preferably an expressible marker polypeptide or protein comprising at least the coding sequence for the selected polypeptide or protein. The nucleic acid encoding the marker may further comprise regulatory sequence upstream and/or downstream of the coding sequence having a role in control of transcription of the marker mRNA. Preferred markers include the Green Fluorescent Protein (GFP) protein coding sequence or gene, preferably the enhanced Green Fluorescent Protein (EGFP) protein coding sequence or gene.

In other arrangements the marker may comprise a defined nucleotide sequence which can be detected by hybridisation under high stringency conditions with a corresponding labelled nucleic acid probe, e.g. using a fluorescent- or radio-label.

The cassette may also comprise nucleic acid encoding a polyadenylation ("polyA") sequence, which sequence is preferably located downstream (3') of the nucleic acid encoding the marker. One preferred polyA sequence is the Simian Virus 40 (SV40) polyadenylation sequence. The preferred location of the polyA sequence within the cassette is immediately downstream (i.e. 3') of the marker.

Mutant herpes simplex viruses of the present invention may be generated by site directed insertion of a nucleic acid cassette into the viral genome, more preferably by homologous recombination. However, the viruses of the invention are not limited to Herpes simplex viruses obtained in this way.

In other aspects of the present invention herpes simplex viruses according to the present invention are provided for use in a method of medical treatment. Suitably they are provided for use in the treatment of disease. Preferably they are provided for use in the treatment of cancer. Suitably they may be provided for use in the oncolytic treatment of cancer/a tumour. The use of herpes simplex viruses according to the present invention in the manufacture of a medicament for the treatment of cancer is also provided.

In another aspect of the present invention medicaments comprising herpes simplex virus mutants according to the present invention for use in oncotherapy and methods of treating tumours comprising administering to a patient in need of treatment an effective amount of a mutant HSV or a medicament comprising or derived from such HSV are also provided. Methods of lysing or killing tumour cells in vitro or in vivo comprising the step of administering to a patient in need of treatment an amount of an Herpes simplex virus according to the present invention are also provided.

A medicament, pharmaceutical composition or vaccine comprising an Herpes simplex virus according to the present invention is also provided. The medicament, pharmaceutical composition or vaccine may further comprise a pharmaceutically acceptable carrier, adjuvant or diluent. Pharmaceutical compositions or vaccines may further comprise an NTR prodrug.

The present invention may also include the following aspects which may be provided in combination with any of the other aspects and features described.

According to another aspect of the present invention a herpes simplex virus is provided, wherein the genome of said virus comprises a nucleic acid sequence encoding an heterologous nitroreductase (NTR) in at least one of the long repeat regions ($R_L$).

According to another aspect of the present invention a herpes simplex virus is provided, wherein the genome of said virus comprises a nucleic acid sequence encoding an heterologous nitroreductase (NTR) and wherein the herpes simplex virus is non-neurovirulent.

A composition comprising a herpes simplex virus of the invention may be provided in combination with an NTR prodrug. The NTR prodrug may be CB1954.

According to another aspect of the present invention a herpes simplex virus for use in the treatment of a tumour is provided, wherein the genome of said virus comprises a nucleic acid sequence encoding an heterologous nitroreductase in at least one of the long repeat regions ($R_L$).

According to another aspect of the present invention a herpes simplex virus for use in the treatment of a tumour is provided, wherein the genome of said virus comprises a nucleic acid sequence encoding an heterologous nitroreductase and wherein the herpes simplex virus is non-neurovirulent.

According to another aspect of the present invention a herpes simplex virus is provided, wherein the genome of said virus comprises a nucleic acid sequence encoding an heterologous nitroreductase in at least one of the long repeat regions ($R_L$), for use, in combination with an NTR prodrug, in the treatment of a tumour.

According to another aspect of the present invention a herpes simplex virus is provided, wherein the genome of said virus comprises a nucleic acid sequence encoding an heterologous nitroreductase and wherein the herpes simplex virus is non-neurovirulent, for use, in combination with an NTR prodrug, in the treatment of a tumour.

According to another aspect of the present invention a kit of parts is provided comprising a first container having a quantity of an herpes simplex virus of the invention and a second container having a quantity of an NTR prodrug.

In another aspect the use of a herpes simplex virus, wherein the genome of said virus comprises a nucleic acid sequence encoding an heterologous nitroreductase in at least one of the long repeat regions ($R_L$), in the manufacture of a medicament for the treatment of a tumour is also provided.

In another aspect the use of a herpes simplex virus, wherein the genome of said virus comprises a nucleic acid sequence encoding an heterologous nitroreductase and wherein the herpes simplex virus is non-neurovirulent, in the manufacture of a medicament for the treatment of a tumour is also provided.

In another aspect the use in the manufacture of a medicament for the treatment of a tumour of a herpes simplex virus, wherein the genome of said virus comprises a nucleic acid sequence encoding an heterologous nitroreductase in at least one of the long repeat regions ($R_L$), and an NTR prodrug is also provided.

In another aspect the use in the manufacture of a medicament for the treatment of a tumour of a herpes simplex virus, wherein the genome of said virus comprises a nucleic acid sequence encoding an heterologous nitroreductase and wherein the herpes simplex virus is non-neurovirulent, and an NTR prodrug is also provided.

In another aspect the use of a herpes simplex virus, wherein the genome of said virus comprises a nucleic acid sequence encoding an heterologous nitroreductase in at least one of the long repeat regions ($R_L$) in the manufacture of a first medicament for administering sequentially or simultaneously with a second medicament comprising an NTR prodrug in the treatment of a tumour is also provided In another aspect the use of an NTR prodrug in the manufacture of a first medicament for administering sequentially or simultaneously with a second medicament comprising a herpes simplex virus, wherein the genome of said virus comprises a nucleic acid sequence encoding an heterologous nitroreductase in at least one of the long repeat regions ($R_L$), in the treatment of a tumour is also provided.

In another aspect the use of an NTR prodrug in the manufacture of a first medicament for administering sequentially or simultaneously with a second medicament comprising a herpes simplex virus, wherein the genome of said virus comprises a nucleic acid sequence encoding an heterologous nitroreductase and wherein the herpes simplex virus is non-neurovirulent, in the treatment of a tumour is also provided.

In another aspect the use of a herpes simplex virus, wherein the genome of said virus comprises a nucleic acid sequence encoding an heterologous nitroreductase and wherein the herpes simplex virus is non-neurovirulent, in the manufacture of a first medicament for administering sequentially or simultaneously with a second medicament comprising an NTR prodrug, in the treatment of a tumour is also provided.

The time period between sequential administrations may be such that the herpes simplex virus and NTR prodrug may interact in the body to produce an active pharmaceutical agent in situ. Preferred time periods may be less than 15 minutes, less than one hour, two hours, three hours, four hours, five hours or six hours, twelve hours, twenty four hours, forty eight hours, one week or two weeks. Either the herpes simplex virus or NTR prodrug may be administered first.

In another aspect a method of treatment of a tumour is provided comprising the steps of:
(i) administering to a patient in need of treatment a herpes simplex virus, wherein the genome of said virus comprises a nucleic acid sequence encoding a nitroreductase in at least one of the long repeat regions ($R_L$); and
(ii) administering to said patient a therapeutically effective amount of an NTR prodrug.

In another aspect a method of treatment of a tumour is provided comprising the steps of:
(i) administering to a patient in need of treatment a herpes simplex virus, wherein the genome of said virus comprises a nucleic acid sequence encoding a nitroreductase and wherein the herpes simplex virus is non-neurovirulent; and
(ii) administering to said patient a therapeutically effective amount of an NTR prodrug.

In the methods of treatment said herpes simplex virus is preferably capable of killing tumour cells, e.g. by oncolysis.

In aspects of the invention involving an NTR prodrug, one preferred prodrug is CB1954.

In another aspect a method of expressing in vitro or in vivo a nitroreductase is provided, said method comprising the step of infecting at least one cell or tissue of interest with a herpes simplex virus, wherein the genome of said virus comprises a nucleic acid sequence encoding a heterologous nitroreductase in at least one of the long repeat regions ($R_L$), said nitroreductase operably linked to a transcription regulatory sequence.

In another aspect a method of expressing in vitro or in vivo a nitroreductase is provided, said method comprising the step of infecting at least one cell or tissue of interest with a non-neurovirulent herpes simplex virus, wherein the genome of said virus comprises a nucleic acid sequence encoding a heterologous nitroreductase, said nitroreductase operably linked to a transcription regulatory sequence.

Herpes simplex viruses of the invention having nucleic acid encoding an heterologous nitroreductase in at least one of the long repeat regions ($R_L$) of the HSV genome preferably have said nucleic acid in each of the long repeat regions of the HSV genome. Two long repeat regions are usually present in the HSV genome.

The NTR nucleotide sequence may encode a full length transcript or polypeptide (i.e. comprise the complete NTR protein coding sequence). Alternatively, provided the polypeptide product retains nitroreductase activity, the NTR nucleotide sequence may comprise one or more fragments of the full length sequence respectively coding for a fragment of the full length transcript or a truncated polypeptide.

A fragment may comprise a nucleotide sequence encoding at least 10% of the corresponding full length sequence, more preferably the fragment comprises at least 20, 30, 40, 50, 60, 70, 80, 85, 90, 95, 96, 97, 98 or 99% of the corresponding full length sequence. Preferably, the fragment comprises at least, i.e. has a minimum length of, 20 nucleotides, more preferably at least 30, 40, 50, 100, 150, 200, 300, 400, 500, 600, 700, 800, 900, 1000, 1100, 1200, 1300, 1400, 1500, 1600, 1700, 1800, 1900 2000, 2100, 2200, 2300, 2400, 2500, 2600, 2700, 2800, 2900, 3000, 3100, 3200, 3300, 3400, 3500, 3600, 3700, 3800, 3900 or 4000 nucleotides. The fragment may have a maximum length, i.e. be no longer than, 20 nucleotides, more preferably no longer than 30, 40, 50, 100, 150, 200, 300, 400, 500, 600, 700, 800, 900, 1000, 1100, 1200, 1300, 1400, 1500, 1600, 1700, 1800, 1900 2000, 2100, 2200, 2300, 2400, 2500, 2600, 2700, 2800, 2900, 3000, 3100, 3200, 3300, 3400, 3500, 3600, 3700, 3800, 3900 or 4000. The fragment length may be anywhere between said minimum and maximum length.

In one preferred arrangement, the mutant HSV is HSV1716/CMV-NTR/GFP deposited in the name of Crusade Laboratories Limited having an address at Department of Neurology Southern General Hospital 1345 Govan Road Govan Glasgow G51 5TF Scotland on 5 Nov. 2003 at the European Collection of Cell Cultures (ECACC), Health Protection Agency, Porton Down, Salisbury, Wiltshire, SP4 0JG, United Kingdom under accession number 03110501 in accordance with the provisions of the Budapest Treaty.

Suitably, the administration of said herpes simplex virus and/or said NTR prodrug may comprise parenteral administration. Preferably administration of the herpes simplex virus is by injection, more preferably injection to the tumour which is to be treated. The NTR prodrug may also be administered by injection, which may also comprise direct injection to the site of the tumour. Alternatively injections may be intravenous.

Administration of the herpes simplex virus and NTR prodrug may be simultaneous, e.g. by combining virus and prodrug in a single composition, or be substantially simultaneous, e.g. one being administered immediately after the other. Alternatively, a predetermined time period may be provided between administration of the herpes simplex virus and the NTR prodrug. The invention is not limited by the order of administration.

In a further aspect of the present invention in vitro or in vivo methods are provided for delivery of nucleic acid encoding a nitroreductase to at least one cell or to a tissue of interest said method comprising the step of infecting said cell(s) or tissue with a herpes simplex virus according to the invention.

In another aspect of the invention, a kit of parts is provided comprising a first container in which a quantity of herpes simplex virus according to the invention is provided and a second container in which a quantity of NTR prodrug is provided. Instructions for the administration, optionally including information on suitable dosages of herpes simplex virus and/or the NTR prodrug, may also be provided with the kit.

In another aspect of the present invention a method of making or producing a modified herpes simplex virus of the invention is provided comprising the step of introducing a nucleic acid sequence encoding a nitroreductase at a selected and/or predetermined insertion site in the genome of a selected herpes simplex virus.

As described, the nucleic acid sequence encoding the nitroreductase may form part of a nucleic acid cassette which is inserted in the genome of a selected herpes simplex virus by homologous recombination. Whether part of a cassette or not, the site of insertion may be in any genomic location selected. One preferred insertion site is in one or both of the long repeat regions ($R_L$), and one copy of the cassette is preferably inserted in each copy of the long repeat ($R_L$). More preferably the insertion site is in at least one (preferably both) RL1 locus and most preferably it is inserted in at least one (preferably both) of the ICP34.5 protein coding sequences of the HSV genomic DNA. It is preferred that the insertion occurs in identical or substantially similar positions in each of the two repeat regions, RL1 loci or ICP34.5 protein coding sequences.

Insertion may be such as to produce a modified virus which is a non-neurovirulent mutant capable of expressing the encoded nitroreductase polypeptide upon transfection into mammalian, more preferably human, cells in vivo and in vitro in a form which is functional to facilitate the uptake and/or activation of NTR prodrug. The non-neurovirulent mutant may be an ICP34.5 null mutant. The nucleic acid cassette may be of any size, e.g. up to 5, 10, 15, 20, 25, 30, 35, 40, 45 or 50 kbp in length.

Preferably, the herpes simplex virus contains at least one copy of the nucleic acid encoding the nitroreductase in each long repeat region ($R_L$), i.e. in the terminal and internal long repeat ($TR_L$ and $IR_L$) regions. In a preferred arrangement each exogenous sequence or cassette is located in an RL1 locus of the herpes simplex virus genome, more preferably in the DNA of the herpes simplex virus genome encoding the ICP34.5 gene or protein coding sequence. The herpes simplex virus thereby lacks neurovirulence.

The parent herpes simplex virus, from which a virus of the invention is derived may be of any kind, e.g. HSV-1 or HSV-2. In one preferred arrangement the herpes simplex virus is a variant of HSV-1 strain 17 and may be obtained by modification of the strain 17 genomic DNA. Suitable modifications include the insertion of the exogenous nitroreductase nucleic acid sequence or exogenous/heterologous cassette comprising said sequence into the herpes simplex virus genomic DNA. The insertion may be performed by homologous recombination of the exogenous nucleic acid sequence into the genome of the selected herpes simplex virus.

Although the non-neurovirulent phenotype of the herpes simplex virus of the invention may be the result of insertion of the exogenous nucleic acid sequence in the RL1 locus, herpes simplex viruses according to the present invention may be obtained by utilising a non-neurovirulent parent strain, e.g. HSV1716 deposited under the Budapest Treaty at the European Collection of Animal Cell Cultures (ECACC), Health Protection Agency, Porton Down, Salisbury, Wiltshire, United Kingdom under accession number V92012803, and inserting the exogenous nucleic acid sequence at another location of the genome by standard genetic engineering techniques, e.g. homologous recombination. In this aspect the location of the herpes simplex virus genome selected for insertion of the nitroreductase nucleic acid sequence or cassette containing said sequence may be a neutral location.

Herpes simplex viruses of the present invention may be variants of a known 'parent' strain from which the herpes simplex virus of the invention has been derived. A particularly preferred parent strain is HSV-1 strain 17. Other parent strains may include HSV-1 strain F or HSV-2 strain HG52. A variant comprises an HSV in which the genome substantially resembles that of the parent, contains the nitroreductase nucleic acid sequence or cassette containing said sequence and may contain a limited number of other modifications, e.g. one, two or three other specific mutations, which may be introduced to disable the pathogenic properties of the herpes simplex virus, for example a mutation in the ribonucleotide reductase (RR) gene, the 65K trans inducing factor (TIF) and/or a small number of mutations resulting from natural variation, which may be incorporated naturally during replication and selection in vitro or in vivo. Otherwise the genome of the variant will be that of the parent strain.

Herpes simplex viruses of the invention may be used alone, or in combination with an NTR prodrug in a method of medical treatment. This may involve treatment of diseases associated with or involving the proliferation of cells, or cancers or tumours of any kind. Treatment may involve the selective lysis of dividing cells. This may be oncolysis, i.e. lysis of tumour cells. Tumours to be treated may be of any kind, may comprise cancers, neoplasms or neoplastic tissue and may be in any animal or human patient.

Cancer/tumour types which may be treated may be primary or secondary (metastatic) tumours. Tumours to be treated may be nervous system tumours originating in the central or peripheral nervous system, e.g. glioma, medulloblastoma, meningioma, neurofibroma, ependymoma, Schwannoma, neurofibrosarcoma, astrocytoma and oligodendroglioma, or may be non-nervous system tumours originating in non-nervous system tissue e.g. melanoma, mesothelioma, lymphoma, hepatoma, epidermoid carcinoma, prostate carcinoma, breast cancer cells, lung cancer cells or colon cancer cells. HSV mutants of the present invention may be used to treat metastatic tumours of the central or peripheral nervous system which originated in a non-nervous system tissue.

Herpes simplex viruses of the invention may be used in 'gene delivery' methods in vitro or in vivo. Non-neurovirulent herpes simplex viruses of the invention are expression vectors and may be used to infect selected cells or tissues in order to express the nitroreductase encoded by the herpes simplex virus genome.

In one arrangement, cells may be taken from a patient, a donor or from any other source, infected with a herpes simplex virus of the invention, optionally screened for expression and/or function of the encoded nitroreductase, and optionally returned/introduced to a patient's body, e.g. by injection.

Delivery of herpes simplex viruses of the invention to the selected cells may be performed using naked virus or by encapsulation of the virus in a carrier, e.g. nanoparticles, liposomes or other vesicles.

In vitro cultured cells, preferably human or mammalian cells, transformed with viruses of the present invention and preferably cells expressing the nitroreductase protein as well as methods of transforming such cells in vitro with said viruses form further aspects of the present invention.

In this specification, a mutant herpes simplex virus is a non-wild type herpes simplex virus and may be a recombinant herpes simplex virus. Mutant herpes simplex viruses may comprise a genome containing modifications relative to the wild type. A modification may include at least one deletion, insertion, addition or substitution.

Medicaments and pharmaceutical compositions according to aspects of the present invention may be formulated for administration by a number of routes, including but not limited to, parenteral, intravenous, intramuscular, intratumoural, oral and nasal. The medicaments and compositions may be formulated in fluid or solid (e.g. tablet) form. Fluid formulations may be formulated for administration by injection to a selected region of the human or animal body.

In this specification, non-neurovirulence is defined by the ability to introduce a high titre of virus (approx $10^6$ plaque forming units (pfu)) to an animal or patient[22, 23] without causing a lethal encephalitis such that the $LD_{50}$ in animals, e.g. mice, or human patients is in the approximate range of $\geq 10^6$ pfu[21].

Where all copies of the ICP34.5 gene present in the herpes simplex virus genome (two copies are normally present) are disrupted such that the herpes simplex virus is incapable of producing a functional ICP34.5 gene product, the virus is considered to be an ICP34.5 null mutant.

A regulatory sequence (e.g. promoter) that is operably linked to a nucleotide sequence may be located adjacent to that sequence or in close proximity such that the regulatory sequence can effect and/or control expression of a product of the nucleotide sequence. The encoded product of the nucleotide sequence may therefore be expressible from that regulatory sequence.

NTR Prodrug

In this specification, "NTR prodrug" means any chemical compound or agent which is not toxic, or exhibits low toxicity, to a selected human or animal body, or to selected cells or tissues of the human or animal body, and which may be activated by a nitroreducase enzyme to a chemical compound or agent which is cytotoxic to the human or animal body or to those selected cells.

"Activation" may involve conversion of a non-toxic (or low toxicity) prodrug to an active cytotoxic form. That conversion may involve enzymatic reduction of the prodrug by NTR. The enzymatic reduction reaction may involve the prodrug as a substrate for NTR and may involve other co-factors.

Examples of NTR prodrugs may include compounds from the following classes of molecules:
1. dinitirobenzamides;
2. dinitroaziridinylbenzamides (e.g. CB1954);
3. dinitrobenzamide mustard derivatives (e.g. SN23862);
4. 4-nitrobenzylcarbamates;
5. nitroindolines;
6. nitroaromatics that are substrates of NTR and are activated to release a cytotoxic phosphoramide mustard or like-reactive species upon NTR-reduction (also called nitroaryl phosphoramides)[17];
7. nitroaromatic prodrugs of the dinitrobenzamide class.

Examples of NTR prodrugs are disclosed in references 16 and 17 which are incorporated herein in their entirety by reference.

Nitroreductase (NTR)

Nitroreductase enzymes commonly catalyze the reduction of nitro compounds, quinones, and dyes. The enzymatic reduction may involve the co-factor NADPH.

In this specification nitroreductase (NTR) refers to an enzyme capable of activating an NTR prodrug to an active cytotoxic form.

Preferred NTR's may have the ability to reduce a wide range of nitro-containing compounds such as nitrofurazone (to the hydroxylamines) and quinones such as menadione (to the quinols).

Preferred NTR's may be specifically inhibited by the irreversible inhibitor dicoumarol.

One preferred NTR is the $E.$ $coli$ oxygen insensitive nitroreductase enzyme (the nfsB gene product). Sequence information for $E.$ $coli$ NTR can be found at the NCBI database (http://www.ncbi.nlm.nih.gov/) under accession numbers BA000007 (GI:47118301)—$E.$ $coli$ complete genome sequence—and BAB34039 (GI:13360074)—nitroreductase sequence information.

The amino acid sequence for the $E.$ $coli$ NTR protein (SEQ ID No. 1) and polynucleotide sequence for the $E.$ $coli$ NTR gene (SEQ ID No. 2) are reproduced at FIG. 32 (A) and (B) respectively.

The nucleotide and amino acid sequences of suitable nitroreductase enzymes may be derived or obtained from any animal, insect or microorganism including humans, non-human mammals and bacteria and may be selected from those sequences which are publicly available. Many sequences for other nitroreductase genes are publicly available. Examples of other nitroreductase nucleic acid sequences which may form part of a herpes simplex virus according to the present invention include the following which are referred to by their accession number for the NCBI database (www.ncbi.nlm.nih.gov):

BAB34039 (GI:13360074)—$E.$ $coli$
BAA35218.1 (GI:1651240)—$E.$ $coli$
AAB72053.1 (GI:2415385)—$B.$ $subtilis.$ Hybridisation Stringency In accordance with the present invention, nucleic acid sequences may be identified by using hybridization and washing conditions of appropriate stringency.

Complementary nucleic acid sequences will hybridise to one another through Watson-Crick binding interactions. Sequences which are not 100% complementary may also hybridise but the strength of the hybridisation usually decreases with the decrease in complementarity. The strength of hybridisation can therefore be used to distinguish the degree of complementarity of sequences capable of binding to each other.

The "stringency" of a hybridization reaction can be readily determined by a person skilled in the art.

The stringency of a given reaction may depend upon factors such as probe length, washing temperature, and salt concentration. Higher temperatures are generally required for proper annealing of long probes, while shorter probes may be annealed at lower temperatures. The higher the degree of desired complementarity between the probe and hybridisable sequence, the higher the relative temperature which can be used. As a result, it follows that higher relative temperatures would tend to make the reaction conditions more stringent, while lower temperatures less so.

For example, hybridizations may be performed, according to the method of Sambrook et al., ("Molecular Cloning, A Laboratory Manual, Cold Spring Harbor Laboratory Press, 1989) using a hybridization solution comprising: 5×SSC, 5×Denhardt's reagent, 0.5-1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42-65° C. in 1×SSC and 1% SDS, changing the solution every 30 minutes.

One common formula for calculating the stringency conditions required to achieve hybridization between nucleic acid molecules is to calculate the melting temperature $T_m$ (Sambrook et al., 1989):

$$T_m = 81.5° C. + 16.6 \text{ Log } [Na+] + 0.41(\% G+C) - 0.63(\% \text{ formamide}) - 600/n$$

where n is the number of bases in the oligonucleotide.

As an illustration of the above formula, using [Na+]=[0.368] and 50% formamide, with GC content of 42% and an average probe size of 200 bases, the $T_m$ is 57° C. The $T_m$ of a DNA duplex decreases by 1-1.5° C. with every 1% decrease in sequence complementarity.

Accordingly, nucleotide sequences can be categorised by an ability to hybridise to a target sequence under different hybridisation and washing stringency conditions which can be selected by using the above equation. The $T_m$ may be used to provide an indicator of the strength of the hybridisation.

The concept of distinguishing sequences based on the stringency of the conditions is well understood by the person skilled in the art and may be readily applied.

Sequences exhibiting 95-100% sequence complementarity may be considered to hybridise under very high stringency conditions, sequences exhibiting 85-95% complementarity may be considered to hybridise under high stringency conditions, sequences exhibiting 70-85% complementarity may be considered to hybridise under intermediate stringency conditions, sequences exhibiting 60-70% complementarity may be considered to hybridise under low stringency conditions and sequences exhibiting 50-60% complementarity may be considered to hybridise under very low stringency conditions.

The invention includes the combination of the aspects and preferred features described except where such a combination is clearly impermissible or expressly avoided.

Aspects and embodiments of the present invention will now be illustrated, by way of example, with reference to the accompanying figures. Further aspects and embodiments will

Clones 5 and 8 contained the pCMV-NAT-IRES-GFP-PolyA insert as two fragments of the predicted size—4.8 Kbp and 9.2 Kbp—were generated from AflII digestion. Clones without inserts would not be digested with AflII as there is no AflII site in RL1.del.

N.B. Inserts could have been cloned in two orientations, both of which were acceptable.

Figure 5:
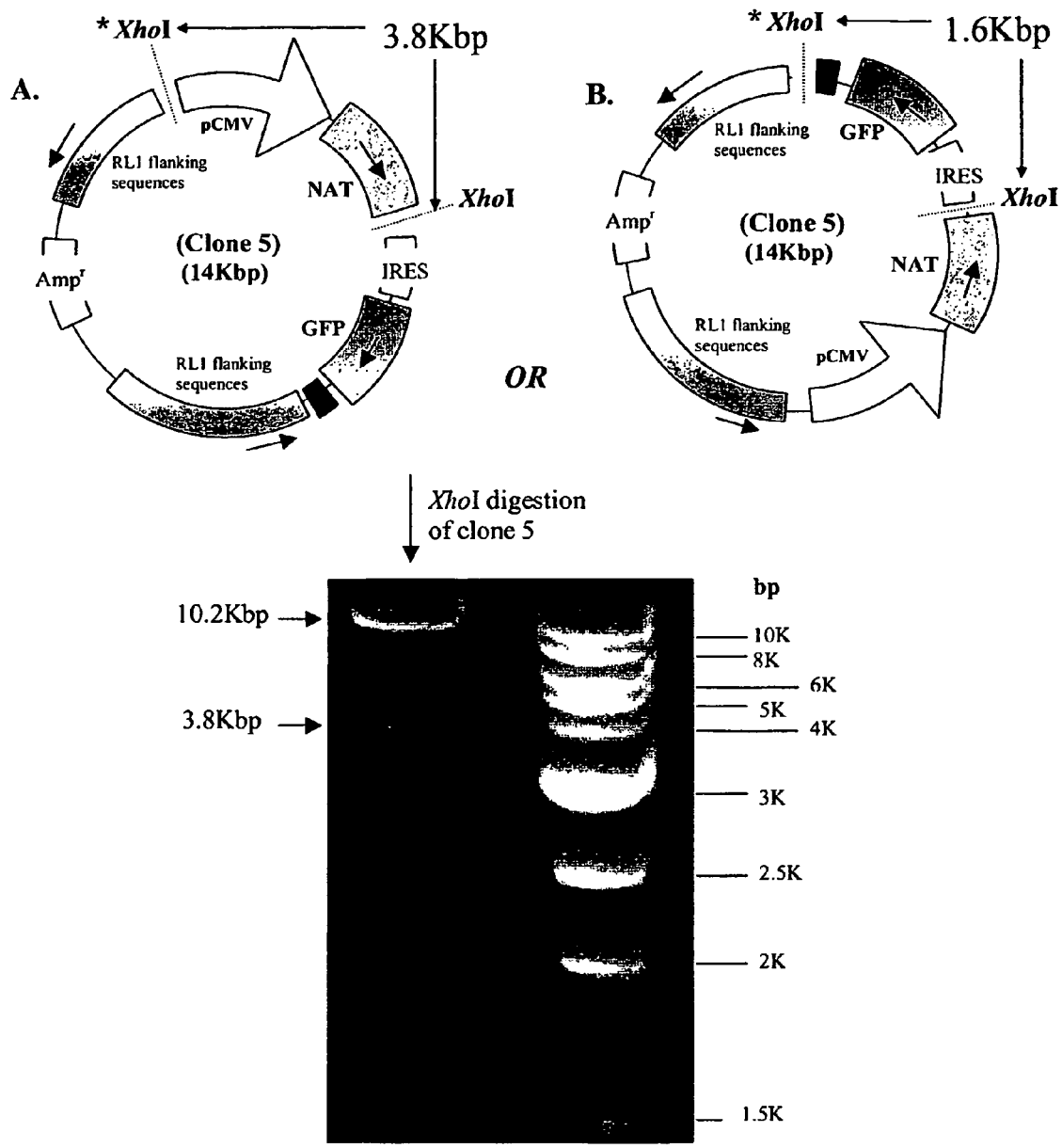

FIG. 5. Determination of the orientation of pCMV-NAT-IRES-GFP-PolyA in clone 5 (RL1.dCMV-NAT-GFPb). pCMV-NAT-IRES-GFP-PolyA (blunt ended) could have been cloned into the HpaI site of RL1.del in two orientations. To determine the orientation of the insert in clone 5, the plasmid was digested with XhoI and the digested DNA electrophoresed, beside a 1 Kbp DNA ladder (Promega), on a 1% agarose gel. If the insert had been cloned in the orientation shown in A, two fragments of 10.2 Kbp and 3.8 Kbp would be generated from XhoI digestion. If it had been cloned in the opposite orientation (B), two fragments of 12.4 Kbp and 1.6 Kbp would be generated. The presence of two fragments of 10.2 Kbp and 3.8 Kbp in the gel confirmed that the insert had been cloned in the orientation shown in A.

This XhoI site was present in the initial cloning vector (RL1.del), upstream of the HpaI site into which pCMV-NAT-IRES-GFP-PolyA was cloned.

Figure 6:
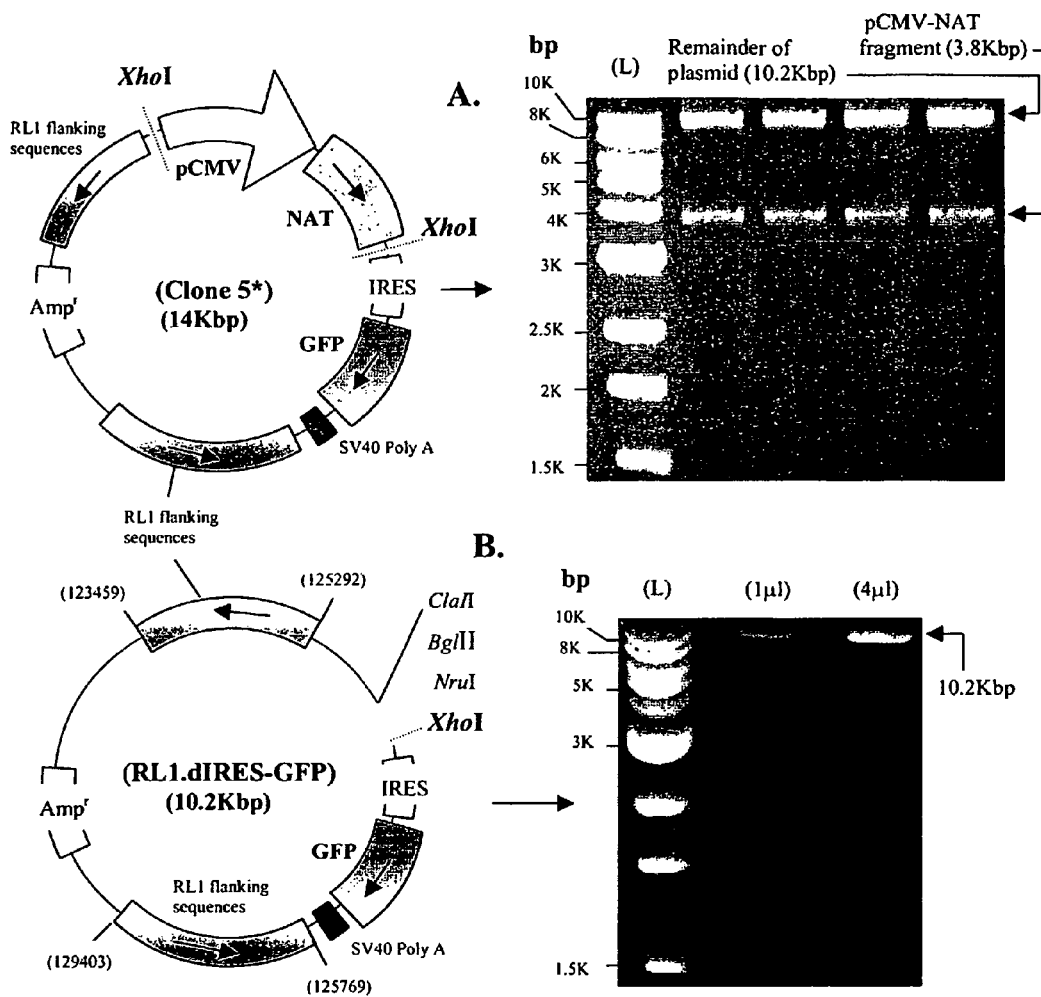

FIG. 6. Removal of pCMV-NAT from clone 5 (A) and large scale plasmid preparation of RL1.dIRES-GFP (B). Four samples of clone 5 were digested with XhoI and electrophoresed, beside a 1 Kbp DNA ladder (L) (Promega), on a 1% agarose gel (A). The larger fragment of DNA generated from this digestion (10.2 Kbp) was purified from the gel and ligated back together, at the XhoI sites, to form a single XhoI site in a new plasmid, designated RL1.dIRES-GFP. A large-scale plasmid preparation was grown up and the preparation checked by digesting with XhoI. 1 μl and 4 μl of the digested DNA was electrophoresed, beside a 1 Kbp DNA ladder (L) (Promega), on a 1% agarose gel (B). The DNA should produce a single fragment of 10.2 Kbp when digested with XhoI. The ClaI, BglII, NruI and XhoI sites of RL1.dIRES-GFP are all unique.

Clone 5 is the RL1.del plasmid into which has been cloned the 5.4 Kbp pCMV-NAT-IRES-GFP-PolyA fragment from pNAT-IRES-GFP.

Figure 7:
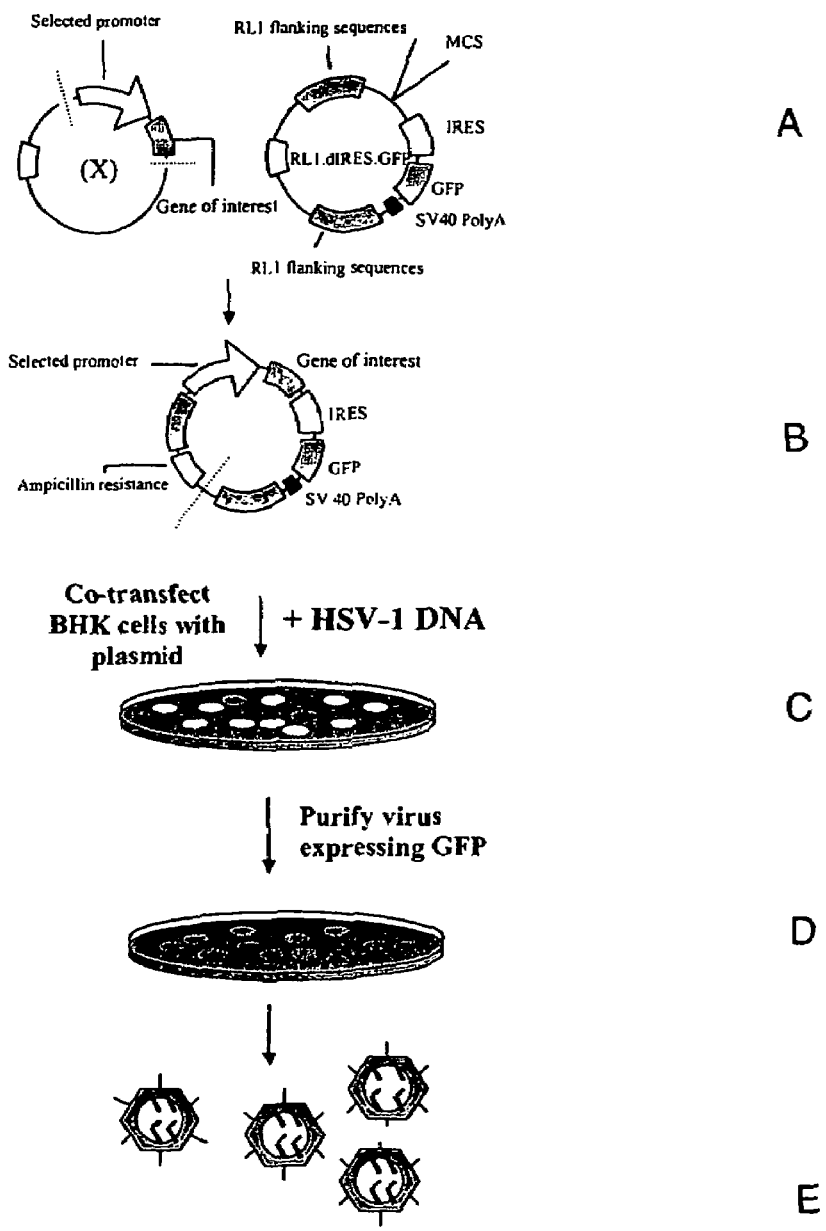

FIG. 7. Generation, detection and purification of ICP34.5 null HSV-1 expressing a gene product of interest.

Figure 8:
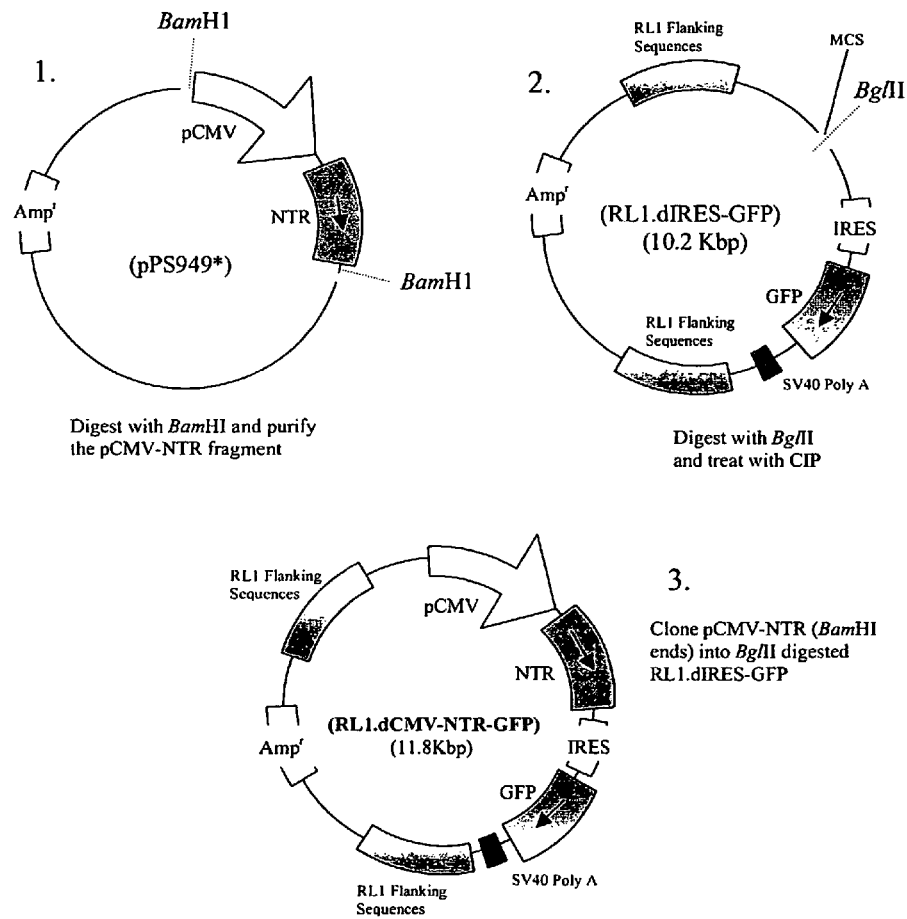

FIG. 8. Strategy used to clone pCMV-NTR from pPS949 into RL1.dIRES-GFP. (1) Digest pPS949 with BamHI and purify the 1.6 Kbp pCMV-NTR fragment; (2) Digest RL1.dIRES-GFP with BglII and treat with Calf Intestinal Phosphatase (CIP); (3) Clone the pCMV-NTR fragment (BamHI ends) into the BglII site of RL1.dIRES-GFP.

The pPS949 plasmid was a kind gift from Professor Lawrence Young (University of Birmingham) and contains the E. coli nitroreductase (NTR) gene downstream of the CMV-IE promoter (pCMV) in pLNCX (Clontech).

Figure 9:
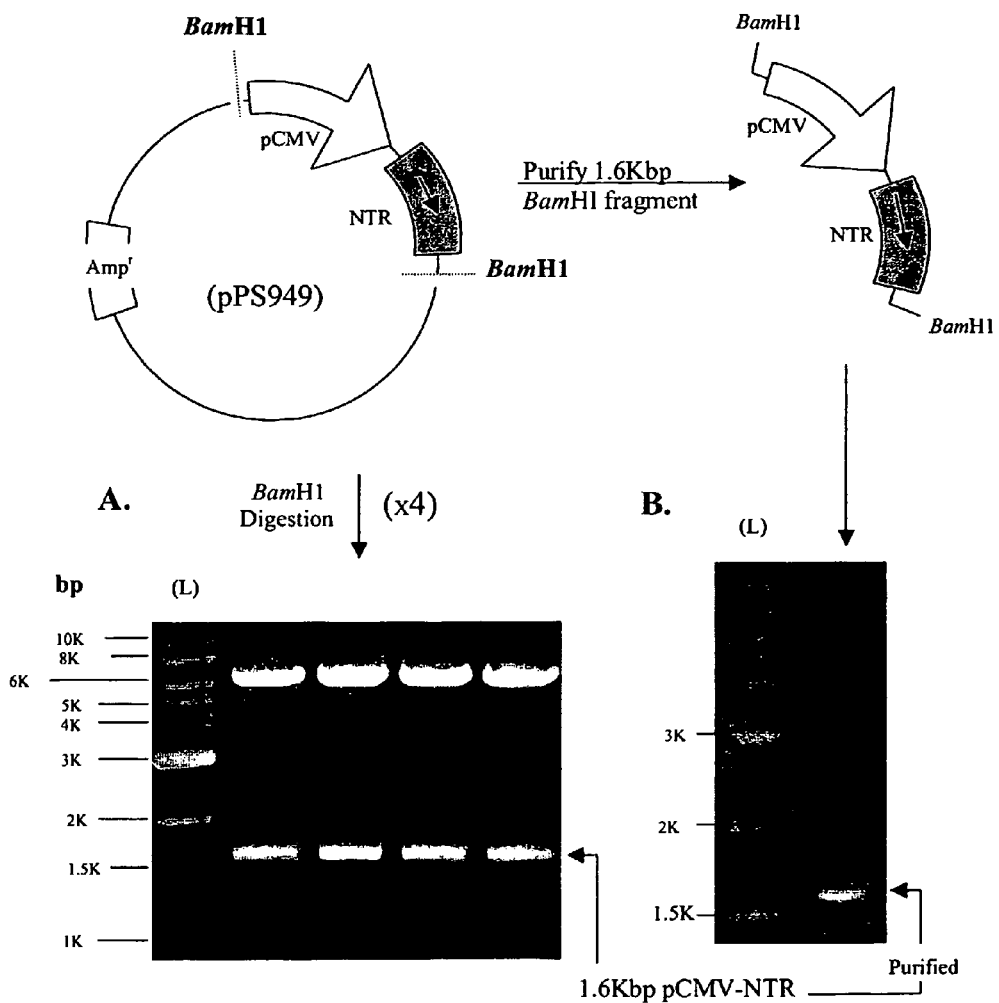

FIG. 9. Agarose gel electrophoresis of BamHI digested pPS949 (A) and the purified pCMV-NTR fragment (B). Four samples of pPS949 were digested with BamHI and electrophoresed, beside a 1 Kbp DNA ladder (L) (New England Biolabs), on a 1% agarose gel. The 1.6 Kbp fragments, consisting of the E. coli nitroreductase (NTR) gene downstream of the CMV IE promoter (pCMV), were purified from the gel and a sample of the purified DNA was electrophoresed on an agarose gel to check its concentration.

Figure 10:
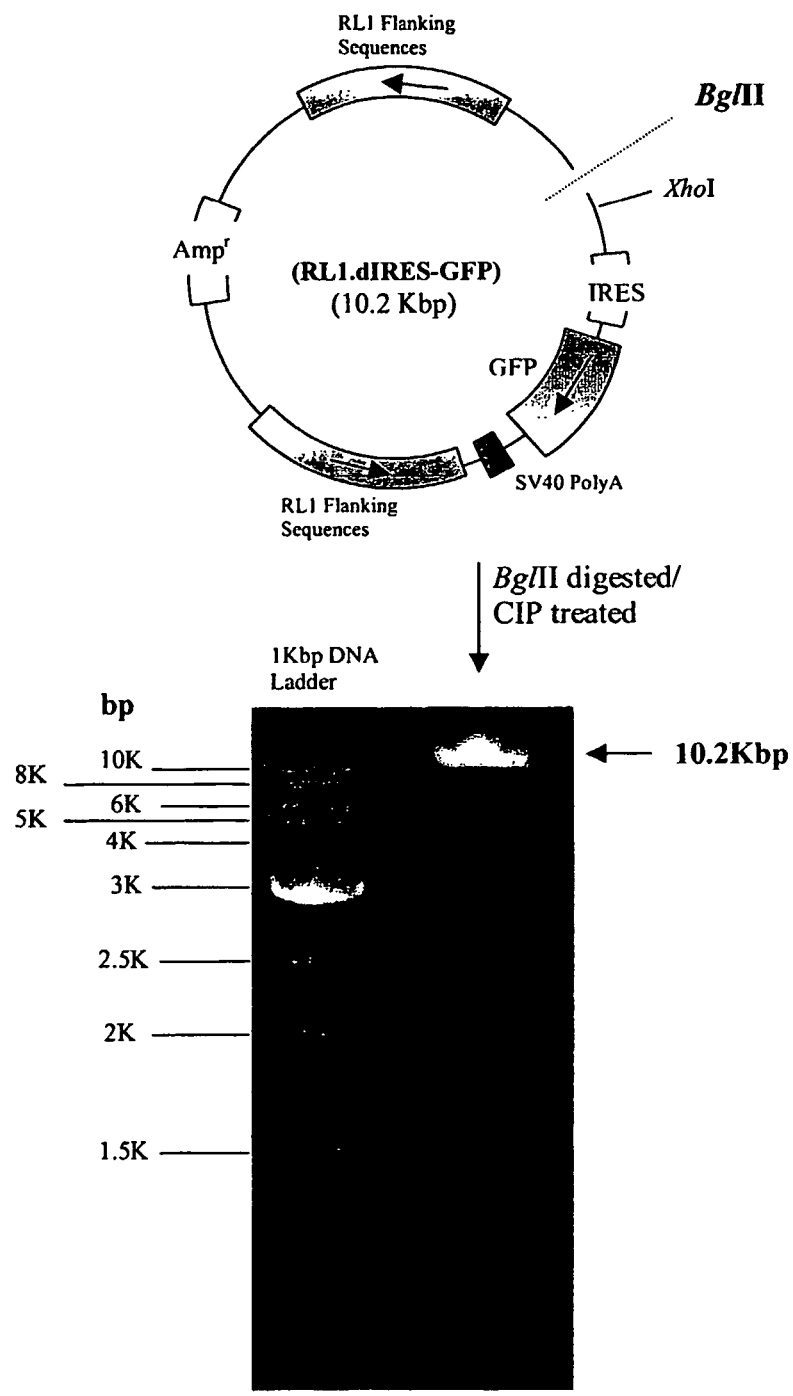

FIG. 10. Agarose gel electrophoresis of BglII digested, CIP treated RL1.dIRES-GFP. RL1.dIRES.GFP was digested with BglII. The digested plasmid was then treated with Calf Intestinal Phosphatase (CIP) to prevent the vector re-annealing to itself in subsequent ligation reactions. A sample of the digested/CIP treated DNA was electrophoresed, beside a 1 Kbp DNA ladder (Promega), on a 1% agarose gel to check its concentration. pCMV-NTR from pPS949 was subsequently cloned into this digested/CIP treated vector.

Figure 11:
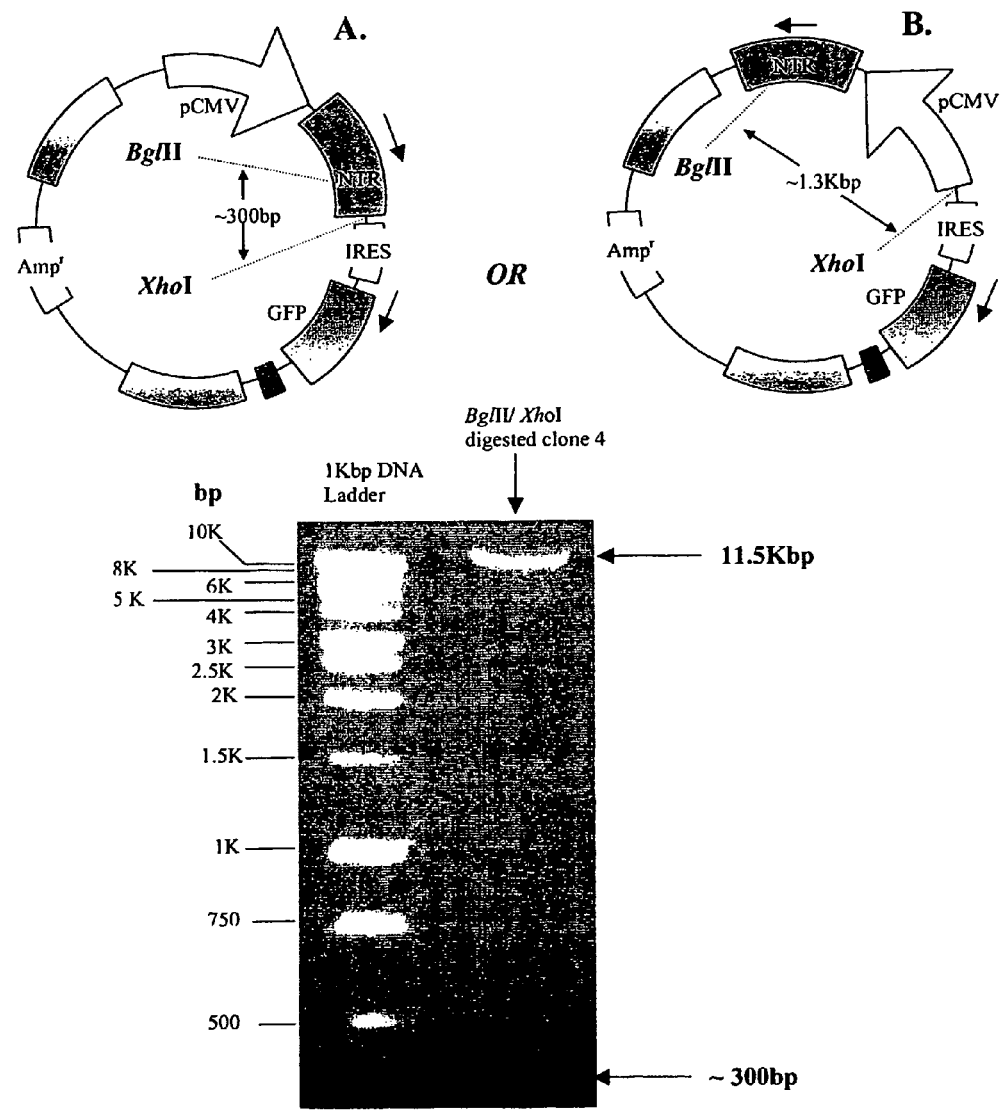

FIG. 11. Determination of the orientation of pCMV-NTR in clone 4. pCMV-NTR (BamHI ends) could have been cloned into the BglII site of RL1.dIRES-GFP in two orientations. To determine the orientation, clone 4 was digested with BglII and XhoI and the digested DNA electrophoresed, beside a 1 Kbp DNA ladder (Promega), on a 1% agarose gel. If the insert was in the desired orientation (A), two fragments (11.5 Kbp and 300 bp) would be generated. If in the opposite orientation, two fragments of 10.5 Kbp and 1.3 Kbp would be generated. The presence of a band at ~300 bp (and the absence of a band at 1.3 Kbp) confirmed that the pCMV-NTR fragment had been cloned into the vector in the desired orientation.

Figure 12:
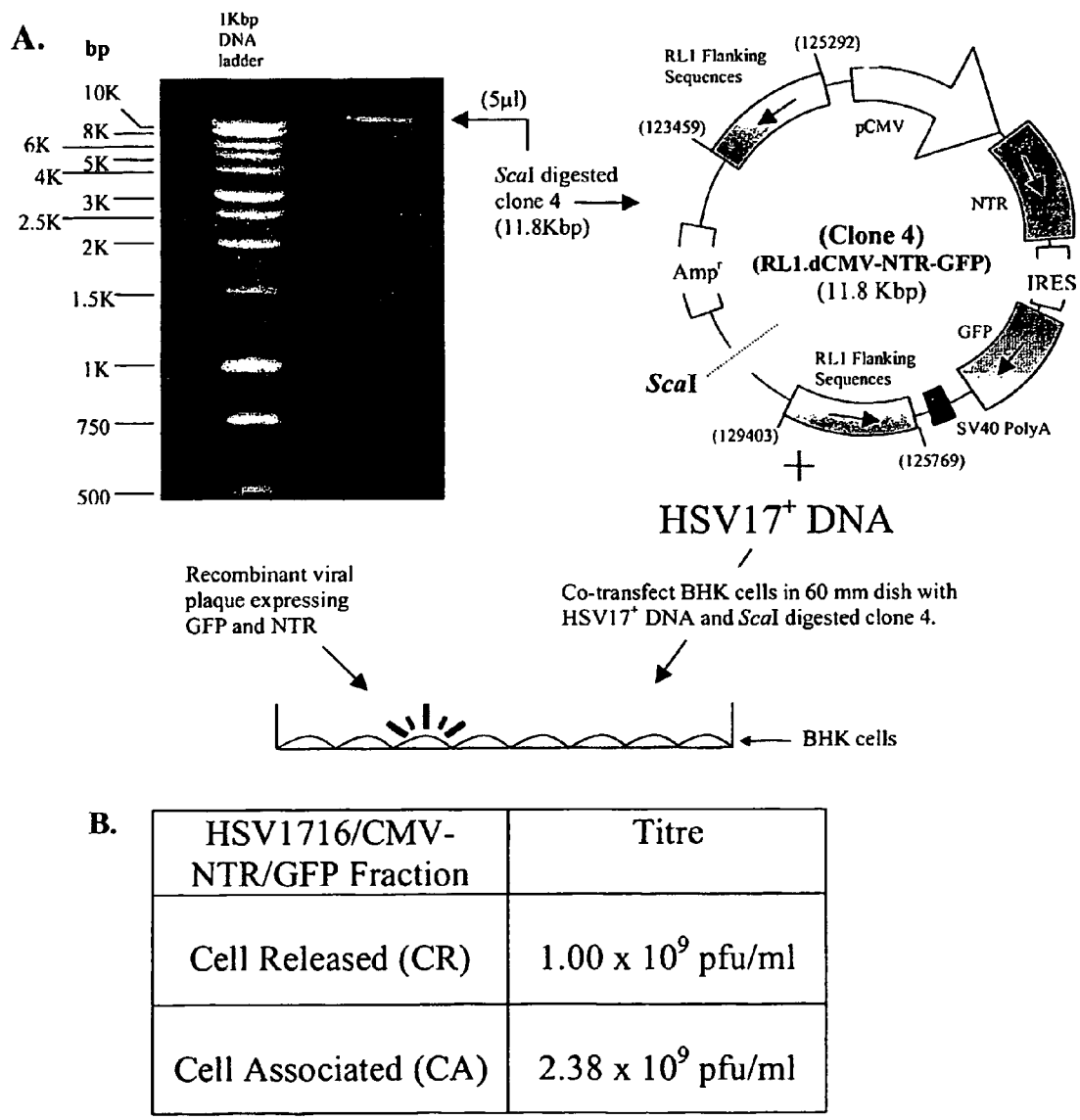

FIG. 12. Agarose gel electrophoresis of ScaI digested clone 4 (A) and HSV1716/CMV-NTR/GFP viral titres (B). Clone 4 (RL1.dCMV-NTR-GFP) was digested with ScaI, the digested DNA purified and 5 μl electrophoresed, beside a 1 Kbp DNA ladder (Promega), on a 1% agarose gel, to check its concentration. 80% confluent BHK cells were then co-transfected with 10 μl HSV17+ DNA and an appropriate volume of the remaining digested clone 4. The cells were incubated at 37° C. for 3 days until cpe was evident. Recombinant viral plaques were picked under the fluorescent microscope, purified and a virus stock, named HSV1716/CMV-NTR/GFP, grown up. The cell-associated and cell-released fraction of the virus stock was titrated on BHK cells.

Figure 13:
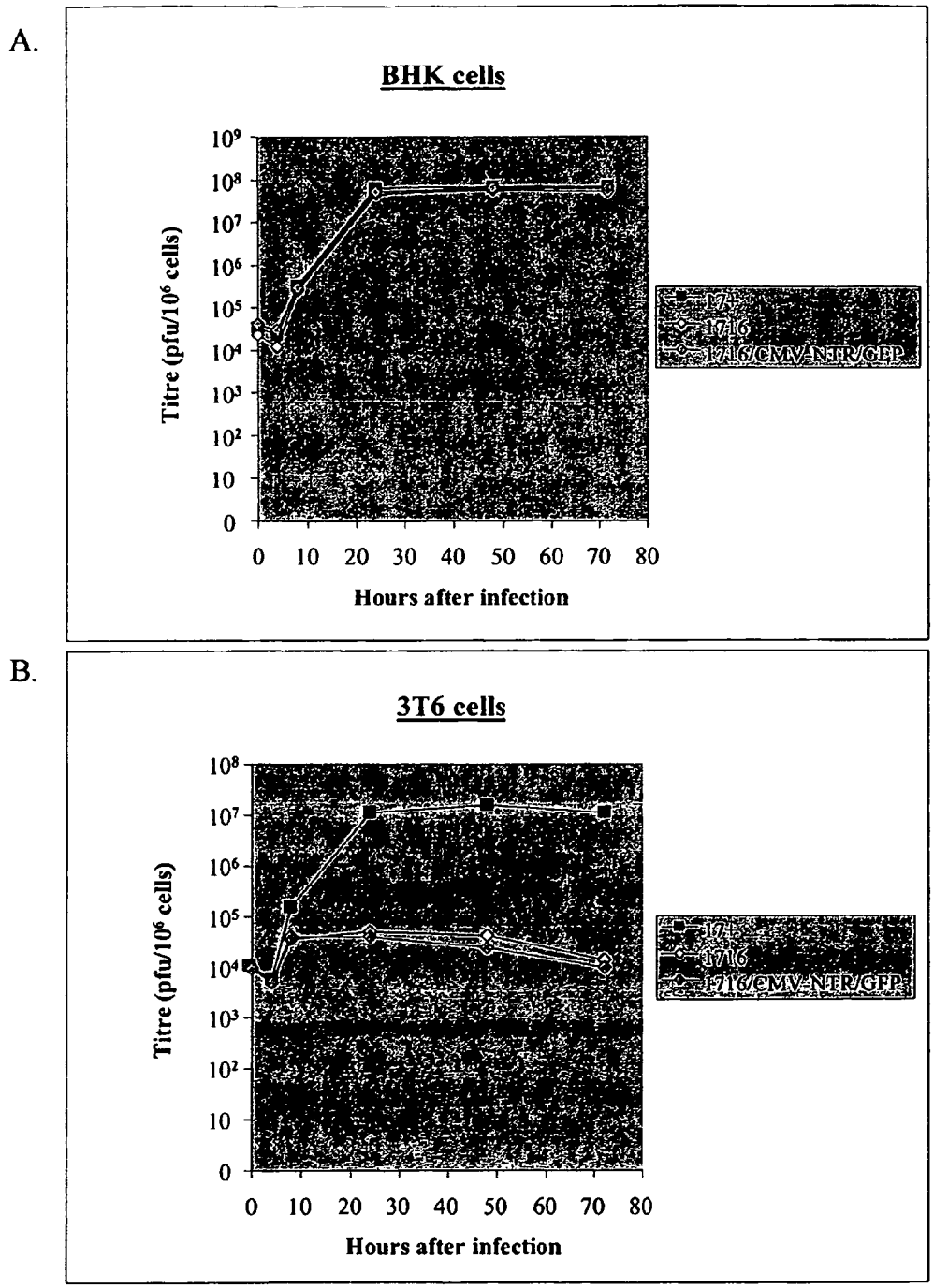

FIG. 13. Growth kinetics of HSV17$^+$, HSV1716 and HSV1716/CMV-NTR/GFP in confluent BHK and 3T6 cells. Confluent BHK and 3T6 cells were infected at a MOI of 0.1 pfu/cell. Infected cells were harvested at 0, 4, 24, 48 and 72 hrs post infection, sonicated and progeny virus titrated on BHK cell monolayers. All viruses replicated with similar kinetics in BHK cells (A); HSV1716 and HSV1716/CMV-NTR/GFP both failed to replicate efficiently in confluent 3T6 cells (B).

Figure 14:
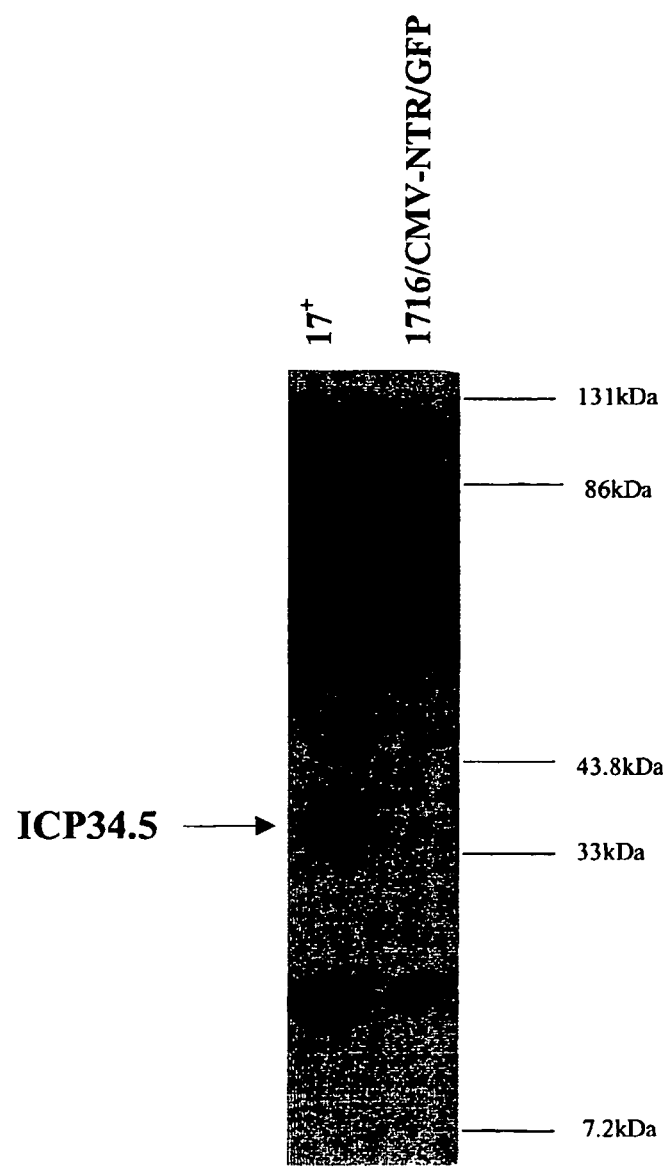

FIG. 14. Western blot analysis of ICP34.5 expression in HSV17+ and HSV1716/CMV-NTR/GFP infected BHK cells. BHK cells were infected with HSV17+ and HSV1716/CMV-NTR/GFP at a MOI of 10 pfu/cell. 16 hrs post infection, the cells were harvested and protein extracts analysed using 10% SDS-PAGE in a Western blot using a polyclonal anti-ICP34.5 antibody. ICP34.5 was strongly expressed in HSV17+ infected cells but was not expressed in HSV1716/CMV-NTR/GFP infected cells.

Figure 15:
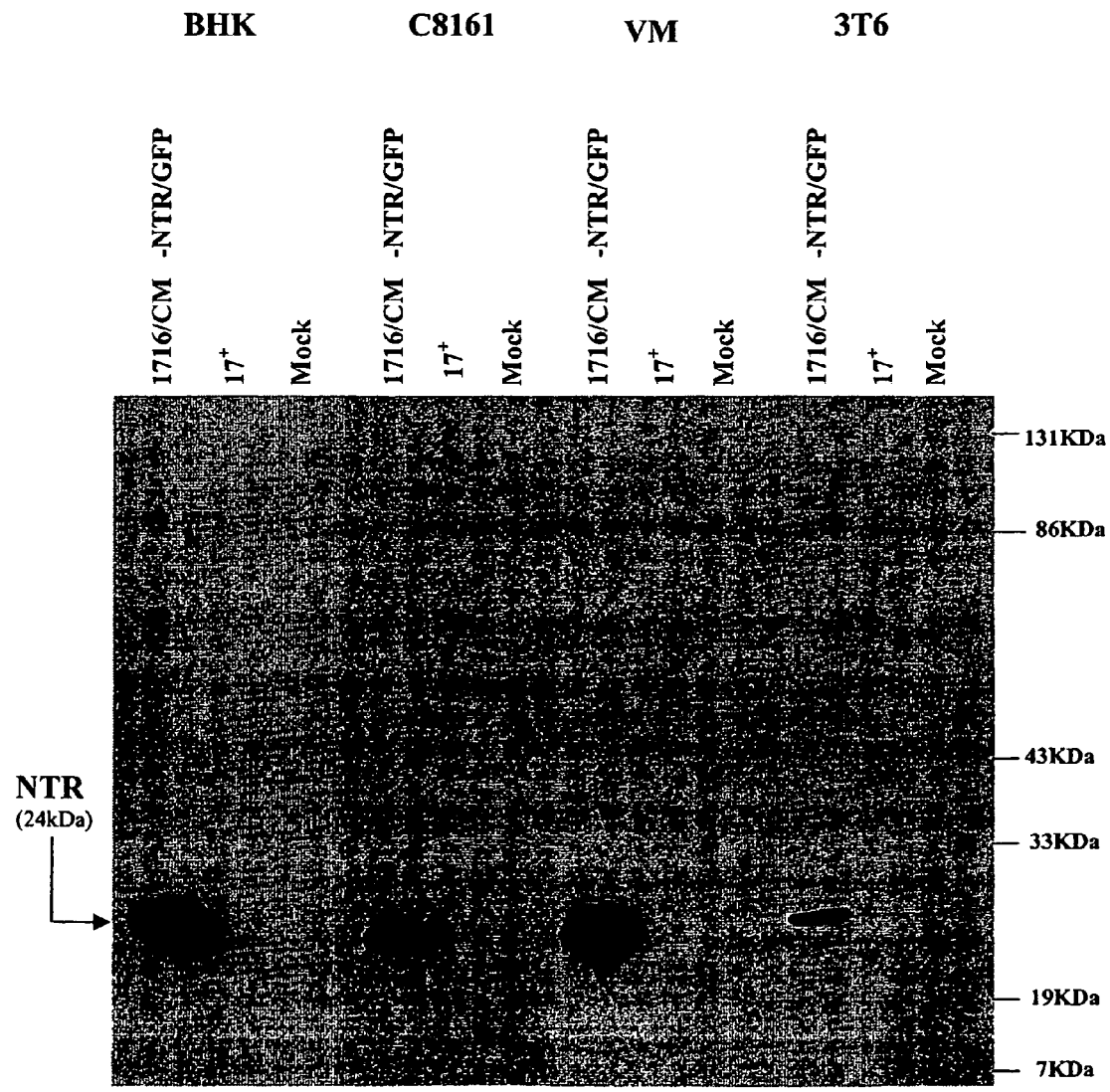

FIG. 15. Western blot analysis of NTR expression in HSV1716/CMV-NTR/GFP infected cell lines. BHK, C8161, VM and 3T6 cells were infected with 10 pfu/cell HSV1716/CMV-NTR/GFP, HSV17+ or mock infected. 16 hrs post infection, the cells were harvested and protein extracts analysed in a Western blot using a polyclonal NTR-specific antibody. Significant NTR expression was detected in all the HSV1716/CMV-NTR/GFP infected cells. No NTR expression was detected in the mock or HSV17+ infected cells.

Figure 16:
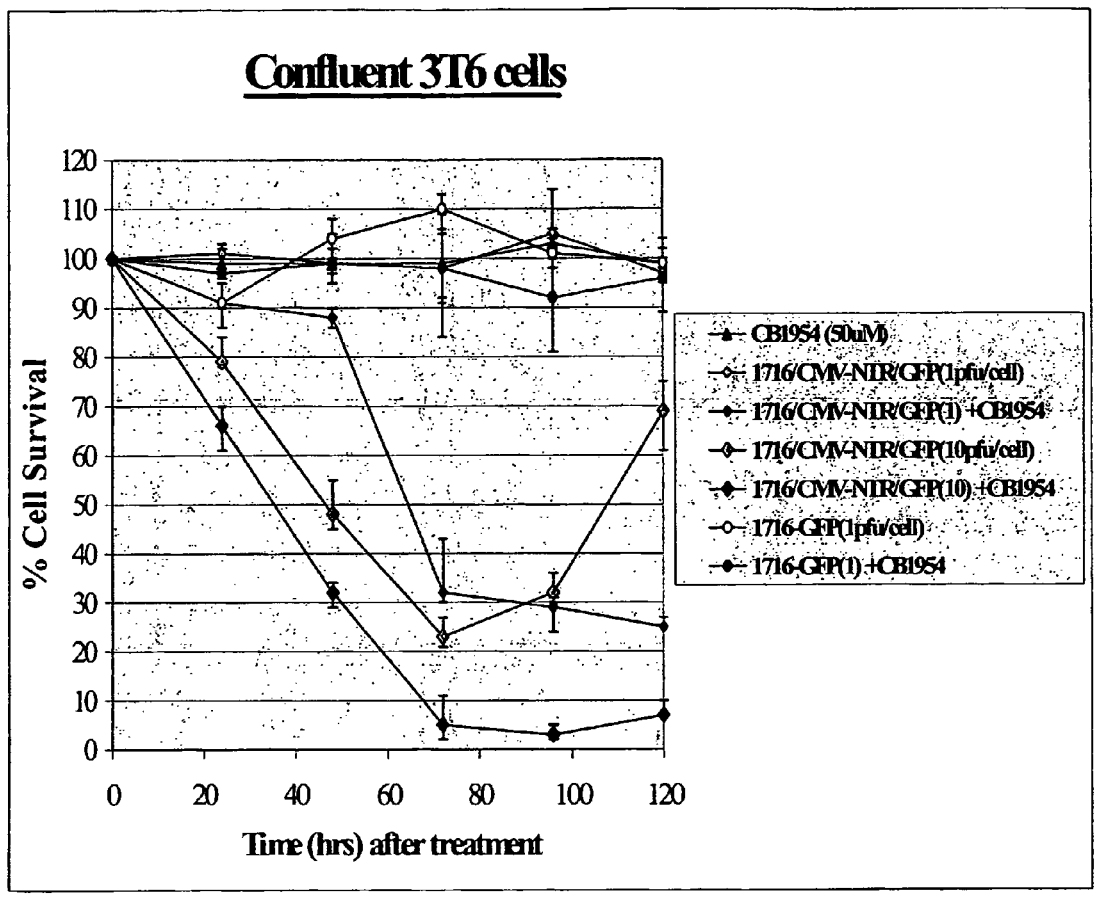

FIG. 16. Effect of HSV1716/CMV-NTR/GFP and HSV1716-GFP with or without CB1954 (50 µM) on confluent 3T6 cells. Confluent 3T6 cells in three wells of a 96-well plate were mock infected, infected with 1 or 10 pfu/cell HSV1716/CMV-NTR/GFP or infected with 1 pfu/cell of HSV1716-GFP. 45 minutes later, infected cells were overlaid with media containing 50 µM CB1954 or with media alone and incubated at 37° C. 24, 48, 72, 96, and 120 hrs later, % cell survival was determined relative to that of mock infected cells without prodrug using CellTiter 96 Aqueous One Solution Cell Proliferation Assay (Promega). Figures shown represent the mean of 3 values +/- standard error of the mean.

Figure 17:
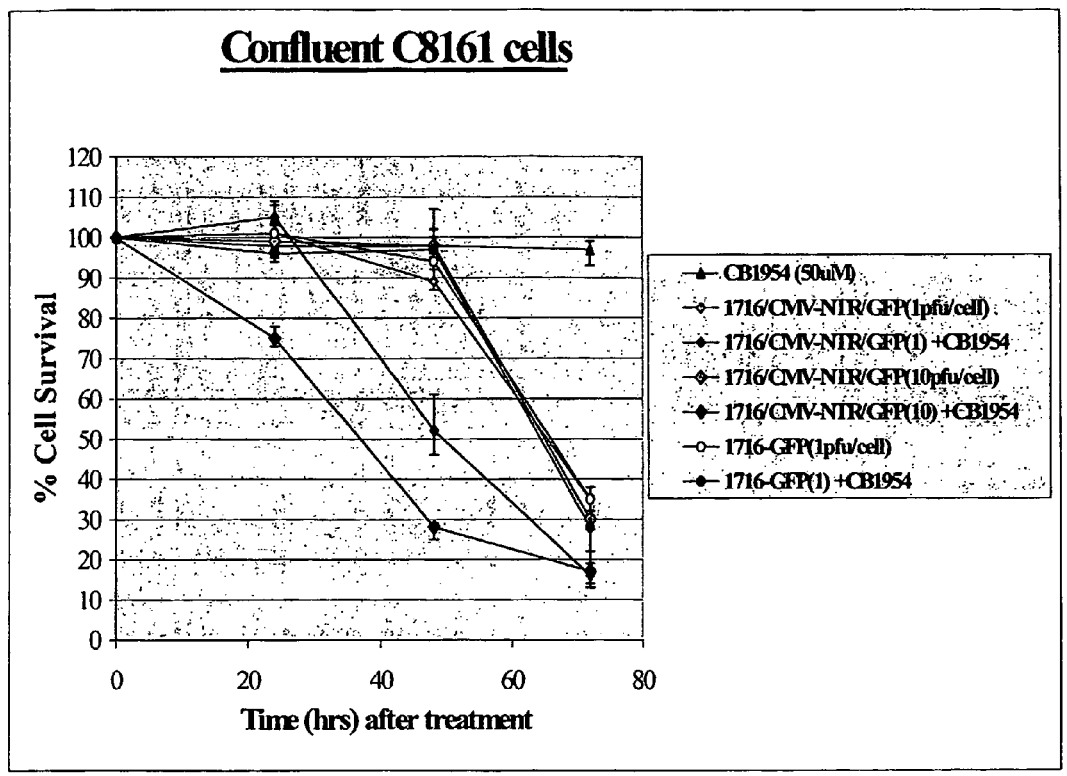

FIG. 17. Effect of HSV1716/CMV-NTR/GFP and HSV1716-GFP with or without CB1954 (50 µM) on confluent C8161 cells. Confluent C8161 cells in three wells of a 96-well plate were mock infected, infected with 1 or 10 pfu/cell HSV1716/CMV-NTR/GFP or infected with 1 pfu/cell of HSV1716-GFP. 45 minutes later, infected cells were overlaid with media containing 50 µM CB1954 or with media alone and incubated at 37° C. 24, 48 and 72 hrs later, % cell survival was determined relative to that of mock infected cells without prodrug using CellTiter 96 Aqueous One Solution Cell Proliferation Assay (Promega). Figures shown represent the mean of 3 values +/- standard error of the mean.

FIG. 18. Confluent 3T6 cells 72 hrs post treatment with 10 pfu/cell HSV1716/CMV-NTR/GFP (A), or 10 pfu/cell HSV1716/CMV-NTR/GFP with 50 µM CB1954 (B). The extent of cell death is significantly more pronounced in HSV1716/CMV-NTR/GFP infected cells overlaid with media containing 50 µM CB1954 than in HSV1716/CMV-NTR/GFP infected cells overlaid with normal media. The extent of cell death following infection of these cells with 10 pfu/cell HSV1716, with or without CB1954, is comparable to that seen in A (data not shown). 50 µM CB1954 alone has no effect on these cells.

FIG. 19. Confluent C8161 cells 72 hrs post treatment with 10 pfu/cell HSV1716/CMV-NTR/GFP (A), or 10 pfu/cell HSV1716/CMV-NTR/GFP with 50 µM CB1954 (B). The extent of cell death is significantly more pronounced in HSV1716/CMV-NTR/GFP infected cells overlaid with media containing 50 µM C1954 than in HSV1716/CMV-NTR/GFP infected cells overlaid with normal media. The extent of cell death following infection of these cells with 10 pfu/cell HSV1716, with or without CB1954, is comparable to that seen in A (data not shown). 50 µM CB1954 alone has no effect on these cells.

Figure 20:
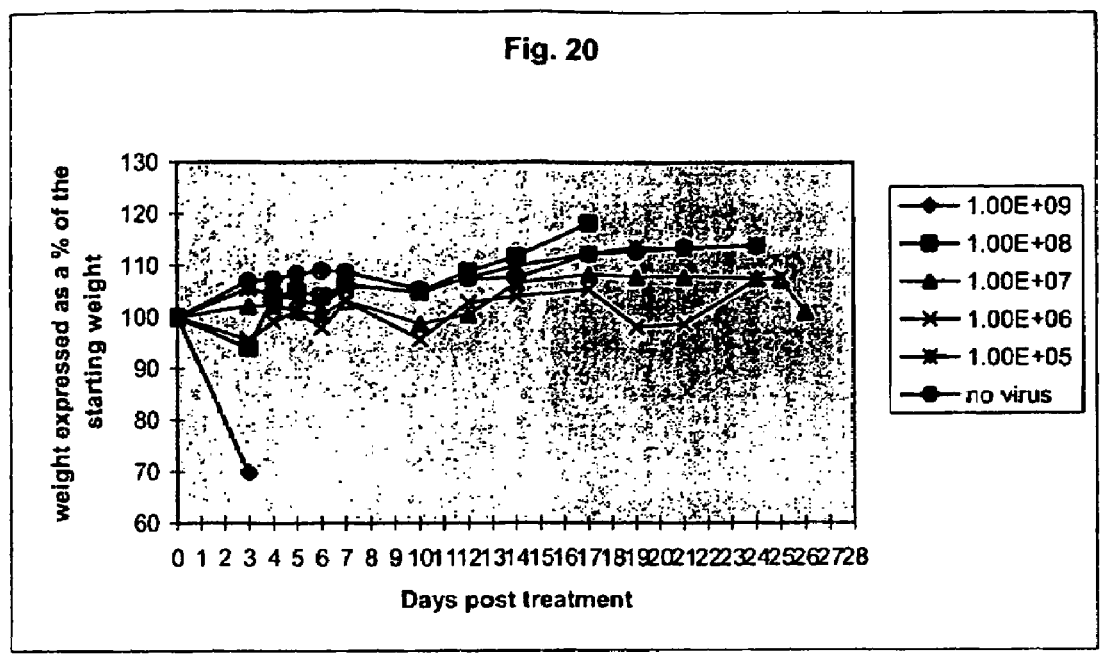

FIG. 20. Weight change (as a guide to health) in athymic nude mice with subcutaneous A2780 (xenograft) tumours injected intratumourally with HSV 1790. Group size=3 mice per dose. A2780 xenografts at date of intratumoural injection (Day 0) are between 0.5-1 mm in diameter. The xenografts have reached this size 12 days after injection with 10 million A2780 cells subcutaneously on the flank of female athymic nude mice.

Figure 21:
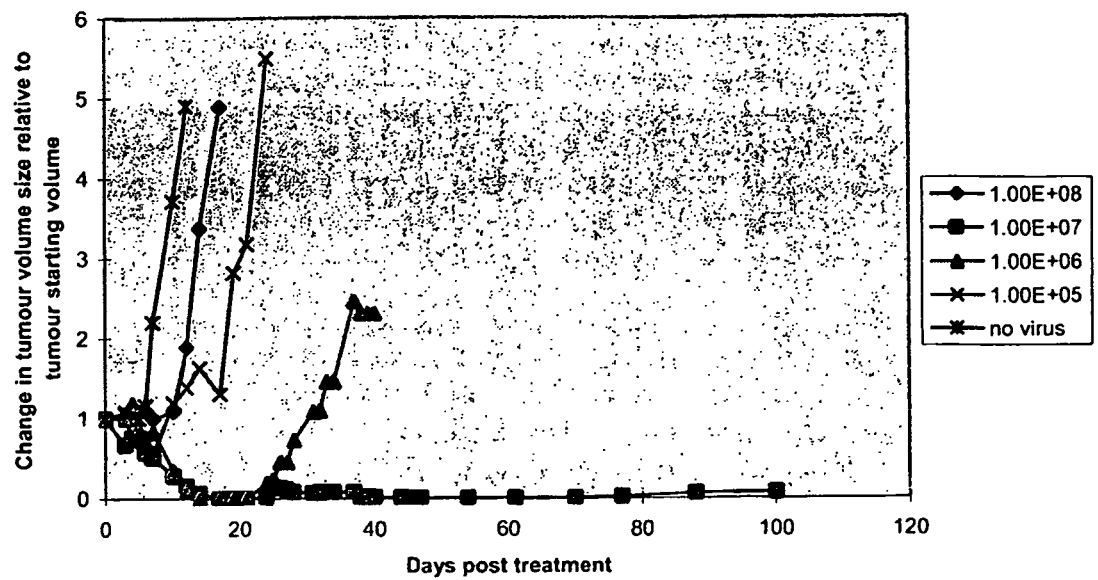

FIG. 21. Change in tumour volume over time in athymic nude mice with A2780 xenografts after intratumoural injection of HSV 1790.

Figure 22:
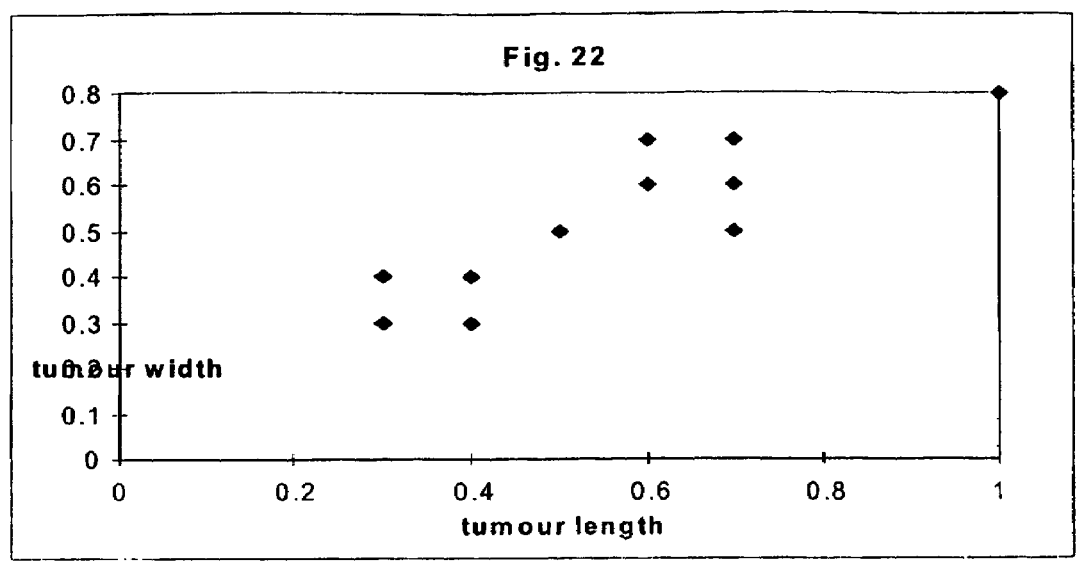

FIG. 22. Starting tumour sizes of mice.

Figure 23:
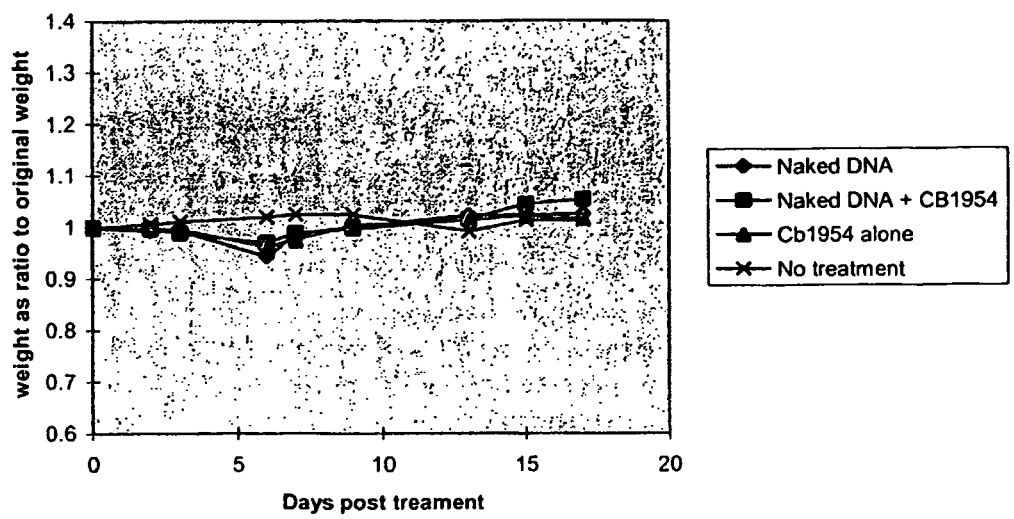

FIG. 23. Alterations in weight after treatment with CMV-ntr, CB1954 or a combination of both.

Figure 24:
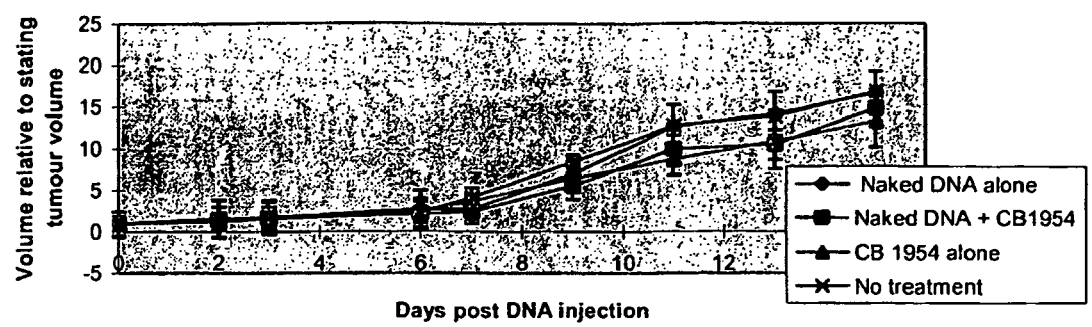

FIG. 24. Change in tumour volume after treatment with CMV-ntr, CB1954 or a combination of both.

Figure 25:
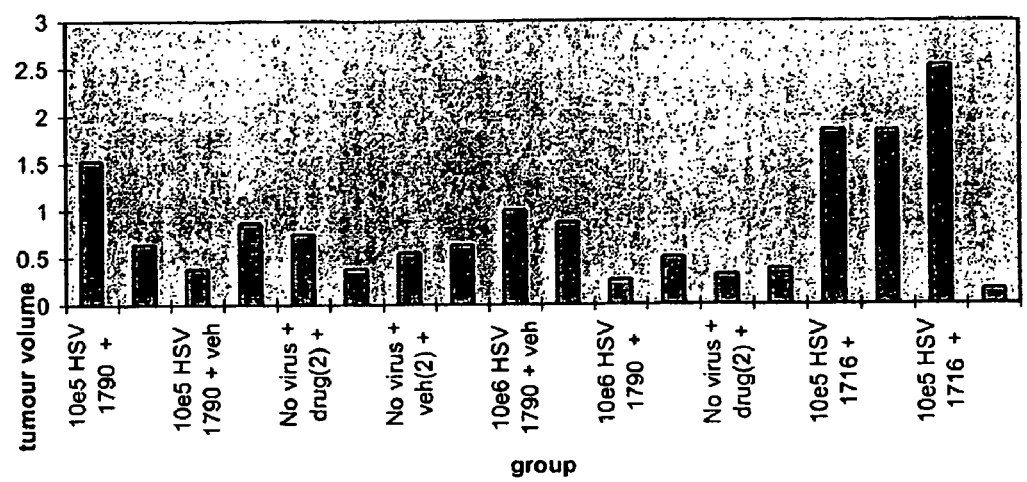

FIG. 25. Starting tumour volume of each treatment group (see Table 2).

Figure 26:
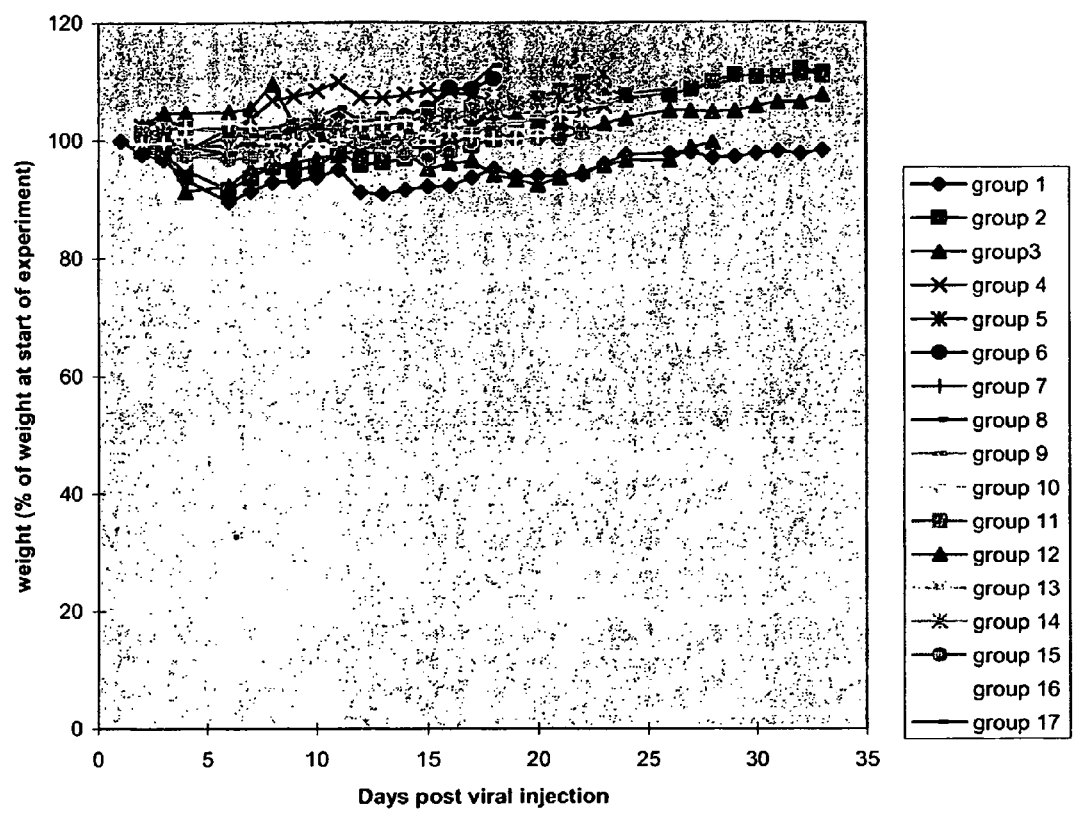

FIG. 26. Weight (as a measurement of health) in athymic nude mice with A2780 xenograft treated with either HSV 1790, HSV 1716, CB 1954 or a combination of them.

Figure 27:
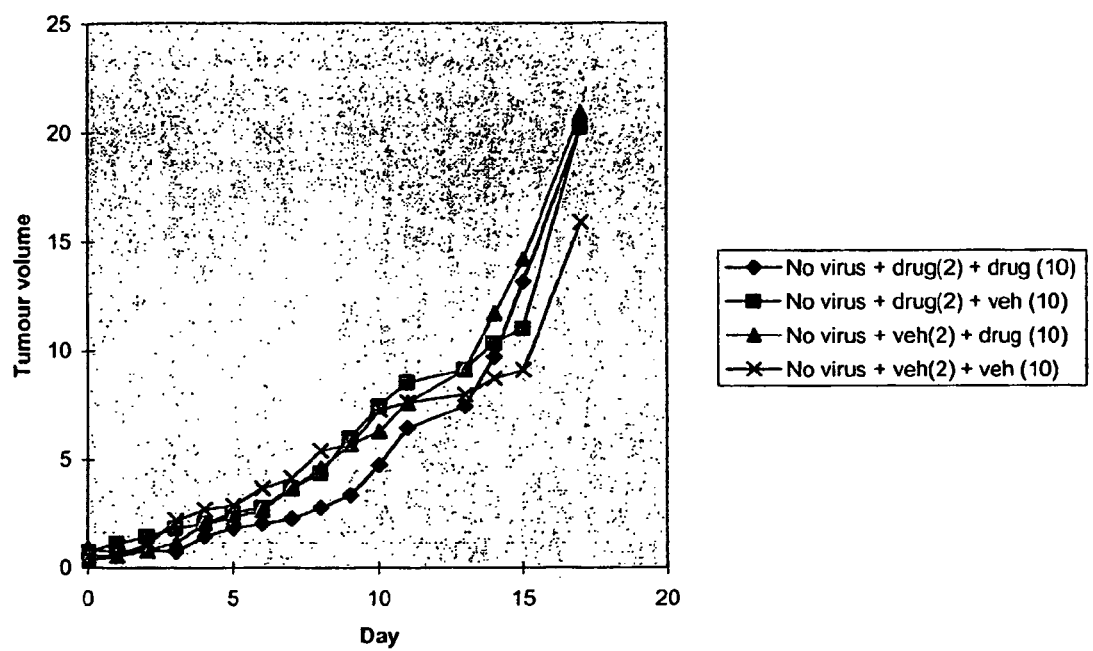

FIG. 27. Change in tumour volume of xenografts treated with the prodrug CB1954.

Figure 28:
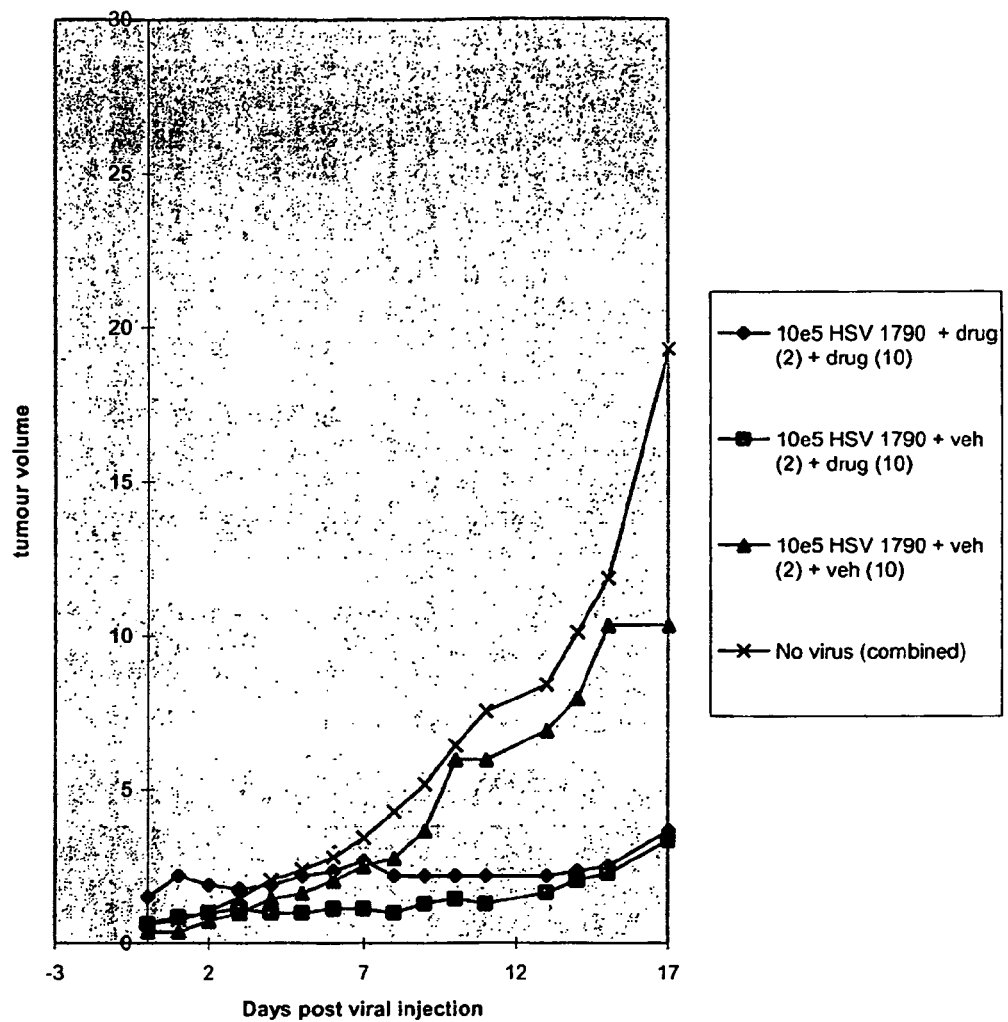

FIG. 28. Changes in tumour volume in xenograft treated with $10^5$ PFU HSV 1790 and CB1954.

Figure 29:
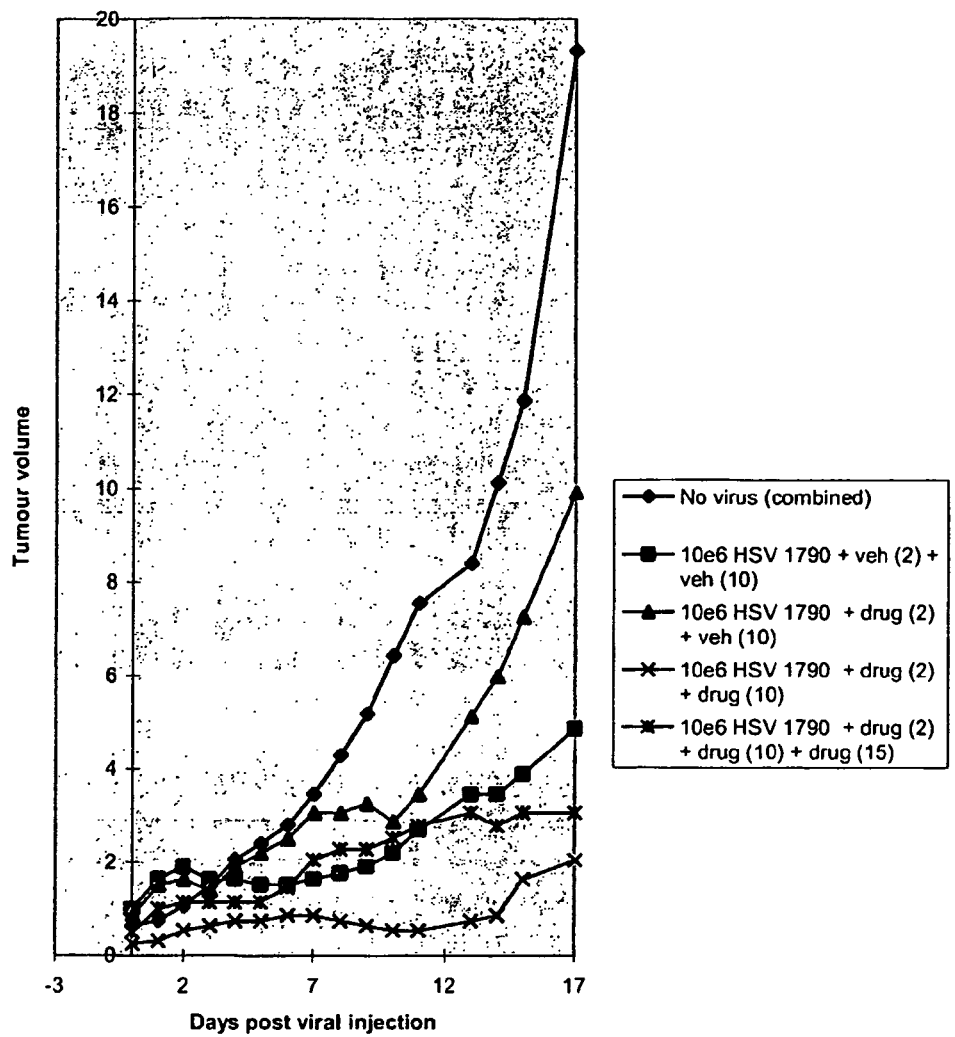

FIG. 29. Changes in tumour volume in xenografts treated with $10^6$ PFU HSV 1790 and CB1954.

Figure 30:
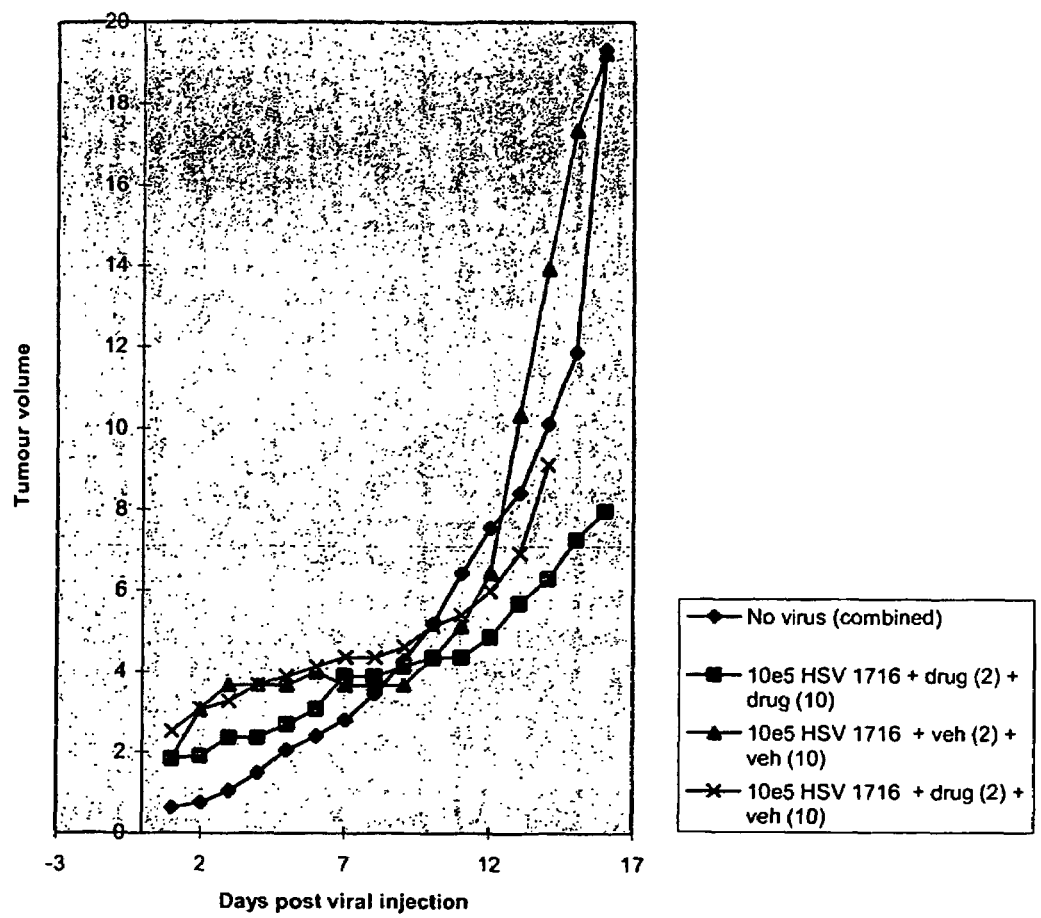

FIG. 30. Changes in tumour volume in xenografts treated with $10^5$ PFU HSV 1716 and CB1954.

Figure 31:
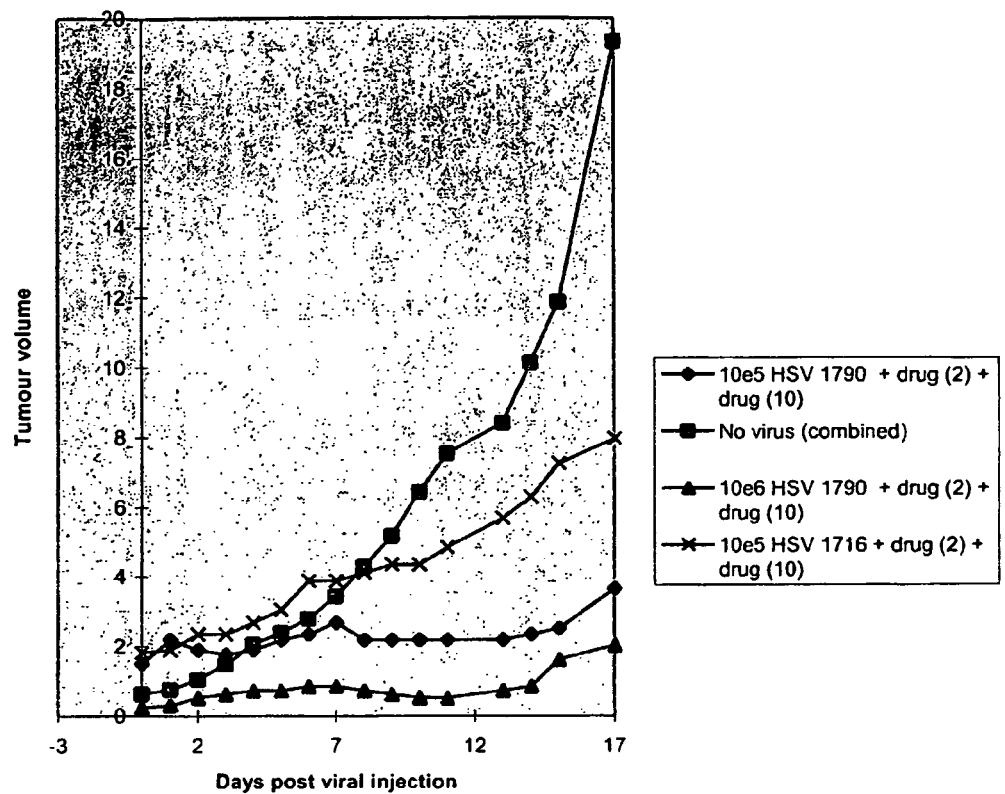

FIG. 31. Comparison of $10^5$ PFU, $10^6$ PFU HSV 1790 and $10^5$ PFU HSV 1716.

FIG. 32. Sequence information for *E. coli* NTR. (A) Amino acid sequence of NTR polypeptide (SEQ ID No. 1); (B) polynucleotide sequence for NTR gene (SEQ ID No. 2).

Figure 33A:
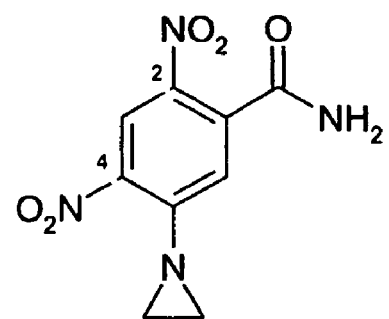
Figure 33B:
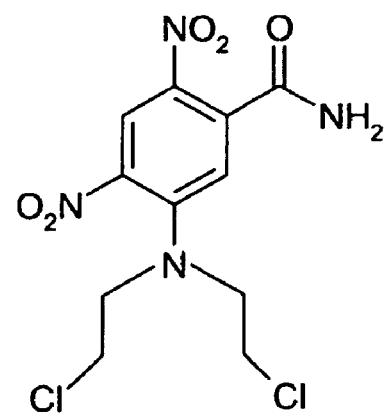

FIG. 33. Structure of two NTR prodrugs. (A) CB1954; (B) SN23862.

DETAILED DESCRIPTION OF THE BEST MODE OF THE INVENTION

Specific details of the best mode contemplated by the inventors for carrying out the invention are set forth below, by way of example. It will be apparent to one skilled in the art that the present invention may be practiced without limitation to these specific details.

Vectors Useful for Generation of Herpes Simplex Virus Mutants

Mutant herpes simplex viruses of the invention may be generated by use of nucleic acid vectors.

One such vector useful for generation of mutant herpes simplex viruses according to the present invention is a nucleic acid vector comprising, consisting or consisting essentially of:

first and second nucleotide sequences corresponding to nucleotide sequences flanking an insertion site in the genome of a selected herpes simplex virus; and a cassette located between said first and second nucleotide sequences comprising nucleic acid encoding:
  a) one or a plurality of insertion sites; and
  b) a ribosome binding site; and
  c) a marker.

Another vector useful for generation of mutant herpes simplex viruses according to the present invention is a nucleic acid vector comprising, consisting or consisting essentially of:

first and second nucleotide sequences corresponding to nucleotide sequences flanking an insertion site in the genome of a selected herpes simplex virus; and a cassette located between said first and second nucleotide sequences comprising nucleic acid encoding:

a) one or a plurality of insertion sites; and
b) a first regulatory nucleotide sequence; and
c) a marker.

The first and second nucleotide sequences may correspond to nucleotide sequences flanking an insertion site formed in, or comprising all or a part of, the ICP34.5 protein coding sequence of the genome of a selected herpes simplex virus.

The cassette may comprise a plurality of insertion sites, each insertion site preferably formed by nucleic acid encoding a specific restriction endonuclease site ('restriction site'). Together the restriction sites may form a multiple cloning site (MCS) comprising a series of overlapping or distinct restriction sites, preferably a series of distinct restriction sites comprising one or more of the ClaI, BglII, NruI, XhoI restriction sites.

The encoded components of the cassette may be arranged in a predetermined order. In one arrangement, the one or plurality of insertion sites is/are arranged upstream (i.e. 5') of the ribosome binding site/first regulatory sequence and the ribosome binding site/first regulatory sequence is arranged upstream (i.e. 5') of the marker.

The first and second nucleotide sequences may comprise nucleotide sequences having identity to regions of the genome surrounding the insertion site in the selected herpes simplex virus (the 'viral insertion site'). These sequences enable the cassette to be incorporated at the viral insertion site by homologous recombination between the first and second nucleotide sequences and their respective corresponding sequences in the viral genome.

Thus the first and second nucleotide sequences are flanking sequences for homologous recombination with corresponding sequences of a selected viral genome, such homologous recombination resulting in insertion of the cassette at the viral insertion site.

The first and second nucleotide sequences may correspond to nucleotide sequences flanking an insertion site in the RL1 locus of the HSV genome, more preferably in the ICP34.5 protein coding sequence of the HSV genome.

The first and second nucleotide sequences may each be at least 50 bp in length, more preferably at least 100, 150, 200, 300, 400, 500, 600, 700, 800, 900, 1000, 1100, 1200, 1300, 1400, 1500, 1600, 1700, 1800, 1900 2000, 2100, 2200, 2300, 2400, 2500, 2600, 2700, 2800, 2900, 3000, 3100, 3200, 3300, 3400, 3500, 3600, 3700, 3800, 3900 or 4000 bp in length. Each of the first and second nucleotide sequences may have at least 50% sequence identity to their corresponding sequence in the viral genome, more preferably at least 60%, 70%, 75%, 80%, 85%, 90%, 92%, 94%, 95%, 96%, 97%, 98% 99% or 100% identity. Identity of sequences is determined across the entire length of a given nucleotide sequence. Where sequences are of different length, sequence identity of the shorter sequence is determined over the entire length of the longer sequence.

The first and second nucleotide sequences may be characterised by the ability of one strand of a given sequence to hybridise with the corresponding single-stranded complement of the HSV genome under varying hybridisation stringency conditions. Suitably, the first and second nucleotide sequences will hybridise with their corresponding complement under very low, low or intermediate stringency conditions, more preferably at high or very high stringency conditions.

The viral insertion site is the position between the genomic nucleotide sequences corresponding to the first and second nucleotide sequences of the vector (the 'genomic' and 'vector flanking sequences' respectively) at which homologous recombination will occur and may be predetermined by selection of the vector flanking sequences. Where the genomic flanking sequences are immediately adjacent, the insertion site is the position between the peripheral and immediately adjacent bases of the two genomic flanking sequences, such that insertion of the cassette separates the genomic flanking sequences. Where the genomic flanking sequences are separated by one or a plurality of bases in the viral genome, the insertion site is formed by said one or a plurality of bases which are excised from the genome by the homologous recombination event.

The position of the viral insertion site may be accurately selected by careful selection and construction of the vector flanking sequences. Accordingly, the vector may be constructed such that homologous insertion of the cassette results in disruption of a chosen protein coding sequence and inactivation of the respective gene product or such that the cassette is inserted at a non-protein coding region of the viral genome. The complete genome sequences of several herpes simplex virus strains have been reported and are publicly available. The complete genome sequence for HSV-1 strain 17syn+ was reported by Dolan et al[3] (incorporated herein by reference) and the complete genome sequence of HSV-2 strain HG52 was reported by Dolan et al[4] (incorporated herein by reference) and is available from the EMBL database under accession code Z86099. Using this information, the vector of the present invention may preferably be designed for use in generating mutant HSV-1 (e.g. in strain 17 or F) or mutant HSV-2 (e.g. in strain HG52).

The first and second nucleotide sequences (vector flanking sequences) may each comprise sequence corresponding to the RL terminal repeat region of the genome of the selected HSV (e.g. HSV-1 strains 17 or F or HSV-2 strain HG52). The vector flanking sequences may comprise, consist or consist essentially of nucleotide sequences of the RL repeat region which flank the ICP34.5 protein coding sequence. In flanking the ICP34.5 coding sequence, one or both of the selected sequences may, in the corresponding HSV genome, overlap, i.e. extend into, the ICP34.5 protein coding sequence or one or both sequences may be selected so as to not overlap the ICP34.5 protein coding sequence. In a similar manner, the selected sequences may be chosen to overlap completely or partially other important encoded signals, e.g. transcription initiation site, polyadenylation site, defined promoters or enhancers. In this preferred arrangement the insertion site will thus comprise all or a part of the ICP34.5 protein coding sequence and/or be such that the inserted cassette disrupts the ICP34.5 protein coding sequence.

The vectors described, comprising first and second nucleotide sequences corresponding to regions of the RL repeat region flanking and/or overlapping the ICP34.5 protein coding sequence, may be used in the generation of ICP34.5 null mutants wherein all or a portion of the ICP34.5 protein coding sequence is excised and replaced during the homologous recombination event such that both copies of the ICP34.5 coding sequence are disrupted. The recombination may result in an insertion of nucleic acid within the ICP34.5 protein coding sequence thereby disrupting that sequence. In that case, successfully transformed virus are thus mutants incapable of generating the ICP34.5 active gene product from at least one copy, and preferably from both copies, of the ICP34.5 gene.

Successfully transformed virus are thus mutants incapable of generating the ICP34.5 active gene product.

Each component of the cassette may be positioned substantially adjacent the neighbouring component such that a single bicistronic transcript comprising or consisting essentially of the mRNA encoding the nucleotide sequence of interest, ribosome binding site and marker is obtainable.

The vectors described may further comprise, consist, or consist essentially of a nucleic acid encoding a selectable marker such as a polypeptide or protein conferring antibiotic resistance e.g. kanamycin resistance or ampicillin resistance.

The vectors described are preferably DNA vectors, particularly dsDNA vectors. The vector may be provided as a linear or circular (plasmid) DNA vector. The vector preferably contains nucleotide sequences, e.g. restriction endonuclease site(s), permitting transition between the two forms by use of DNA ligation and restriction materials (e.g. enzymes) and techniques known to the person skilled in the art. To achieve homologous recombination with a selected HSV, the vector is preferably provided in linear form.

One such vector provided by the inventors is plasmid RL1.dIRES-GFP deposited in the name of Crusade Laboratories Limited having an address at Department of Neurology Southern General Hospital 1345 Govan Road Govan Glasgow G51 5TF Scotland on 3 Sep. 2003 at the European Collection of Cell Cultures (ECACC), Health Protection Agency, Porton Down, Salisbury, Wiltshire, SP4 0JG, United Kingdom under accession number 03090303 in accordance with the provisions of the Budapest Treaty on the International Recognition of the Deposit of Microorganisms for the Purposes of Patent Procedure (herein referred to as the 'Budapest Treaty').

RL1.dIRES-GFP provides a platform for generating a plurality of 'shuttle vectors' which can exploit the process of homologous recombination to transfer a nucleotide sequence of interest (downstream of a selected promoter) into the disabling RL1 locus of HSV-1, generating easily identifiable, oncolytic, ICP34.5 null HSV-1 mutants expressing the products of the nucleotide sequence of interest, e.g. an RNA transcript or a polypeptide, and GFP. RL1.dIRES-GFP thus provides for ease of generation and purification of ICP34.5 null HSV.

RL1.dIRES-GFP is a useful vector for making second-generation oncolytic viruses having enhanced cytotoxic potential and which may express the product(s) of selected gene(s) to enhance the oncolytic and/or therapeutic effect of the administered virus.

The RL1.dIRES-GFP plasmid incorporates a multi-cloning sequence (MCS), upstream of an internal ribosome entry site (IRES), the GFP gene and SV40 polyadenylation sequences flanked by HSV-1 RL1 sequences. Incorporation of the encephalomyocarditis virus IRES (EMCV IRES) permits translation of two open reading frames from a single transcribed mRNA.

Following generation of a specific shuttle vector by cloning of the nucleotide sequence of interest (and the selected promoter) into RL1.dIRES-GFP, recombinant HSV-1 expressing the desired nucleic acid transcript or protein, can be generated and purified within 2 weeks. This compares with 2-3 months using prior art protocols.

In the ICP34.5 null HSV generated using the RL1.dIRES-GFP plasmid provided by the inventors transcription of both the nucleotide sequence of interest and GFP as a single transcript is controlled by the same promoter upstream of the nucleotide sequence of interest, the transcribed IRES directing cap-independent translation of GFP. The generated ICP34.5 null HSV are non-neurovirulent. By modifying the RL1.dIRES-GFP plasmid to incorporate appropriate flanking sequences surrounding the cassette other gene-specific HSV null mutants expressing GFP can be generated.

RL1.dIRES-GFP is promoterless, thus enabling a promoter of choice to be incorporated in the homologously recombined shuttle vector for controlling expression of the nucleotide sequence of interest from the inserted cassette.

Plasmid RL1.dIRES-GFP or modified plasmid shuttle vectors thereof further comprising nucleotide sequence encoding a nucleic acid transcript or polypeptide of interest may be provided in isolated or purified form.

The vector may be a variant of plasmid RL1.dIRES-GFP.

As the plasmid RL1.dIRES-GFP is designed for tandem expression of a sequence of interest and the marker gene encoding green fluorescent protein (GFP). The sequence of interest is cloned into RL1.dIRES-GFP along with its promoter (e.g. CMV) such that the promoter drives transcription of an mRNA for the sequence of interest along with the IRES-GFP. Translation results in expression of the GFP from the internal ribosomal entry site and the gene of interest and promoter must be cloned into RL1.dIRES-GFP in the correct orientation to achieve this. There are a number of instances where this tandem expression arrangement may be unsuitable and a variation of the cassette design is favourable.

One example is the expression of siRNAs as short hairpin RNAs using RNA polIII promoters such as H1 or U6. These promoters are unable to drive the additional tandem expression of the IRES-GFP as the RNApolIII expression cassette is designed only to produce short transcripts.

Additionally, sequences of interest derived from genomic DNA with strong mRNA shut-off signals in their 3' untranslated regions may not support IRES-GFP expression.

Thus in some cases a cassette may be provided in which the sequence of interest and marker are expressed separately from independent promoters.

One variant contains a cassette in which the ribosome binding site of plasmid RL1.dIRES-GFP is replaced with a regulatory nucleotide sequence, preferably a strong, constitutive promoter such as the Phosphoglycerokinase promoter. The marker is thereby expressed under the control of this (the 'first') regulatory sequence. The nucleotide sequence of interest (e.g. NTR, an antisense or siRNA) is expressed under the control of a second regulatory sequence upstream (5') of the nucleotide sequence of interest, e.g. the CMV promoter. This vector variant is particularly suitable for expression of siRNA where a weak promoter may be used for expression of the siRNA molecule or where the nucleic acid encoding the NTR may have a strong termination signal making it difficult to transcribe or translate a single bi- or poly-cistronic transcript encoding the NTR and marker sequence. In this arrangement the transformed virus containing the cassette integrated in the viral genome produces two separate transcripts under the control of the first and second promoters.

One such cassette was constructed in the following manner. The 1.3 kbp blunt-ended EcoRI/AflII fragment that contains the PGK promoter/GFP gene was obtained by restriction digestion followed by Klenow treatment from the vector pSNRG and cloned into the RL1-del vector cut with the restriction enzyme NruI that generates blunt ends. Successful insertion of the PGK/GFP DNA was confirmed by BamHI digestion and the orientation of the inserted DNA identified using the unique XhoI site in RL1-del and the BsrGI site at the 3' end of PGK/GFP. Plasmids with PGK/GFP in both forward and reverse orientation were obtained and the plasmids were designated RL1-dPGK/GFPfor and RL1-dPGK/GFPrev. Expression of GFP was confirmed in BHK cells transfected with the forward and reverse orientation plasmids.

Thus, sequences of interest along with their own promoters (although it is preferred that the PGK promoter is not also used for this purpose) can then be cloned into either RL1-dPGK/GFPfor or RL1-dPGK/GFPrev in either orientation using the remaining unique BglII, XhoI or HpaI unique restriction enzyme sites. The resulting plasmid can be used to derive recombinant HSV in which the marker GFP gene and the gene of interest are expressed independently from their own promoters.

The vectors described may be constructed for use in generating engineered HSV-1 or HSV-2 by insertion of a nucleic acid cassette through a mechanism of homologous recombination between nucleotide sequences flanking the cassette and corresponding sequences in the selected herpes simplex virus genome.

The vectors described may comprise and have use as:
i) gene delivery (gene therapy) vectors for delivery of a selected nucleotide sequence, e.g. NTR, to a specific locus of the HSV genome; and/or
ii) expression vectors for expression of the delivered nucleotide sequence of i) from the HSV genome under the control of a selected regulatory element; and/or
iii) vectors for the generation of HSV gene-specific null mutants wherein the cassette is inserted at a selected genomic location to disrupt the protein coding sequence of a selected HSV gene such that the gene product is inactive in the resultant mutant virus.

The vectors described may be used in the manufacture of engineered gene specific HSV null mutants, i.e. HSV mutants incapable of expressing an active gene product of a selected gene. They may be used in the manufacture of engineered viruses which express a selected protein from only one gene copy the other gene copy being disrupted or modified such that it cannot express a functional gene product. Such vectors may also be used in the manufacture of a medicament, preferably comprising said gene specific HSV null mutant, for use in treating cancer and tumours, preferably by the oncolytic treatment of the tumour.

The vectors described may also be used in the manufacture of engineered HSV mutants wherein the genome of the mutant HSV comprises an exogenous or heterologous gene which may have been inserted in the HSV genome by homologous recombination of the cassette. Preferably, the exogenous/heterologous gene is expressed in the mutant HSV, which expression may be regulated by a regulatory element, e.g. promoter, forming part of the inserted cassette. Such vectors may be used in the manufacture of a medicament, preferably comprising the engineered HSV mutant, for use in the treatment of disease, including the oncolytic treatment of tumours.

The vectors described may also be used in the manufacture of an engineered HSV mutant wherein the genome of the mutant HSV comprises an exogenous/heterologous gene (i.e. a non-HSV originating gene) which may have been inserted in a protein coding sequence of the HSV genome by homologous recombination of the cassette such that the mutant HSV is incapable of expressing the active gene encoded by said protein coding sequence and wherein the exogenous/heterologous gene product is expressed under the control of a regulatory element. Preferably, the regulatory element forms part of the cassette. Such vectors may be used in the manufacture of a medicament, preferably comprising the engineered HSV mutant, for use in the treatment of disease, including the oncolytic treatment of tumours.

The vectors described may also be used in the manufacture of an engineered HSV mutant wherein the genome of the mutant HSV comprises a nucleotide sequence which has been inserted in a protein coding sequence of the HSV genome by homologous recombination of the cassette such that the mutant HSV is incapable of expressing the active gene encoded by said protein coding sequence and wherein the inserted nucleotide sequence is expressed under the control of a regulatory element to produce a desired transcript. Preferably, the regulatory element forms part of the cassette. Such vectors may be used in the manufacture of a medicament, preferably comprising the engineered HSV mutant, for use in the treatment of disease, including the oncolytic treatment of tumours.

The vectors described may be used to generate mutant HSV by inserting the cassette into the genome of a selected HSV, the method of generation may comprise providing a vector described above, where the vector is a plasmid, linearising the vector; and co-transfecting a cell culture with the linearised vector and genomic DNA from said HSV.

The co-transfection may be carried out under conditions effective for homologous recombination of said cassette into an insertion site of the viral genome.

The method may further comprise one or more of the steps of:
1) screening said co-transfected cell culture to detect mutant HSV expressing said marker; and/or
2) isolating said mutant HSV; and/or
3) screening said mutant HSV for expression of the nucleotide sequence of interest or the RNA or polypeptide thereby encoded; and/or
4) screening said mutant HSV for lack of an active gene product; and/or
5) testing the oncolytic ability of said mutant HSV to kill tumour cells in vitro.

EXAMPLE 1

Construction of Plasmid RL1.dIRES-GFP

General Approach

Figure 1:
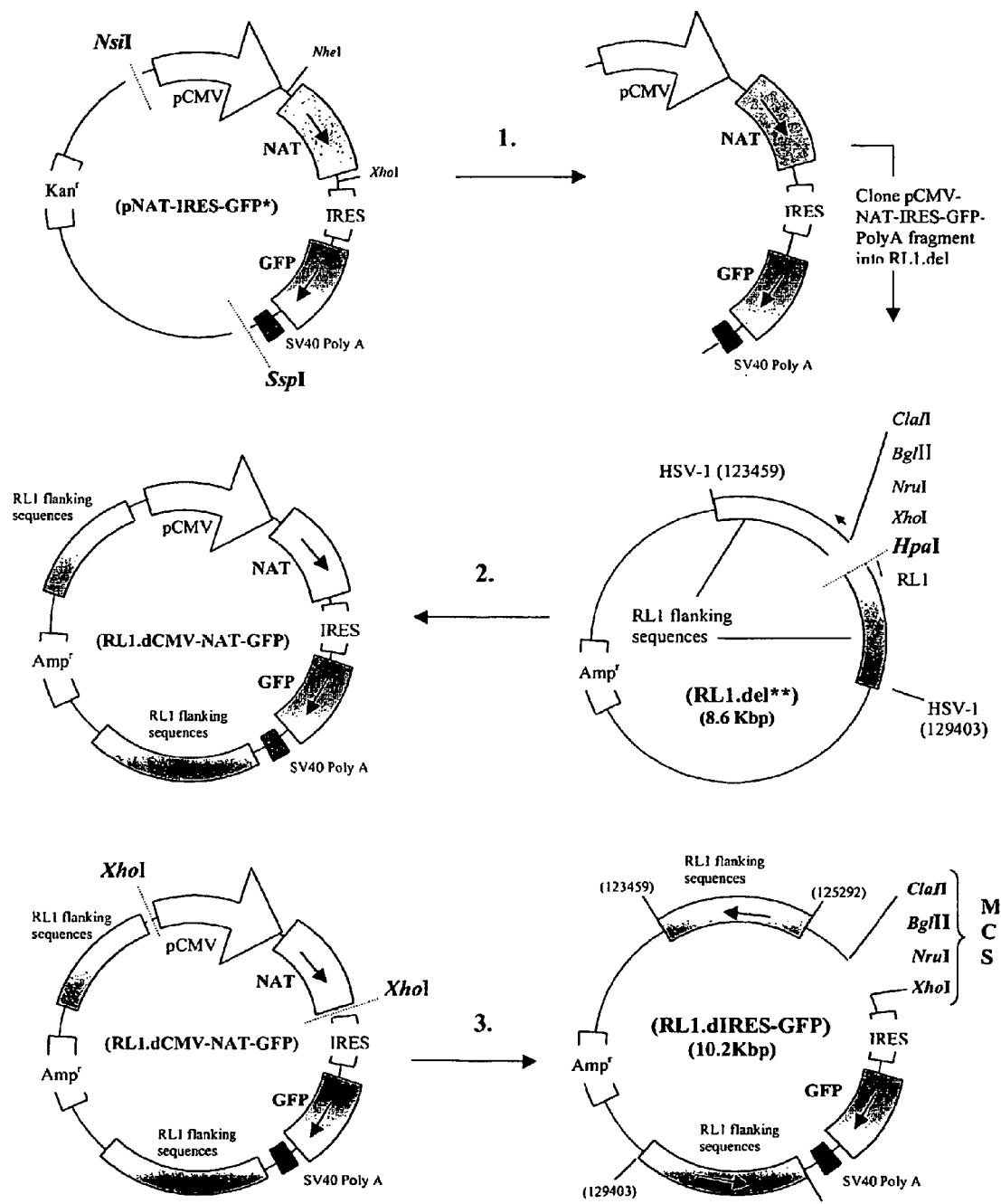
FIG. 1. Generation of plasmid RL1.dIRES-GFP from plasmids PNAT-IRES-GFP and RL1.del.

Plasmid RL1.dIRES-GFP was generated in three stages, illustrated in FIG. 1.
1. The DNA sequences containing the CMV IE promoter (pCMV), the NAT gene, the internal ribosome entry site (IRES), the GFP reporter gene and the SV40 polyadenylation sequences were excised from pNAT-IRES-GFP using NsiI and SspI and purified.
2. The purified pCMV-NAT-IRES-GFP-PolyA DNA fragment was cloned into RL1.del to form a new plasmid designated RL1.dCMV-NAT-GFP.
3. The pCMV-NAT DNA sequences of RL1.dCMV-NAT-GFP were excised using XhoI and the remainder of the plasmid re-ligated to form a novel plasmid designated RL1.dIRES-GFP. This novel plasmid contained a multi-cloning site (all sites shown are unique) upstream of an IRES, the GFP gene and the SV40 polyA sequences all within the HSV-1 RL1 flanking sequences. Recombinant ICP34.5 null HSV-1, expressing a gene of interest in the RL1 locus, can be generated by cloning the gene of interest (downstream of a suitable promoter) into the multi-cloning site and co-transfecting BHK cells with the plasmid and HSV-1 DNA. Recombinant virus expressing the target gene can be identified using GFP fluorescence.

Removal of the CMV promoter and noradrenaline transporter gene (pCMV-NAT) from RL1.dCMV-NAT-GFP, followed by re-ligation of the remainder of the plasmid, resulted in a novel plasmid (RL1.dIRES-GFP) containing a multi-cloning site (MCS), upstream of the encephalomyocarditis virus internal ribosome entry site (EMCV IRES), the GFP reporter gene and the SV40 PolyA sequences, all within RL1 flanking sequences. This novel arrangement of DNA sequences or 'smart cassette' allows ICP34.5 null HSV-1, expressing a gene of interest in the RL1 locus, to be easily generated by simply inserting the desired transgene (downstream of a suitable promoter) into the MCS and co-transfecting BHK cells with the plasmid and HSV-1 DNA. The IRES situated between the GFP gene and the MCS permits expression of two genes from the same promoter and so recombinant virus expressing the gene of interest also expresses GFP and can therefore be easily identified under a fluorescence microscope and purified.

Materials and Methods

Figure 2:
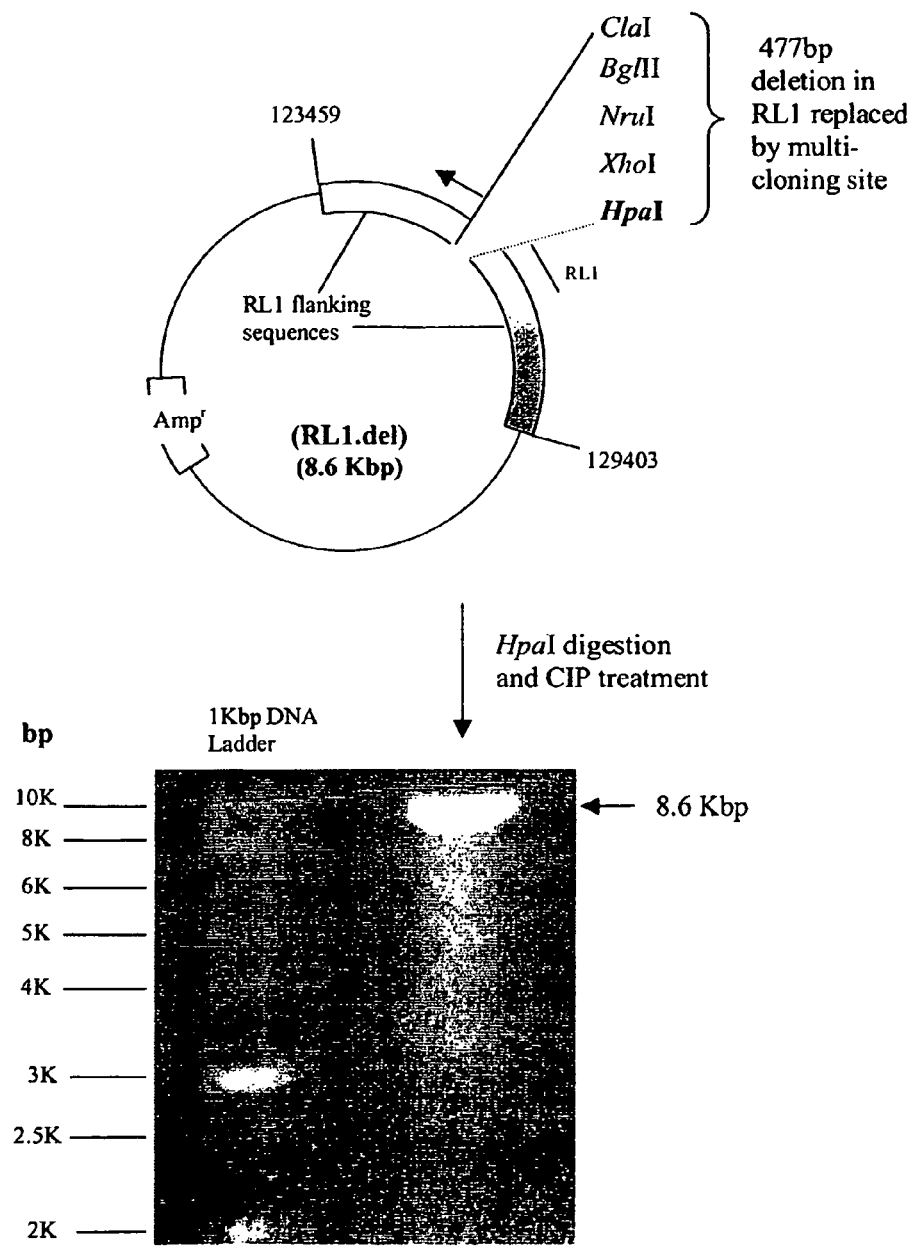
FIG. 2. Agarose gel electrophoresis of HpaI digested, CIP treated, RL1.del. RL1.del was digested with HpaI. The digested DNA was then treated with Calf Intestinal Phosphatase (CIP) to prevent the vector re-annealing to itself in subsequent ligation reactions. A sample of the digested/CIP treated DNA was electrophoresed, beside a 1 Kbp DNA ladder (Promega), on a 1% agarose gel. HpaI linearises the vector at 8.6 Kbp.

1 µg of RL1.del* was digested with 10 units HpaI (Promega) in a suitable volume of 10×buffer (Promega) and nuclease free water (Promega) at 37° C. for 16 hrs. The digested plasmid was then purified using the QIAquick PCR purification kit (Qiagen), treated with 10 units of Calf Intestinal Phosphatase (Promega), in a suitable volume of 10×CIP buffer and nuclease free water for 4 hrs at 37° C., before being purified again using a Qiaquick PCR purification kit. 5 µl of the purified DNA was electrophoresed on a 1% agarose gel to check its concentration (FIG. 2).

Figure 3:
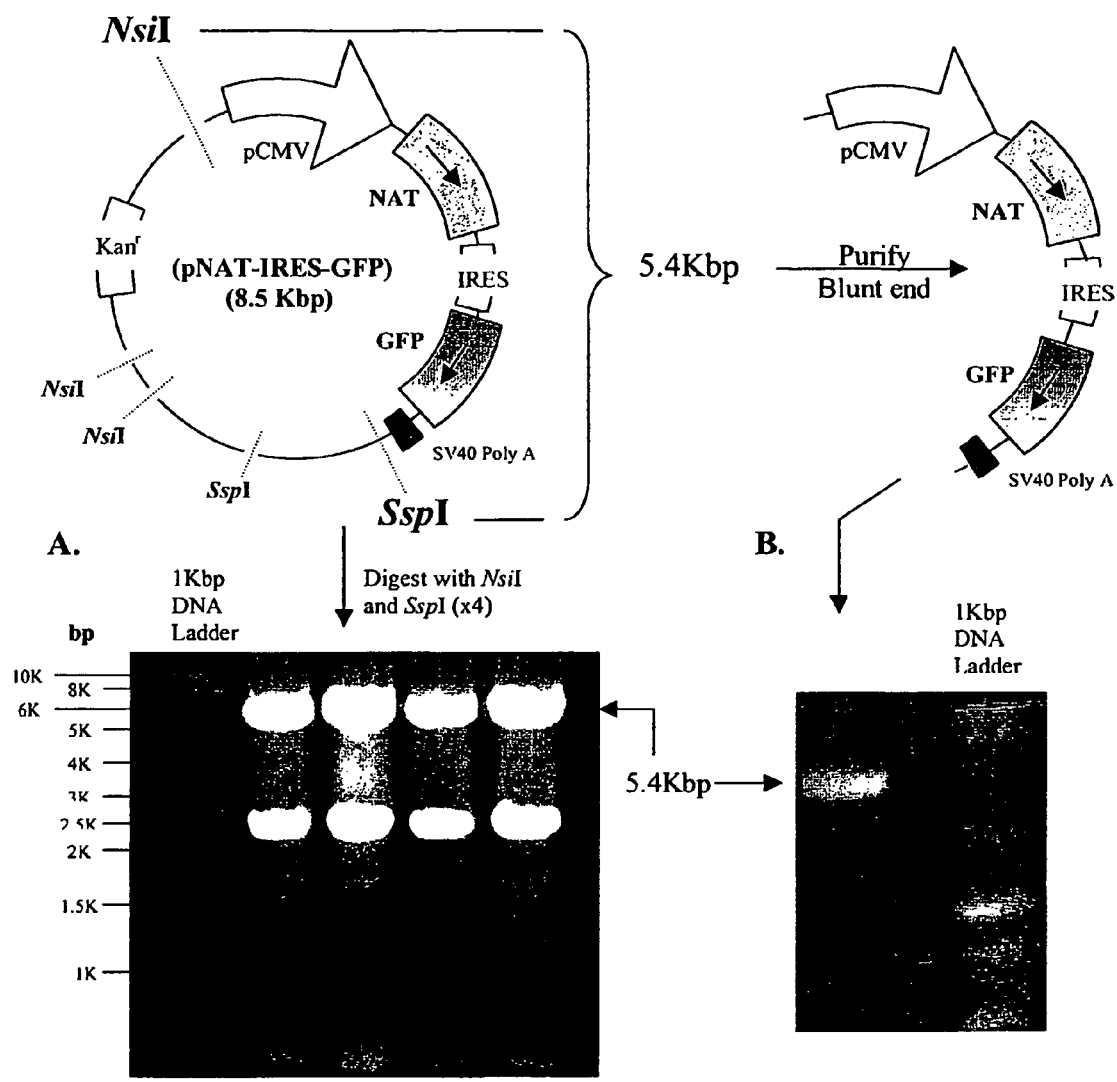
FIG. 3. Agarose gel electrophoresis of NsiI/SspI digested pNAT-IRES-GFP (A) and purified/blunt-ended pCMV-NAT-IRES-GFP-PolyA (B). Four NsiI/SspI digestions of pNAT-IRES-GFP were electrophoresed, beside a 1 Kbp DNA Ladder (Promega) on a 1% agarose gel. The 5.4 Kbp fragments (pCMV-NAT-IRES-GFP-PolyA) were purified from the gel. The purified DNA was blunt ended using Klenow polymerase and a sample electrophoresed on an agarose gel to check its concentration.

4×1 µg of pNAT-IRES-GFP** was digested with 10 units of NsiI and 10 units of SspI in a suitable volume of 10× buffer (Promega) and nuclease free water (Promega) at 37° C. for 16 hrs. The reaction mixture was electrophoresed in a 1% agarose gel for 1 hr at 110 volts. The 5.4 Kbp DNA fragment consisting of the CMV IE promoter (pCMV), upstream of the noradrenaline transporter gene (NAT), the encephalomyocarditis virus internal ribosome entry site (IRES), the gene for green fluorescent protein (GFP) and the SV40 polyadenylation sequences (SV40 Poly A), was excised using a sterile scalpel and the DNA purified from the gel using a QIAquick Gel Extraction kit (Qiagen). The eluted DNA was blunt ended using 3 units Klenow Polymerase (Promega) in accordance with the manufacturers instructions and the DNA purified using a QIAquick PCR purification kit (Qiagen). 5 µl of the purified DNA fragment was electrophoresed on a 1% agarose gel to check its concentration (FIG. 3).

Figure 4:
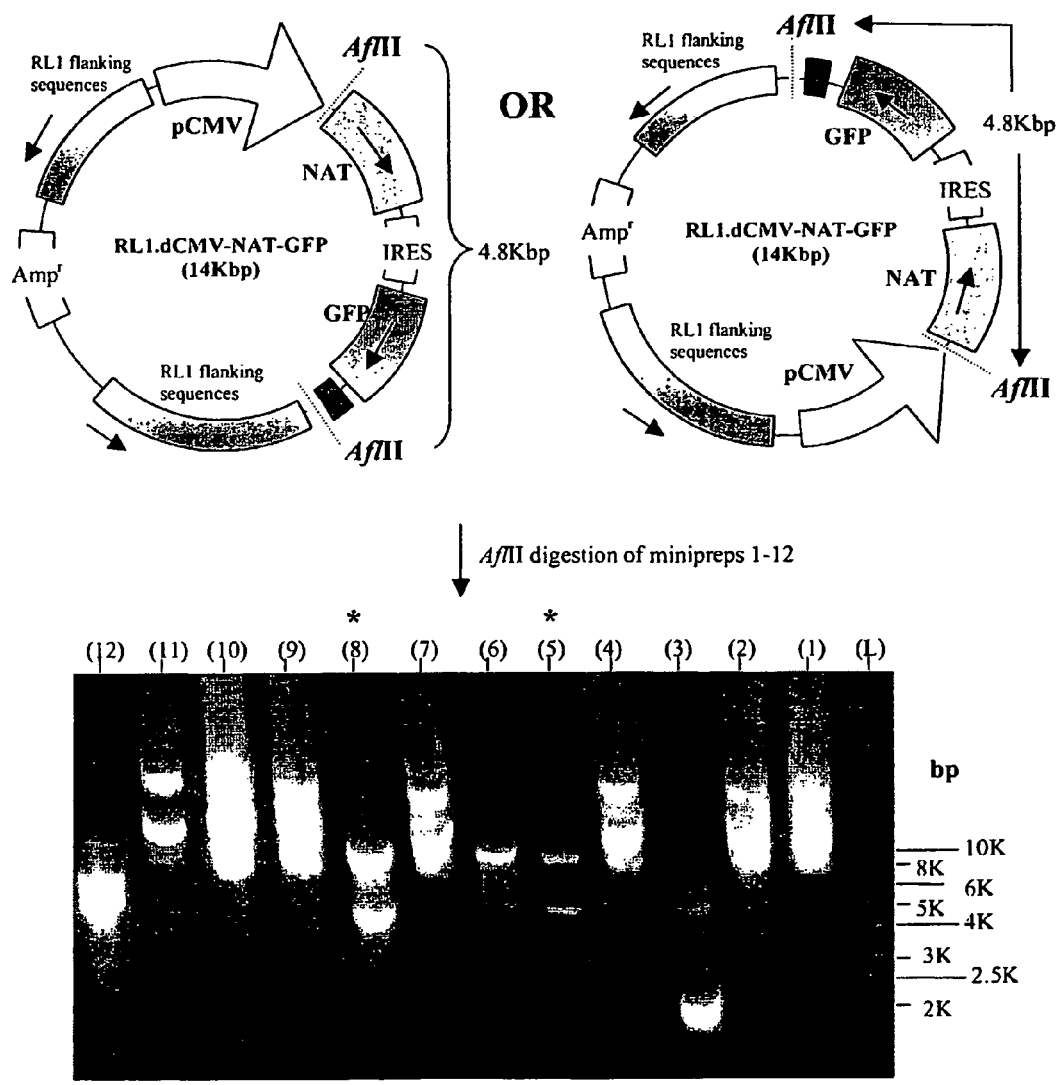
FIG. 4. Identification of RL1.del clones containing the pCMV-NAT-IRES-GFP-PolyA insert. Ligation reactions were set up with the purified, blunt ended pCMV-NAT-IRES-GFP-PolyA fragment and HpaI digested, CIP treated RL1.del. Bacteria were transformed with samples from the ligation reactions and plated out onto LBA (Amp$^r$) plates. Colonies were picked and plasmid DNA was extracted and digested with AflII. Digested samples were electrophoresed, beside a 1 Kbp DNA ladder (L) (Promega), on a 1% agarose gel.

Ligation reactions were carried out in small eppendorf tubes containing 5 units T4 DNA Ligase (Promega), a suitable volume of 10×DNA Ligase Buffer (Promega), nuclease free water (Promega) and various volumes of the HpaI digested/CIP treated RL1.del and blunt ended pCMV-NAT-IRES-GFP-SV40 Poly A DNA, at 16° C. overnight. Competent JM109 bacterial cells (Promega) were then transformed with various aliqouts of the ligation reactions***. Colonies formed on the plates were picked, had their plasmid DNA extracted using a Qiagen Plasmid Mini kit and screened for inserts using AflII (New England Biolabs) restriction enzyme analysis. Plasmid DNA containing the insert would produce two fragments of 4.8 Kbp and 9.2 Kbp following digestion with AflII. Two clones (clone 5 and 8) contained the insert (FIG. 4). The orientation of the insert in clone 5 (RL1.dCMV-NAT-GFP) was determined using XhoI restriction enzyme analysis (FIG. 5).

To generate RL1.dIRES-GFP from clone 5, the CMV-NAT portion of the CMV-NAT-IRES-GFP-SV40 PolyA insert was removed by digesting 4×500 ng of clone 5 with 10 units of XhoI in a suitable volume of buffer and water (Promega), overnight at 37° C. The digested DNA was electrophoresed on a 1% agarose gel at 110 volts for 1 hr (FIG. 6A). The 10.2 Kbp fragment consisting of the IRES, the GFP gene, the SV40 PolyA sequences and RL1 flanking sequences in a pGEM3Zf(−) (Promega) backbone, was excised using a sterile scalpel and the DNA purified from the gel using a QIAquick Gel Extraction kit.

Ligation reactions were performed in small eppendorf tubes containing 100 ng-500 ng purified DNA, 3 units T4 DNA Ligase (Promega), a suitable volume of 10×DNA Ligase Buffer (Promega) and nuclease free water (Promega) overnight at 16° C. Competent JM109 bacterial cells (Promega) were then transformed with various aliqouts of the ligation reactions***. Colonies formed on the plates were picked, had their plasmid DNA extracted using a Qiagen Plasmid Mini kit and screened using XhoI (Promega) restriction enzyme analysis. Colonies containing plasmid DNA from which CMV-NAT had been removed would produce one fragment of 10.2 Kbp when digested with XhoI. Several positive clones were found, one was isolated, and a large-scale plasmid preparation undertaken using Promega's Wizard Plus Maxipreps kit. The large-scale plasmid preparation was checked by digesting with XhoI (FIG. 6B). This plasmid DNA was subsequently named 'RL1.dIRES-GFP'.

Plasmid RL1.dIRES-GFP has been deposited in the name of Crusade Laboratories Limited having an address at Department of Neurology Southern General Hospital 1345 Govan Road Govan Glasgow G51 5TF Scotland on 3 Sep. 2003 at the European Collection of Cell Cultures (ECACC), Health Protection Agency, Porton Down, Salisbury, Wiltshire, SP4 0JG, United Kingdom under accession number 03090303 in accordance with the provisions of the Budapest Treaty.

RL1.del

*RL1.del was provided by Dr. E. McKie and is the pGEM-3Zf(−) plasmid (Promega) into which has been cloned an HSV-1 fragment (123459-129403) consisting of the RL1 gene and its flanking sequences. The 477 bp PflMI-BstEII fragment of the RL1 gene (125292-125769) has been removed and replaced with a multi-cloning site (MCS) to form RL1.del.

pNAT-IRES-GFP

** pNAT-IRES-GFP was supplied by Dr. Marie Boyd (CRUK Beatson Laboratories) and is the pIRES2-EGFP plasmid (BD Biosciences Clontech) into which she has cloned the bovine noradrenaline transporter (NAT) gene (3.2 Kbp), at the NheI and XhoI sites.

***Transformation of Bacterial Cells

10 µl of a glycerol E. coli stock was added to 10 ml 2YT medium in a 20 ml griener tube. This was placed in a 37° C. shaking incubator for 16-24 hrs until a saturated culture was obtained. 1 ml of this culture was then added to 100 ml of 2YT in a 500 ml sterile glass bottle and placed in the 37° C. shaking incubator for 3 hrs. The bacterial cells were pelleted by centrifugation at 2,000 rpm for 10 minutes (Beckman). The cells were then resuspended in $1/10^{th}$ volume of transformation and storage buffer (10 mM $MgCl_2$, 10 mM $Mg(SO)_4$, 10% (w/v) PEG 3,500, 5% (v/v) DMSO). The cells were placed on ice for between 10 minutes and 2 hrs, after which time they were considered competent for transformation.

1-10 µl of DNA was mixed with 100 µl of competent bacteria in eppendorf tubes, and the tubes placed on ice for 30 minutes. After this, the samples were 'heat shocked' by incubating the tubes in a 42° C. water bath for exactly 45 seconds before placing them on ice for a further 2 minutes. 1 ml of L-Broth was added, the tube inverted 2-3 times, and the bacteria incubated for 1 hr at 37° C. 100 µl of the transformed bacteria was plated out onto L-broth agar plates containing 100 µg/ml of the appropriate antibiotic (usually ampicillin or kanamycin). Plates were allowed to dry at room temperature, before incubating in an inverted position at 37° C. overnight.

EXAMPLE 2

Generation of ICP34.5 null HSV-1 Expressing a Gene Product of Interest and GFP Using Plasmid RL1.dIRES-GFP General Approach Generation of ICP34.5 null HSV-1 expressing a gene product of interest requires insertion of nucleotide sequence encoding the gene product (polypeptide) of interest, and often a desired promoter, at the MCS of RL1.dIRES.GFP followed by co-transfection of BHK cells with the linearised plasmid, containing the gene of interest, and HSV DNA. Following homologous recombination viral plaques expressing GFP are identified. FIG. 7 illustrates the method steps involved.

Referring to FIG. 7A plasmid DNA, containing the gene of interest and the desired promoter (X), is digested with restriction endonucleases to release the promoter/gene fragment.

The promoter/gene fragment is purified and cloned into the multi-cloning site (MCS) of RL1.dIRES.GFP forming a shuttle vector suitable for generating oncolytic HSV-1 (FIG. 7B). This vector contains HSV-1 sequences that flank the essential RL1 gene but does not contain the RL1 gene. The plasmid also contains the gene for Green Fluorescent Protein (GFP) downstream of an internal ribosome entry site (IRES). The IRES permits expression of both the gene of interest and the GFP gene from the same upstream promoter.

BHK cells are then co-transfected with linearised RL1.dIRES.GFP, now containing the gene of interest, and HSV-1 DNA (FIG. 7C). Following homologous recombination, designer virus, expressing the gene of interest and GFP, is generated and can be distinguished from wild type virus (also generated but not expressing GFP) under a fluorescence microscope.

Viral plaques, expressing GFP (and hence the gene of interest), are picked under the fluorescence microscope and purified until all wild-type HSV-1 has been removed. The recombinant HSV-1 is considered 100% pure when all the viral plaques are expressing GFP (FIG. 7D).

Once the recombinant virus is completely pure, an isolated plaque is picked and a highly concentrated stock is grown and titrated (FIG. 7E). Oncolytic HSV-1, expressing a gene product of interest from a selected promoter, is then ready for characterisation and in vitro examination of its tumour killing potential.

Materials and Methods

To generate recombinant ICP34.5 null HSV-1 expressing a gene of interest and GFP, requires the gene of interest, and often a suitable promoter, to be cloned into the MCS of RL1.dIRES-GFP in the forward orientation with respect to the GFP gene in this plasmid. Once this has been achieved the plasmid is linearised (i.e. digested with a restriction enzyme that cuts only once, usually SspI or ScaI) in an irrelevant region. 80% confluent BHK cells in 60 mm petri dishes are then co-transfected with HSV-1 DNA and linearised plasmid DNA as described below.

To generate replication restricted HSV-1, expressing the gene of interest and GFP, the gene of interest must be cloned into RL1.dIRES-GFP downstream of a suitable promoter (e.g. CMV IE). The promoter is required upstream of the gene of interest for the production of a bicistronic mRNA transcript. The IRES sequence between the two open reading frames in the transcript functions as a ribosome binding site for efficient cap-independent internal initiation of translation. The design enables coupled transcription of both the gene of interest and GFP, followed by cap-dependent initiation of translation of the first gene (gene of interest) and IRES-directed, cap-independent translation of GFP. Co-ordinate gene expression is thus ensured in this configuration.

Co-Transfection of Virus and Plasmid DNA by $CaPO_4$ and DMSO Boost

HSV-1 (17+) DNA and 0.1-1 μg linearized SMART cassette containing the gene and promoter of interest is pipetted into 1.5 ml eppendorf tubes containing 1 μl of calf thymus DNA (10 μg/ml) and an appropriate volume of distilled water to give a final volume of 165 μl. The solutions are very gently mixed using a 200 μl pipette tip. 388 μl of HEBS, pH 7.5, (130 mM NaCl, 4.9 mM KCl, 1.6 mM $Na_2HPO_4$, 5.5 mM D-glucose, 21 mM HEPES) is then added, the solution mixed, before adding 26.5 μl of 2M $CaCl_2$ dropwise and flicking the eppendorf tube two or three times. The samples are left at room temperature for 10-15 minutes then added dropwise to 80% confluent BHK's in 60 mm petri dishes from which the medium has been removed. Following incubation at 37° C. for 45 minutes, the cells are overlaid with 5 ml of ETC10 and incubated at 37° C. Three to four hours later, the media is removed and the plates washed with ETC10. For exactly 4 minutes, the cells are overlaid with 1 ml 25% (v/v) DMSO in HEBS at room temperature. After the 4 minutes, the cells are immediately washed three times with 5 ml ETC10 before overlaying with 5 ml of ETC10 and returning to the incubator. The following day, fresh medium is added to the cells. Two days later, when cpe is evident, cells are scraped into the medium, transferred to small bijoux and sonicated thoroughly. The sample is then stored at −70° C. until required (see section below on plaque purification).

N.B. The volume of virus DNA to add is determined by undertaking the above procedure without plasmid DNA, using a range of virus DNA volumes and choosing the volume that gives the greatest number of viral plaques on the BHK monolayer after 2 or 3 days.

Plaque Purification

Sonicated samples from co-transfection plates are thawed and serially diluted 10 fold in ETC10. 100 μl from neat to the $10^5$ dilution is plated out on confluent BHK's in 60 mm petri dishes from which the media has been removed. After 45 minutes incubation at 37° C., the cells are overlaid with 5 ml EMC10 and incubated at 37° C. for 48 hrs. The plates are then checked for the presence of viral plaques and those dishes with the fewest, most separated plaques are placed under a fluorescent stereomicroscope. Recombinant virus, designed to express the green fluorescent protein (GFP) in addition to the gene of interest, can clearly be distinguished from wild type virus using a GFP filter. Fluorescent plaques are picked using a 20 μl pipette and placed (including the tip) into an eppendorf tube containing 1 ml ETC10. The sample is thoroughly sonicated before making serial 10 fold dilutions in ETC10 and repeating the above purification procedure. The process is repeated typically 3-4 times until every plaque on the BHK monolayer is fluorescent. Once this has been achieved, 50 μl of this sample is used to infect BHK cells in roller bottles, in 50 ml ETC10, and a virus stock grown.

Tissue Culture Media

BHK21/C13 cells are grown in Eagle's medium (Gibco) supplemented with 10% newborn calf serum (Gibco) and 10% (v/v) tryptose phosphate broth. This is referred to as ETC10. For virus titrations and plaque purification, EMC10 (Eagles medium containing 1.5% methylcellulose and 10% newborn calf serum) is used to overlay the cells.

EXAMPLE 3

Construction of HSV1716/CMV-NTR/GFP

General Approach

HSV1716/CMV-NTR/GFP was generated by cloning a 1.6 Kbp BamHI fragment from pPS949[10], consisting of the *E. coli* nitroreductase (NTR) gene downstream of the CMV IE promoter (pCMV), into the MCS of the RL1.dIRES-GFP smart cassette, in the forward orientation with respect to the GFP gene in RL1.dIRES-GFP (FIG. 8). The resultant plasmid, named RL1.dCMV-NTR-GFP, was then linearised and recombinant virus generated and purified as described above. The plasmid pPS949 (referred to as 'pxLNC-ntr' in Ref 10) containing the NTR gene downstream of the CMV IE promoter (pCMV-NTR) in a pLNCX (Clontech) backbone, was a kind gift from Professor Lawrence Young, University of Birmingham, UK.

Materials and Methods

4×1 μg of pPS949 was digested with 10 units of BamHI (Promega), in a suitable volume of 10×buffer (Promega) and nuclease free water (Promega), at 37° C. for 16 hrs. The reaction mixture was electrophoresed in a 1% agarose gel for 1 hr at 110 volts. The 1.6 Kbp DNA fragment consisting of the CMV promoter upstream of the NTR gene (pCMV-NTR), was excised using a sterile scalpel and the DNA purified from the gel using a QIAquick Gel Extraction kit (Qiagen). 5 µl of the purified DNA fragment was electrophoresed on a 1% agarose gel to check its concentration (FIG. 9).

2 µg of the RL1.dIRES-GFP smart cassette was then digested with 15 units of BglII (Promega), in a suitable volume of 10×buffer (Promega) and nuclease free water (Promega), at 37° C. for 16 hrs. The digested plasmid was then purified using the QIAquick PCR purification kit (Qiagen), treated with 10 units of Calf Intestinal Phosphatase (Promega), in a suitable volume of 10×CIP buffer and nuclease free water for 4 hrs at 37° C. before being purified again using the Qiaquick PCR purification kit. 5 µl of the purified DNA was electrophoresed on a 1% agarose gel to check its concentration (FIG. 10).

Ligation reactions were carried out in small eppendorf tubes containing 5 units T4 DNA Ligase (Promega), a suitable volume of 10×DNA Ligase Buffer (Promega), nuclease free water (Promega) and various volumes of the BglII digested/CIP treated RL1.dIRES-GFP smart cassette and pCMV-NTR (BamHI ends), at 16° C. overnight. Competent JM109 bacterial cells (Promega) were then transformed with various aliqouts of the ligation reactions. Colonies formed on the plates were picked, had their plasmid DNA extracted using a Qiagen Plasmid Mini kit and screened for inserts using BglII/XhoI (Promega) restriction enzyme analysis. RL1.dIRES-GFP plasmid DNA containing the pCMV-NTR insert in the correct orientation would produce two fragments of 11.5 Kbp and 300 bp following digestion with BglII and XhoI. One clone (clone 4) was found to contain the insert in the correct orientation (FIG. 11). This plasmid was named 'RL1.dCMV-NTR-GFP'.

0.1-1 µg of RL1.dCMV-NTR-GFP was linearized by digesting with 10 units of ScaI (Promega), in a suitable volume of 10×buffer (Promega) and nuclease free water (Promega), at 37° C. for 16 hrs. A sample (5 µl) of the digested DNA was electrophoresed on a 1% agarose gel for 1 hr at 110 volts to check that it had been linearized. 80% confluent BHK cells were then co-transfected with a suitable volume of the remaining linearised DNA and HSV-1 DNA. Recombinant HSV-1, expressing GFP (and hence NTR), was identified and purified using a fluorescent microscope and a virus stock, named HSV1716/CMV-NTR/GFP, was grown and titrated on BHK cells (FIG. 12).

HSV1716/CMV-NTR/GFP has been deposited in the name of Crusade Laboratories Limited having an address at Department of Neurology Southern General Hospital 1345 Govan Road Govan Glasgow G51 5TF Scotland on 5 Nov. 2003 at the European Collection of Cell Cultures (ECACC), Health Protection Agency, Porton Down, Salisbury, Wiltshire, SP4 0JG, United Kingdom under accession number 03110501 in accordance with the provisions of the Budapest Treaty.

HSV1716/CMV-NTR/GFP Cell Killing

HSV1716/CMV-NTR/GFP replicates with almost identical kinetics to HSV1716 in BHK cells and 3T6 cells. BHK cells support the replication of ICP34.5 null HSV while confluent 3T6 cells do not. FIG. 13 shows that HSV1716/CMV-NTR/GFP will replicate as well as HSV1716 in permissive cell lines and that the introduction of exogenous genes, e.g. NTR and GFP, has not reduced the oncolytic potential of the ICP34.5 null HSV. The fact that HSV1716/CMV-NTR/GFP fails to replicate in 3T6 cells also indicates that this recombinant HSV is an ICP34.5 null mutant.

FIG. 14 is a Western blot demonstrating that no ICP34.5 polypeptide is expressed from HSV1716/CMV-NTR/GFP, and that the virus is thus useful as a gene therapy vector.

FIG. 15 is another Western blot demonstrating expression of NTR in a variety of cell lines infected with HSV1716/CMV-NTR/GFP, including a human malignant melanoma cell line (C8161) and confluent 3T6 cells in which ICP34.5 null HSV does not replicate. Expression of NTR in confluent 3T6 cells, following infection with HSV1716/CMV-NTR/GFP, is encouraging as it demonstrates that replication of this ICP34.5 null mutant is not required for expression of the prodrug-activating gene (i.e. NTR). Some tumour cells in vivo will not support the replication of ICP34.5 null HSV and as such, will not be killed with HSV1716.

FIG. 16 shows the results from a cytotoxicity assay performed in confluent 3T6 cells. Infecting confluent 3T6 cells with an ICP34.5 null mutant (HSV1716/CMV-NTR/GFP), at a multiplicity of infection (MOI) of 1 plaque forming units (pfu)/cell, does not result in any significant cell death, neither does separate incubation of the cells with 50 µM CB1954. However, significant cell death is evident 72 hrs post infection with 1 pfu/cell HSV1716/CMV-NTR/GFP when 50 µM CB1954 is included in the growth medium. This clearly demonstrates that when there is no replication of the virus, substantial cell death is still possible from virus directed enzyme prodrug therapy (VDEPT).

Infecting confluent 3T6 cells with an ICP34.5 null mutant at a MOI of 10 pfu/cell will result in cell death, by a mechanism known as 'viral antigen overload'. However, the level of cell killing is even more pronounced (approximately 20% more), when 50 µM CB1954 is included in the growth medium.

A similar cytotoxicity assay was performed in human C8161 melanoma cells, the results are set out in FIG. 17. Unlike confluent 3T6 cells, C8161 cells do support the replication of ICP34.5 null HSV. Therefore, cell death will occur following infection of the cells with ICP34.5 null HSV, at 1 pfu/cell. However, when CB1954 is included in the overlay of HSV1716/CMV-NTR/GFP infected cells, the cells are killed more efficiently and more quickly. No enhanced cell killing is evident when CB1954 is included in the overlay of cells infected with HSV1716-GFP. These results demonstrate that enhanced cell killing is possible in human tumour cells.

Cell culture images for the cytotoxicity assays performed in confluent 3T6 and human C8161 melanoma cells are shown in FIGS. 18 and 19.

EXAMPLE 4

In Vivo Evaluation of the Anti-Tumour Activity of a Selectively Replication Competent Herpes Simplex Virus in Combination with Enzyme Pro-Drug Therapy The anti-tumour activity of a selectively replication competent herpes simplex virus in combination with an enzyme prodrug therapy approach in appropriate animal models in vivo was investigated.

The parental virus, HSV 1716 is a selectively replication competent mutant of the herpes simplex virus 1 (HSV 1) which lacks both copies of the RL1 gene that encodes the protein ICP 34.5. This protein is a specific determinant of virulence. The function of this protein has been described at length elsewhere[12]. The virus can grow only in cells that have a high level of functional PCNA. High levels of PCNA are found only in cells that are dividing such as tumour cells and not normal differentiated cells.

It has already been shown that HSV 1716 can achieve selective tumour cell killing with minimal toxicity and improved survival times in a number of animal models[13] Initial phase 1 clinical trials using HSV1716 virus in patients has also meet with some success[14, 15].

Although HSV1716 selectivity replicates in tumour reducing the tumour bulk by cell lysis the inventors did not anticipate HSV1716 to lytically replicate in all cells in the tumour due to the heterogeneity of the cell type and growth state.

In order to enhance the efficacy of the tumour cell killing—hence kill the entire tumour—the inventors have constructed a derivative of HSV1716 designated HSV1716/CMV-NTR/GFP that expresses the *E. Coli* nitroreductase gene (ntr) under the control of a CMV early promoter (see example 3 above). In this example and the figures referred to HSV1716/CMV-NTR/GFP is called HSV1790.

The enzyme ntr converts the inactive prodrug CB1954 to a functional cytotoxic alkylating agent that kills both dividing and non-dividing cells by apoptosis. This active drug is diffusible and membrane permeable resulting in an efficient bystander effect, i.e. wherein the activated drug may have an effect on surrounding cells.

As the prodrug will only be converted to its active form in the tumour which has been infected with ntr expressing virus, toxicity to normal cells is avoided hence improving the therapeutic index following systemic delivery of this compound.

Initial in vitro experiments using this combination have already shown enhanced cell kill using this virus in combination with CB1954 in a number of cell lines.

This example further evaluates this combination approach in vivo in appropriate animal models.

Results

Months 1-3

Months 1-3 were taken up mainly by in vitro work. During this time period high titre, sterile virus stock was generated for use in the xenograft models.

Xenograft models were also generated in athymic nude mice using the cell line A2780, a human ovarian epithelial carcinoma line initially derived from a tumour sample from an untreated patient (European Collection of Cell Cultures (ECACC) CAMR, Porton Down, Salisbury, Wiltshire, SP4 0JG, United Kingdom, accession number 93112520).

Generation of a gliomal xenograft model was attempted using 2 gliomal lines that were available in house, LN-18 and U373MG. There are reports in the literature of both being successfully grown as xenografts in athymic mice.

However, as shown in the table below the inventors failed to see any xenograft growth up to 28 days after injection with 5 million cells subcutaneously.

Table 1

| Cell Line | No of cells injected per mice | Number of mice | Presence of xenograft 28 days after cell injection |
|---|---|---|---|
| LN 18 | 5 million | 5 | 0/5 |
| U373 MG | 5 million | 5 | 0/5 |

A2780 Tumour Take

As reported previously A2780 have a Take Rate of approximately 50%—that is 50% of mice that are injected with 5 million cells per flank subcutaneously will develop xenografts. When the number of cells injected was increased to 10 million or more an increase in take rate of approximately 15-25% was seen, giving an overall take rate of 65-75%.

Thus increasing the number of gliomal cells injected may increase the take rate of these cell lines Dose Response to the HSV 1790 Virus Before the mice can be treated with a combination of virus and prodrug, first one must carry out experiments to make informed decisions about how much of the virus, and the prodrug to give.

A dose response experiment will allow one to find both the most appropriate does of the virus to use in the experiments and the maximum tolerated dose (MTD) of the virus, that is, the largest amount of the virus that can be given to a single mouse without adverse side effects. Small groups of tumour bearing mice are given a small dose of virus. Assuming they do not have any adverse effects another group is given a larger dose of virus. This continues until either the mice start to suffer ill effects or we reach a maximum dose.

The maximum amount of virus that can be intratumourally injected is 100 µl, hence the maximum dose from our current stock is $10^9$ PFU per injection.

FIG. 20 shows the weight change in the mice after injection with a variety of doses of virus. Weight is a good indicator of the animals overall health. Any loss of weight signifies that the treatment is not being well tolerated. Where an animal loses more than 20% of its initial body weight it was sacrificed immediately.

A dose of $10^9$ PFU of the HSV 1790 virus is not tolerated by these mice, they rapidly lost body weight and were sacrificed at Day 3 post injection. Doses of $10^8$ PFU or less were better tolerated, the mice initially lost weight in the days following injection but quickly recovered to approximately their initial body weights.

It should be pointed out that as the experiment progresses the animals appear to be increasing in weight. This is almost certainly due to the fact that it is total body weight that is measured, which includes the weight of any tumour that is forming.

Response of the Tumour to HSV 1790 Treatment

Tumour volume was measured daily after intratumoural injection of the HSV 1790 virus to look for any growth delay or regression of the tumours.

FIG. 21 shows the change in tumour volume as measured over a period of 100 days. If the tumour was injected with PBS only as a control the tumour increased in size rapidly and by approximately Day 13 post injection the tumours had become too large and the animals had to be sacrificed.

Treatment with all doses of virus appeared to delay the growth of the tumour to some degree. Doses of $10^5$ PFU increased the longevity of the mice by approximately 12 days while mice injected with $10^6$ PFU virus tumours survived for an extra 23 days compared to the control group before the tumours became prohibitively large. Perhaps surprisingly the group of mice injected with $10^8$ PFU of virus survived only slightly longer than the control group. It is possible there were a large number of non infectious particles or that sheer number of particles caused the cells which the virus would have grown in to be killed.

The group of mice treated with $10^7$ PFU of virus survived the longest and indeed two out of three of the mice did not have any visible signs of tumour when sacrificed at day 100.

Naked DNA Experiments

In order to check the alterations in tumour growth are due to the virus itself and not a result of the CMV-ntr plasmid DNA that had been introduced to the HSV 1716 virus, an experiment was set up looking at the effect of the CMV-ntr plasmid DNA alone and in combination with the prodrug CB1954.

Mice were randomised into treatment groups of 6 animals each when tumour diameters are approximately 5 mm (this is Day 0). FIG. 22 shows the starting tumour diameters for the mice used in this experiment. Two groups of mice were administered CMV-ntr plasmid by direct intratumoural injection at a dose of 0.2 mg DNA per injection. One of these groups was then administered with a single dose of 80 mg/kg of CB1954 on Day 2 by intra-peritoneal injection. The third group of mice had a single administration of CB1954 (80 mg/kg) by intra-peritoneal injection on Day 2 following intratumoural injection of saline control at Day 0. Animals were weighed daily (FIG. 23) and daily caliper measurements performed until the tumour sizes were in the region of 20 mm by 20 mm. Tumour volumes were estimated from these measurements (volume=d3×6) (FIG. 24). In addition any toxicity from these administered agents was determined. On the basis of these experiments the inventors determined that neither the CMV-ntr alone, CB1954 alone or the combination of both CMV-ntr and CB1954, has any anti-tumour activity as determined by tumour regression in this model system (FIG. 24).

Scheduling Experiment

Previous dose response experiments have shown that doses of less than $10^8$ PFU virus per mouse do not appear to have any adverse effect of the animals health.

A dose of $10^7$ PFU virus per mouse resulted in a great reduction in tumour growth, indeed after 100 days two out of three of the mice in the group had no visible tumour. This is very encouraging—the virus only at high doses may be enough to delay growth or cause tumour regression.

However to look at the effect of a combination of the virus and the prodrug CB 1954 a lower dose of the virus was studied—if the treatment of the virus alone results in growth delay for such a long period one would be unable to ascertain the addition or synergistic effects of the prodrug.

The inventors proceeded to investigate two doses of the virus in combination with CB1954. The doses selected were $10^5$ PFU and $10^6$ PFU. Both these doses caused some tumour growth delay in earlier experiments.

The prodrug is given as an 80 mg/kg intra-peritoneal injection, after dissolving the powdered form in 10% acetone and then making up the volume with peanut oil.

Another factor that determines how well the drug will work—hence how much tumour growth delay or regression is seen—is when the drug is actually given. As the prodrug will only be converted to an active substrate in the presence of NTR it was considered that the virus containing the NTR will have to been given first. It was also considered that if the virus is given time to replicate and produce more NTR then the prodrug may have a more pronounced effect.

To discover the optimal doses of both the virus and the drug and the optimal times of these treatments a scheduling experiment was set up.

Mice were randomized into treatment groups (treatment regimes shown in Table 2) of 3 animals when tumour diameters were approximately 5 mm (tumour volume 0.5-1.5 $mm^3$). FIG. 25 shows the starting tumour volumes of each of the groups.

TABLE 2

| | Treatment groups |
|---|---|
| 1 | $10^5$ HSV 1790 + drug (Day 2) + Drug (Day 10) |
| 2 | $10^5$ HSV 1790 + drug (Day 2) + vehicle (Day 10) |
| 3 | $10^5$ HSV 1790 + vehicle (Day 2) + drug (Day 10) |
| 4 | $10^5$ HSV 1790 + vehicle (Day 2) + vehicle (Day 10) |
| 5 | No virus + drug (Day 2) + drug (Day 10) |
| 6 | No virus + drug (Day 2) + vehicle (Day 10) |
| 7 | No virus + vehicle (Day 2) + drug (Day 10) |
| 8 | No virus + vehicle (Day 2) + vehicle (Day 10) |
| 9 | $10^6$ HSV 1790 + vehicle (Day 2) + vehicle (Day 10) |
| 10 | $10^6$ HSV 1790 + drug (Day 2) + vehicle (Day 10) |
| 11 | $10^6$ HSV 1790 + drug (Day 2) + drug (Day 10) |
| 12 | $10^6$ HSV 1790 + drug (Day 2) + drug (Day 10) + drug (Day 15) |
| 13 | No virus + drug (Day 2) + drug (Day 10) |

TABLE 2-continued

| | Treatment groups |
|---|---|
| 14 | No virus + vehicle (Day 2) + vehicle (Day 10) |
| 15 | $10^5$ HSV 1716 + drug (Day 2) + drug (Day 10) |
| 16 | $10^5$ HSV 1716 + vehicle (Day 2) + vehicle (Day 10) |
| 17 | $10^5$ HSV 1716 + drug (Day 2) + vehicle (Day 10) |
| 18 | $10^5$ HSV 1716 + vehicle (Day 2) + drug (Day 10) |

The treatment groups were administered with a single direct intratumoural injection of the virus and dose determined for that group. The virus was diluted PBS+10% serum. 'No virus' control groups received an intratumoural injection of 100 μl of PBS+10% serum. This day was designated as Experimental Day 0.

The intratumoural injections did not appear to have any adverse effects on the mice. Some tumours bleed slightly after injection but not to a great degree. The animals did not lose body weight (FIG. 26) and their behaviour did not appear to alter. In all the tumours that bleed slightly, the following day the healing process had begun and within 3-5 days there was little evidence of any puncture wound on any tumour.

Injections of CB1954 were given to the appropriate groups at days 2, 10 and 15. A dose of 80 mg/kg—the equivalent of approx. 2 mg per mouse—was given. The powdered form of the CB1954 drug (from Sigma) was dissolved in acetone to 10% of the final volume (10 μl per 2 mg). The volume was then made up to 2 mg CB1954 in 100 μl using peanut oil. A syringe was used to mix the drug as peanut oil is thick and viscous. The drug was made up fresh every time.

The appropriate groups were then injected intra-peritoneal with this solution. Control groups which were not receiving drug were injected intra-peritoneal with a 100 μl solution of 10% acetone in peanut oil.

No swelling or irritation at the site of injection was noted on any of the mice either at time of injection or at any later time point. The mice appeared slightly lethargic for a short period after the injection but did not lose any body weight (FIG. 26) or show signs of lethargy the following day.

No Virus +CB1954 prodrug

Groups 5, 6, 7, 8, 13 & 14 looked at the effect of prodrug alone on tumour growth. FIG. 27 shows that there is little effect on tumour growth when CB1954 is given alone.

$10^5$ PFU virus +/−CB1954 Prodrug $10^5$ PFU virus was given at Day 0 followed by either prodrug or vehicle at Days 2 and 10.

As can be seen from the graph in FIG. 28 tumours treated with either virus only or virus and prodrug did not grow as large as the untreated tumour. The tumour treated with the virus grew only to approximately half the size of the untreated control.

Treatment with virus and prodrug resulted in tumours which grew to only approx 2-3 $mm^3$ in volume. This is significantly less than the untreated tumours which grew in size to approx 20 $mm^3$.

$10^6$ PFU virus +/−CB1954 Prodrug

FIG. 29 shows the changes in tumour volume over time after treatment with a higher dose of virus, $10^6$ PFU per injection, in combination with the prodrug, given as described in Table 2. As with the lower virus dose, treatment with either virus only, or in combination with CB1954, results in significantly smaller tumours compared to the untreated controls.

HSV 1716 Virus in Combination with CB1954 Prodrug

The parental strain of the virus, which has not been engineered to contain the CMV-ntr DNA was examined for its effects on tumour growth delay. This virus does have an oncolytic effect, however it doesn't contain the NTR gene needed to convert the inactive prodrug into its active metabolite. Therefore one would not expect any additional or synergistic effects when the prodrug is added in combination with the virus. FIG. 30 shows the results of this experiment.

The combination of the virus and the prodrug appeared to produce some reduction in tumour growth compared to the untreated control tumours.

The groups used in these results contained only 2 or 3 animals. The animals used were also older and their tumours had taken longer to grow than those used in previous experiments. Hence it is possible that repeating the experiment with a larger number, with younger mice or quicker forming tumours may result in a more marked growth delay after treatment with the HSV 1716 virus.

Comparison of HSV 1790 (at $10^5$ and $10^6$) and HSV 1716 in Combination with CB1954 Prodrug FIG. 31 shows a comparison between the two doses of the HSV 1790 virus in combination with the prodrug and the HSV 1716 prodrug combination. The parental virus HSV 1716 shows some growth delay in comparison with the untreated control. We would assume that this growth delay is due to the oncolytic effect of the virus as the NTR gene is not present to alter the inactive prodrug into its active form.

Tumour growth is reduced further when the tumour is treated with the HSV 1790 virus containing the NTR gene. This appears to be dose dependent—the higher dose of the virus results in a greater growth delay than the lower dose.

In conclusion it would appear from these results that indeed the HSV 1790 virus used in combination with the prodrug CB1954 results in growth delay in the model system examined. Giving both virus and drug in combination has a greater effect than given either alone.

It appears that the timing at which the prodrug is given after virus treatment is important. When CB1954 was given soon after viral injection (Day 2 post viral injection) tumour growth was not delayed as much as if the drug was given at a later date (Day 10). It may be that given at Day 2 the drug killed the cells that were supporting viral growth and replication and actually reduced the oncolytic effect of the virus.

By day 10 the virus may have replicated and killed as many cells by oncolysis as possible. It is anticipated that due to heterogeneity of the cell type and growth state that all the cells within a tumour would not be susceptible to lysis by the virus. The drug then comes in and 'mops up' by killing any cells that are supporting viral growth (hence containing the NTR gene) but were not susceptible to oncolysis. As the active drug is diffusible and membrane permeable it may have a bystander effect—killing not only the cells infected with the virus but also its near neighbours.

REFERENCES

1. B L Liu, M Robinson, Z-Q Han, R H Branston, C English, Preay, Y McGrath, S K Thomas, M Thornton, P Bullock, C A Love and R S Coffin; Gene Therapy (2003) 10, 292-303.
2. WO 92/13943
3. A Dolan, E Mckie, A R Maclean, D J McGeoch; Journal of General Virology (1992) 73 971-973.
4. Aidan Dolan, Fiona E Jamieson, Charles Cunnigham, Barbara C Barnett Duncan J McGeoch; Journal of Virology March 1998 2010-2021.
5. Joany Chou, Earl R Kern, Richard J Whitley, Bernard Roizman; Science (1990) 250 1262-1265.
6. Coffin R S, MacLean A R, Latchman D S, Brown S M; gene therapy (1996) October 3(10) 886-91.
7. McKie E A, Hope R G, Brown S M, Maclean A R; Journal of General Virology, (1994) April 75(Pt4) 733-41.
8. McKay E M, McVey B, Marsden H S, Brown S M, MacLean A R; Journal of general Virology, (1993) November 74(Pt11) 2493-7.
9. Joany Chou, Bernard Roizman; Journal of Virology; (1990) March 1014-1020.
10. Green, N. K., Youngs, D. J, J. P. Neoptolemos, F. Friedlos, R. J. Knox, C. J. Springer, G. M. Anlezark, N. P. Michael, R. G. Melton, M. J. Ford, L. S. Young, D. J. Kerr, and P. F. Searle; Cancer Gene Therapy (1997) 4:229-238.
11. Cherry L. Estilo, Pornchai O-charoenrat, Ivan Nagai, Snehal G. Patel, Pabbathi G. Reddy, Su Dao, Ashok R. Shaha, Dennis H. Kraus, Jay O. Boyle, Richard J. Wong, David G. Pfister, Joseph M. Huryn, Ian M. Zlotolow, Jatin P. Shah and Bhuvanesh Singh; Clinical Cancer Research (June 2003) Vol. 9 2300-2306.
12. Brown S M, Harland J, MacLean A R et al. Cell type and cell state determine differential in vitro growth of non-neurovirulent ICP 34.5 negative herpes simplex virus. *J Gen Virol* 1994; 75: 2367-2377.
13. McKie E A, MacLean A R, Lewis A D et al. Selective in vitro replication of herpes simplex virus type 1 (HSV-1) ICP 34.5 null mutants in primary human CNS tumours—evalution of a potentially effective clinical therapy. *Br J Cancer* 1996; 74: 745-752.
14. Rampling R, Cruickshank G, Papanastassiou V et al. Toxicity evalution of replication-competent herpes simplex virus (ICP 34.5 null mutant 1716) in patients with recurrent malignant glioma. *Gene Ther* 2000; 7: 859-866.
15. Papanastasssiou V, Rampling R, Fraser M et al. The potential for efficacy of the modified (ICP 34.5-) herpes simplex virus HSV 1716 following intratumoural injection into human malignant glioma: a proof of principle study. *Gene Ther* 2002; 9: 525-526.
16. Johansson E, Parkinson G N, Denny, W A and Neidle S. Studies on the Nitroreductase Prodrug-Activating System. Crystal Structures of Complexes with the Inhibitor Dicoumarol and Dinitrobenzamide prodrugs and of the Enzyme Active Form. J. Med. Chem. 2003, 46, 4009-4020.
17. Hu L, Yu C, Jiang Y et al. Nitroaryl Phosphoramides as Novel Prodrugs for *E. coli* Nitroreductase Activation in Enzyme Prodrug Therapy. J. Med. Chem. 2003 46, 4818-4821.

The invention claimed is:

1. The herpes simplex virus HSV1716/CMV-NTR/GFP deposited under ECACC accession number 03110501.

* * * * *